_United States Patent_ [19]

Schaaf et al.

[11] 3,954,741

[45] May 4, 1976

[54] N-SUBSTITUTED PROSTAGLANDIN CARBOXAMIDES

[75] Inventors: Thomas K. Schaaf, Old Lyme, Conn.; Leonard J. Czuba, Canterbury, England; Hans-Jurgen E. Hess, Old Lyme, Conn.

[73] Assignee: Pfizer Inc., New York, N.Y.

[22] Filed: May 30, 1973

[21] Appl. No.: 365,244

Related U.S. Application Data

[63] Continuation-in-part of Ser. No. 260,518, June 7, 1972, abandoned.

[52] U.S. Cl. .......................... 260/240 R; 424/283; 424/320; 424/321; 260/329 S; 260/343.6; 260/346.2 R; 260/468 D; 260/470; 260/471 A; 260/556 A; 260/556 AR; 260/557 R; 260/558 R; 260/559 R; 260/561 R

[51] Int. Cl.² ............. C07C 333/38; C07C 143/76; C07C 143/78

[58] Field of Search ..... 260/468 D, 471 A, 556 AR, 260/550 A, 561 R, 559 R, 558 R, 468 D, 240 R, 557, 329 S

[56] References Cited
UNITED STATES PATENTS 3,751,463   8/1973   Caton et al. .................... 260/557 R

FOREIGN PATENTS OR APPLICATIONS 2,150,361   4/1972   Germany ....................... 260/468 D

OTHER PUBLICATIONS

Hickinbottom, Reactions of Organic Compounds, Frontis Page and pp. 226–229 (1948, 2nd ed).

Bojesen et al., Biochimica et Biophysica Acta, Vol. 280, pp. 614 to 625, (1972).

Chereonis et al., Semimicro Qualitative Organic Analysis, Frontispage and pp. 179 to 180, Thomas Y. Crowell Co., NY, (1947).

_Primary Examiner_—John D. Randolph
_Attorney, Agent, or Firm_—Connolly and Hutz

[57] ABSTRACT

The N-substituted prostaglandin carboxamides and various intermediates employed in their preparation. Such prostaglandin analogs exhibit the same activity profiles as the corresponding natural prostaglandin but with increased duration of action and increased selectivity of action.

11 Claims, No Drawings

N-SUBSTITUTED PROSTAGLANDIN CARBOXAMIDES

CROSS REFERENCE TO RELATED APPLICATIONS

The application is a continuation-in-part of our copending application Ser. No. 260,518 filed June 7, 1972 and now abandoned.

BACKGROUND OF THE INVENTION

This invention relates to certain novel analogs of the naturally occurring prostaglandins. In particular, it relates to novel N-substituted prostaglandin carboxamides and various novel intermediates and reagents useful in their preparation. The substitution in these novel compounds comprises alkanoyl, cycloalkanoyl, aroyl, and substituted aroyl, alkylsulfonyl, or arylsulfonyl and substituted arylsulfonyl.

The prostaglandins are C-20 unsaturated fatty acids which exhibit diverse physiological effects. For instance, the prostaglandins of the E and A series are potent vasodilators (Bergstrom, et al., *Acta Physiol. Scand.* 64:332-33, 1965 and Bergstrom, et al., *Life Sci.* 6:449-455, 1967) and lower systemic arterial blood pressure (vasodepression) on intravenous administration (Weeks and King, *Federation Proc.* 23:327, 1964; Bergstrom, et al., 1965, op. cit.; Carlson, et al., *Acta Med. Scand.* 183:423-430, 1968; and Carlson, et al., *Acta Physiol, Scand.* 75:161-169, 1969). Another well known physiological action for $PGE_1$ and $PGE_2$ is as a bronchodilator (Cuthbert, *Brit. Med. J.* 4:723-726, 1969).

Still another important physiological role for the natural prostaglandins is in connection with the reproductive cycle. $PGE_2$ is known to possess the ability to induce labor (Karim, et al., *J. Obstet Gynaec. Brit. Cwlth.* 77:200-210, 1970), to induce therapeutic abortion (Bygdeman, et al., *Contraception*, 4, 293 (1971) and to be useful for control of fertility (Karim, *Contraception*, 3, 173 (1971)). Patents have been obtained for several prostaglandins of the E and F series as inducers of labor in mammals (Belgian Patent 754,158 and West German Pat. No. 2,034,641) and on $PGF_1$, $F_2$, and $F_3$ for control of the reproductive cycle (South African Pat. No. 69/6089).

Still other known physiological activities for $PGE_1$ are in the inhibition of gastric acid secretion (Shaw and Ramwell, In: *Worcester Symp. on Prostaglandins*, New York, Wiley, 1968, p. 55-64) and also of platelet aggregation (Emmons, et al., Brit. Med. J. 2:468–472, 1967).

It is now known that such physiological effects will be produced in vivo for only a short period, following the administration of a prostaglandin. A substantial body of evidence indicates that the reason for this rapid cessation of activity is that the natural prostaglandins are quickly and efficiently metabolically deactivated by β-oxidation of the carboxylic acid side-chain and by oxidation of the 15α-hydroxyl group (Anggard, et al., Acta. Physiol. Scand., 81, 396 (1971) and references cited therein).

It was, of course, considered desirable to create analogs of the prostaglandins which would have physiological activities equivalent to the natural compounds, but in which the selectivity of action and the duration of the activity would be increased. Increased selectivity of action would be expected to alleviate the severe side effects, particularly gastrointestinal side effects, frequently observed following systemic administration of the natural prostaglandins (see *Lancet*, 536, 1971).

SUMMARY OF THE INVENTION

The novel compounds of this invention, the N-substituted prostaglandin carboxamides, in which the carboxylic acid moiety is replaced with an N-substituted carboxamide, and in which the 15β-hydrogen may be replaced by a 15β-lower alkyl group if desired, uniquely satisfy the above mentioned requirements. That is, they possess highly selective activity profiles compared with the parent prostaglandins and in many cases they exhibit a longer duration of action. A prime example of the therapeutic importance of these prostaglandin analogs is the efficacy of N-acetyl prostaglandin $E_2$ carboxamide as a selective aerosol bronchodilator.

The present invention comprises 2-descarboxy-2-substituted-ω-pentanorprostaglandins, and their $C_{15}$ epimers, having at the 15-position one hydroxyl substituent, one hydrogen atom or alkyl substituent having from 5 to 11 carbon atoms, and the $C_9$, $C_{11}$, and $C_{15}$ esters thereof wherein said esterifying group is formyl, alkanoyl, having from 2 to 5 carbon atoms, or benzoyl; said 2-substituent having the formula:

Wherein R is akanoyl having from 2-8 carbon atoms or cycloalkanoyl having from 4 to 8 carbon atoms; aryoyl or substituted aryoyl of from 7 to 11 carbon atoms wherein said substituent is methyl, halogen, or methoxy; alkylsulfonyl of from 1 to 7 carbon atoms; arylsulfonyl or substituted arylsulfonyl wherein said substituent is methyl, halogen, or methoxy.

Preferred compounds are 2-descarboxy-2-substituted-ω-pentanorprostaglandins of the A, E, or F series, and their $C_{15}$ epimers, having at the 15-position one hydroxyl substituent, one hydrogen atom or alkyl substituent having from 1 to 3 carbon atoms and one alkyl substituent having from 5 to 11 carbon atoms, and the $C_9$, $C_{11}$, and $C_{15}$ esters thereof wherein said esterifying group is formyl, alkanoyl having from 2 to 5 carbon atoms, or benzoyl; said 2-substituent having the formula:

wherein R is alkanoyl having from 2–8 carbon atoms, cycloalkanoyl having from 4–8 carbon atoms; aryoyl or substituted aryoyl of from 7 to 11 carbon atoms wherein said substituent is methyl, halogen, or methoxy, alkylsulfonyl of from 1 to 7 carbon atoms; arylsulfonyl or substituted arylsulfonyl wherein said substituent is methyl, halogen, or methoxy.

Especially preferred compounds are those of the formulae:

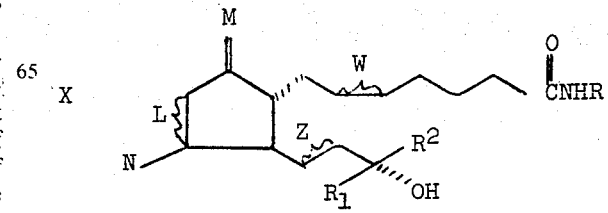

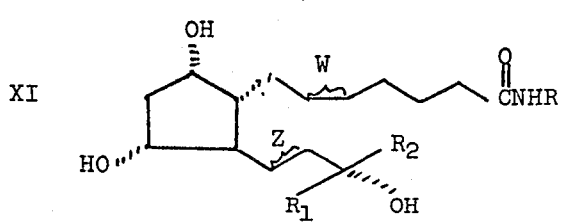

XI

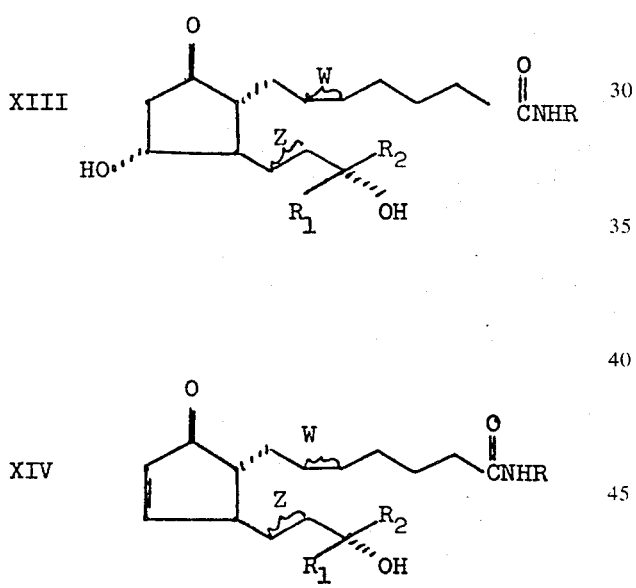

XII

XIII

XIV wherein R is alkanoyl having from 2–8 carbon atoms, cycloalkanoyl having from 4–8 carbon atoms; aryoyl or substituted aryoyl of from 7 to 11 carbon atoms wherein said substituent is methyl, halogen, or methoxy; alkylsulfonyl of from 1 to 7 carbon atoms; arylsulfonyl or substituted arylsulfonyl wherein said substituent is methyl, halogen, or methoxy;

$R_1$ is hydrogen or alkyl having from 1 to 3 carbon atoms;

$R_2$ is alkyl having from 5 to 11 carbon atoms;

W and L are each a single bond or cis double bond;

Z is single bond or trans double bond;

M is keto,

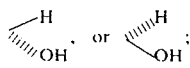

N is hydrogen or α-hydroxyl;

Wherein L, M and N are so selected as to complete the structure of a prostaglandin of the A, E or F series; and the $C_9$, $C_{11}$, and $C_{15}$ esters thereof wherein said esterifying group is formyl, alkanoyl, having from 2 to 5 carbon atoms, or benzoyl.

Especially preferred novel prostaglandins include those wherein:

R is acetyl, $R_1$ is hydrogen, $R_2$ is n-pentyl, W is a cis double bond, and Z is a trans double bond;

R is propionyl, $R_1$ is hydrogen, $R_2$ is n-pentyl, W is a cis double bond, an Z is a trans double bond;

R is cyclopropylcarbonyl, $R_1$ is hydrogen, $R_2$ is n-pentyl, W is a cis double bond, and Z is a trans double bond;

R is pivaloyl, $R_1$ is hydrogen, $R_2$ is n-pentyl, W is a cis double bond, and Z is a trans double bond;

R is methanesulfonyl, $R_1$ is hydrogen, $R_2$ is n-pentyl, W is a cis double bond, and Z is a trans double bond;

R is acetyl, $R_1$ is hydrogen, $R_2$ is 1,1-dimethylpent-1-yl, W is a cis double bond, and Z is a trans double bond;

R is methanesulfonyl, $R_1$ is hydrogen, $R_2$ is 1,1-dimethylpent-1-yl, W is a cis double bond, and Z is a trans double bond; and R is methanesulfonyl, $R_1$ is methyl, $R_2$ is n-pentyl, W is a cis double bond, and Z is a trans double bond.

R is 2-thiophenesulfonyl, $R_1$ is hydrogen, $R_2$ is n-pentyl, W is a cis double bond, and Z is a trans double bond;

R is methanesulfonyl, $R_1$ is hydrogen, $R_2$ is n-pentyl, W is a single bond, and Z is a trans double bond; and R is acetyl, $R_1$ is hydrogen, $R_2$ is n-pentyl, W is a single bond, and Z is a trans double bond.

Novel reagents and intermediates of the formulae below also comprise a portion of this invention.

II 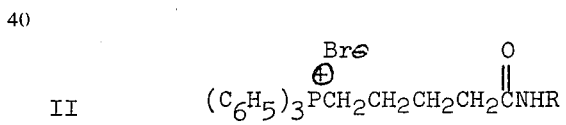

IX 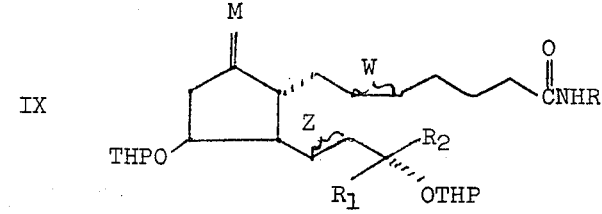

and

XXI 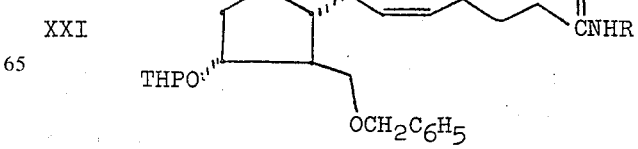

wherein R is alkanoyl having from 2–8 carbon atoms or cycloalkanoyl having from 4 to 8 carbon atoms; aryoyl or substituted aryoyl of from 7 to 11 carbon atoms wherein said substituent is methyl, halogen, or methoxy; alkylsulfonyl of from 1 to 7 carbon atoms; arylsulfonyl or substituted arylsulfonyl wherein said substituent is methyl, halogen, or methoxy;

$R_1$ is hydrogen or alkyl having from 1 to 3 carbon atoms;
$R_2$ is alkyl having from 5 to 11 carbon atoms;
W is a single bond or cis double bond;
Z is single bond or trans double bond;
M is keto,

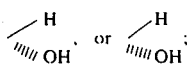

and THP is 2-tetrahydropyranyl.

For convenience, the novel prostaglandin analogs of this invention are herein referred to as prostaglandin carboxamides or PGA-, E-, $F_2\alpha$ -, etc. carboxamides, no matter what the R substituent is, so long as it agrees with the definition given above.

DETAILED DESCRIPTION OF THE INVENTION

For the first step in the preparation of the above named prostaglandin analogs, the appropriate hemiacetal precursor is caused to react with the disodium salt of a novel substituted carboxamide butyltriphenylphosphonium bromide in a molar ratio of from about 1:2 to 1:10. Such precursors are exemplified as follows:

2-[5α-hydroxy-3α-(tetrahydropyran-2-yloxy)-2β-(3α-(tetrahydropyran-2-yloxy)-trans-1-octen-1-yl)cyclopent-1α-yl]acetaldehyde, γ-hemiacetal for $PGF_1\alpha$ , $PGE_1$, $PGA_1$, $PGF_2\alpha$ , $PGE_2$, $PGA_2$, 13,14-dihydro-$PGF_1$ , $PGE_1$, and $PGA_1$;

2-[5α-hydroxy-3α-(tetrahydropyran-2-yloxy)-2β-(3β-lower alkyl-3α-(tetrahydropyran-2-yloxy)-trans-1-octen-1-yl)cyclopent-1α-yl]acetaldehyde, γ-hemiacetal for the 15-lower alkyl derivatives of these same prostaglandins;

2-[5α-hydroxy-3α-(tetrahydropyran-2-yloxy)-2β-(3α-(tetrahydropyran-2-yloxy)oct-1-yl)cyclopent-1α-yl]acetaldehyde, γ-hemiacetal for 13,14-dihydro $PGF_2\alpha$ , $PGE_2$, and $PGA_2$;

2-[5α-hydroxy-3α-(tetrahydropyran-2-yloxy)-2β(3β-lower alkyl-3α-(tetrahydropyran-2-yloxy)-oct-1-yl)cyclopent-1α-yl]acetaldehyde, γ-hemiacetal for 15-lower alkyl derivatives of 13,14-dihydro $PGF_2\alpha$ , $PGE_2$, and $PGA_2$; and 2-[5α-hydroxy-3α-(tetrahydropyran-2-yloxy)-2β-(3α-(tetrahydropyran-2-yloxy)-cis-5-trans-1-octadien-1-yl)cyclopent-1α-yl]acetaldehyde, γ-hemiacetal for $PGF_3\alpha$ and $PGE_3$.

The reaction will preferably be carried out at temperatures of about 25°–65°C. in an inert solvent such as dimethylsulfoxide and in an inert atmosphere, for a period of up to about 4 hours or until the reaction is essentially complete The substituted carboxamide-containing intermediates produced in the first step, as described above, may be converted by published procedures (Corey, et al. J. Am. Chem. Soc., 93. 1490 (1971) to the substituted carboxamide analogs of any of the prostaglandins listed above. These procedures are further described in detail in the appended examples and the steps entailed are summarized in the reaction schemes A and B below, wherein R has the significance previously described.

It will be understood that "alkyl", as used herein, includes branched forms as well as straight chain alkyl radicals.

REACTION SCHEME A

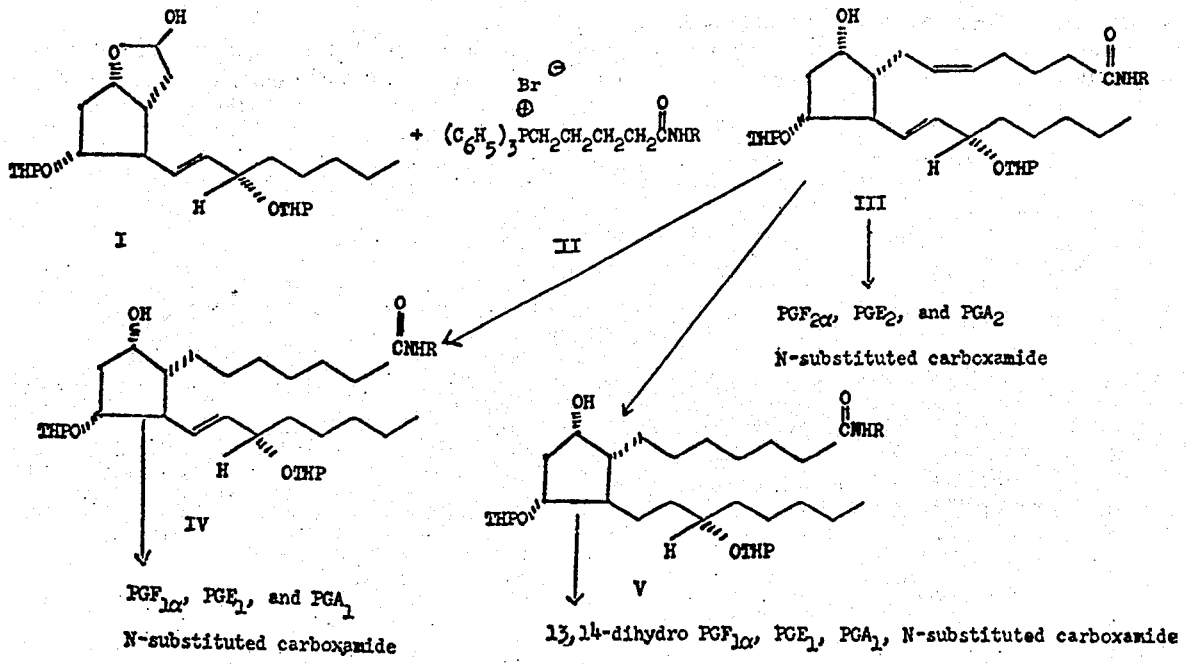

REACTION SCHEME B

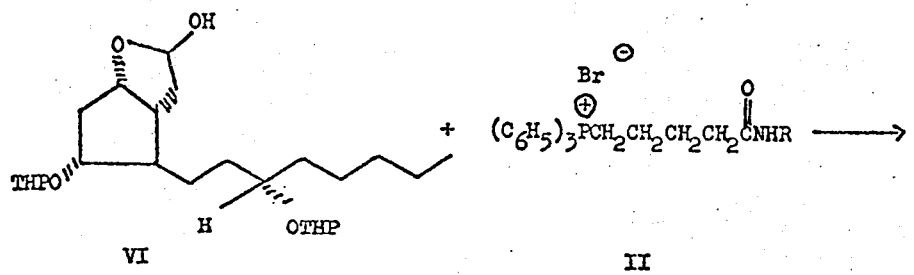

VI            II

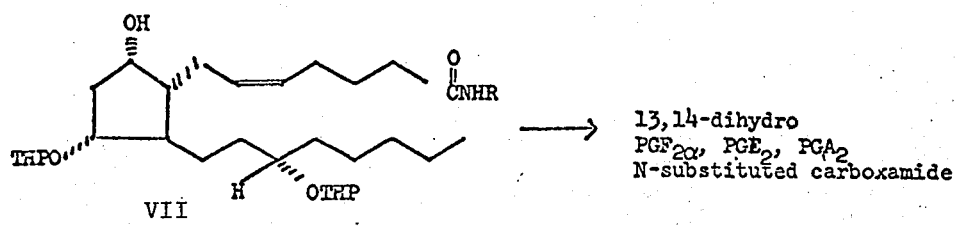

VII   →   13,14-dihydro PGF$_{2\alpha}$, PGE$_2$, PGA$_2$ N-substituted carboxamide As shown in Reaction Scheme A, Hemiacetal I is caused to react with the novel reagent II to produce III, the N-substituted carboxamide analog of the bis-THP ether of PGF$_{2\alpha}$.

III → PGF$_{2\alpha}$ -N-substituted carboxamide involves hydrolysis with aqueous acetic acid, concentration, and purification by column chromatography.

III → PGE$_2$-N-substituted carboxamide requires treatment with Jones reagent to form a second intermediate before the acid treatment and purification as above.

PGF$_{2\alpha}$ -N-substituted carboxamide is obtained by treating PGE$_2$-N-substituted carboxamide with sodium borohydride, hydrolysis, concentration, and purification by column chromatography.

PGA$_2$-N-substituted carboxamide is obtained by treating PGE$_2$-N-substituted carboxamide with formic acid, or dicyclohexylcarbodiimide and cupric chloride, concentration, and purification by column chromatography.

III → PGF$_{1\alpha}$ -N-substituted carboxamide requires a selective reduction with palladium on carbon and methanol to produce IV which may then be hydrolysed with aqueous acetic acid, and purified as above.

III → PGE$_1$-N-substituted carboxamide PGA$_1$-N-substituted carboxamide follows exactly the same method as outlined for the PGE$_2$-PGA$_2$ series above.

III → 13,14-dihydro PGF$_{1\alpha}$ N-substituted carboxamide require a reduction with palladium on carbon and methanol to produce V which is then hydrolysed with aqueous acetic acid, and purified as above.

To produce the other 13,14-dihydro derivatives one follows the procedures outlined above. Alternatively the PGE$_2$ or PGF$_{2\alpha}$ -N-substituted carboxamides may be reduced with palladium on carbon in methanol to produce the 13,14-dihydro PGE$_1$ or 13,14-dihydro PGF$_{1\alpha}$ -N-substituted carboxamides.

Referring now to Reaction Scheme B, Hemiacetal VI is caused to react with the novel reagent II to produce VII, the N-substituted carboxamide analog of the bis-THP ether of 13,14-dihydro PGF$_{2\alpha}$.

VII → 13,14-dihydro PGF$_{2\alpha}$ -N-substituted carboxamide involves hydrolysis with aqueous acetic acid, concentration, and purification by column chromatography.

VII → 13,14-dihydro PGE$_2$-N-substituted carboxamide requires treatment with Jones reagent to form a second intermediate before acid treatment and purification as above.

To obtain 13,14-dihydro PGF$_{2\beta}$ -N-substituted carboxamide, one follows the sequence above for PGE$_2$ → PGF$_{2\beta}$.

13,14-dihydro PGA$_2$ is obtained by treating 13,14-dihydro PGE$_2$-N-substituted carboxamide with formic acid, concentrating, and purifying by column chromatography.

To produce the 15-lower alkyl derivatives of all of the above mentioned prostaglandin N-substituted carboxamides, one merely employs hemiacetal I or hemiacetal VI with a lower alkyl moiety in the 15-position and proceeds as above to produce the desired compound.

To produce PGF$_{3\alpha}$ and PGE$_3$ N-substituted carboxamide, hemiacetal VIII is employed as the starting material and all of the other reaction steps are identical to those given above.

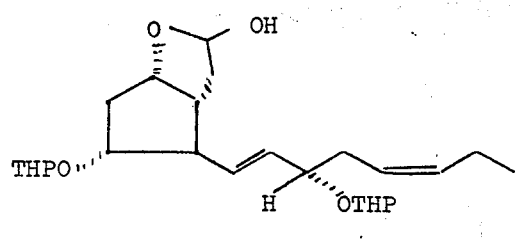

VIII

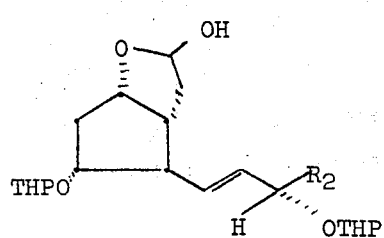

VIIIa

To produce homo derivatives including 16,16-dimethyl analogs of all the above prostaglandin N-substituted carboxamides one merely employs the appropriate hemiacetal, exemplified by VIIIa where $R_2$ is previously defined.

To produce the 15-epimeric, 15-lower alkyl derivatives, or 15-epimeric-15-lower alkyl derivatives of all of the above mentioned prostaglandin carboxamide, one merely employs hemiacetal VIIIb and XV-XIX, and proceeds as above to produce the desired compound.

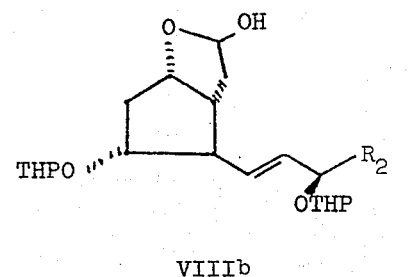

VIIIb

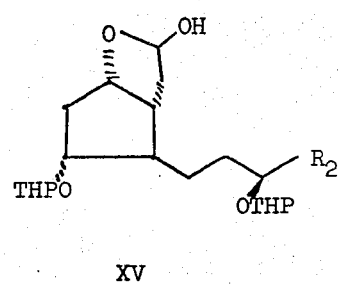

XV

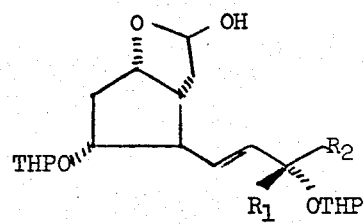

XVI

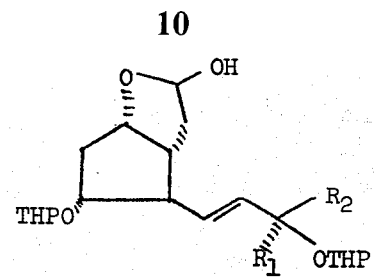

XVII

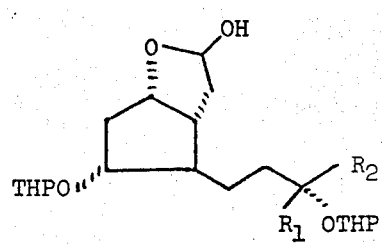

XVIII

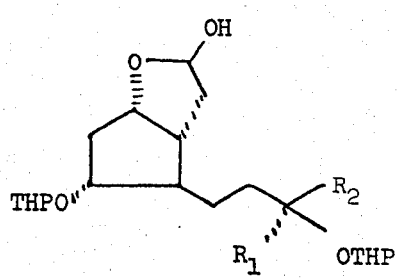

XIX

The novel alkanoates, formates, and benzoates of the E, F, and A series of prostaglandin carboxamides are prepared by reaction of the desired prostaglandin with an acid chloride. For example, $PGE_2$ acetylcarboxamide when reacted with benzoyl chloride in the presence of an amine in a reaction inert solvent, will yield 11,15-dibenzoyl-$PGE_2$ acetylcarboxamide and, in the same way, $PGF_{2\alpha}$ pivaloyl-carboxamide when reacted with pivaloyl chloride will yield 9,11,15-tripivaloyl $PGF_{2\alpha}$ pivaloylcarboxamide. An appropriate amine is pyridine and an appropriate solvent is methylene chloride.

Scheme C

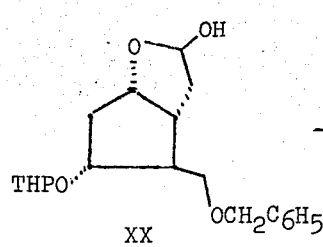 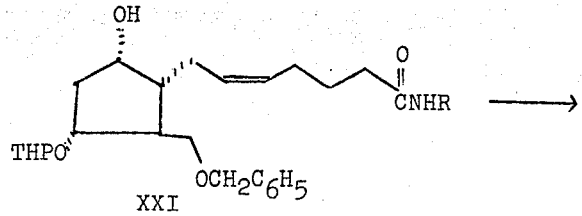

XX     XXI

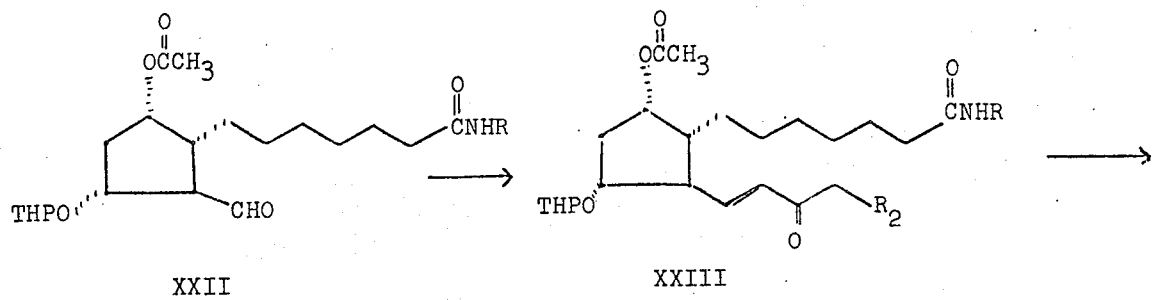

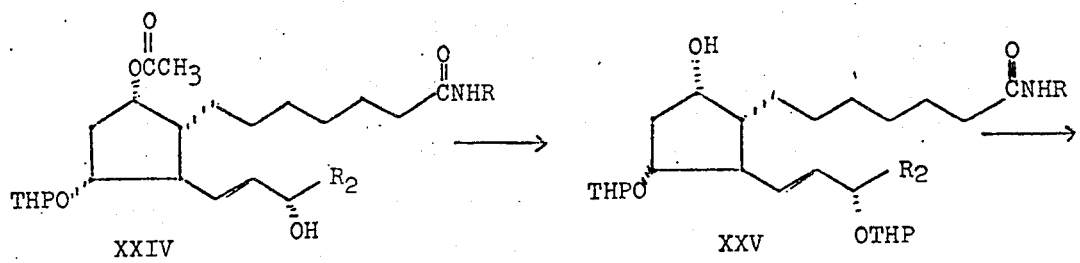

PGF$_{1\alpha}$, PGE$_1$, and PGA$_1$ N-substituted carboxamides.

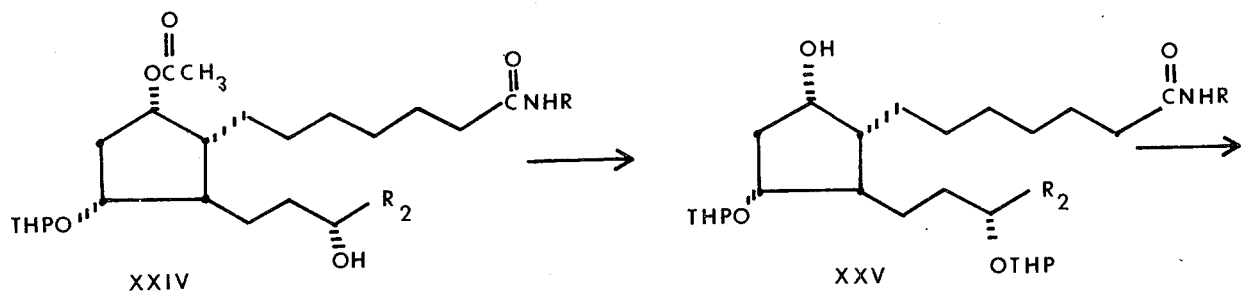

PGF$_{1\alpha}$, PGE$_1$, and PGA$_1$ N-substituted carboxamides.

The above named N-substituted prostaglandin carboxamides of the "one" series may be prepared by the synthetic route outlined in Scheme C. In the first step the hemiacetal XX is caused to react with the novel reagent II to produce the novel intermediate XXI.

XXI → XXII involves treatment with acetic anhydride and pyridine; followed by reduction with palladium in carbon in ethanol:acetic acid; followed by oxidation with dimethyl sulfoxide, dicyclohexylcarbodiimide, and pyridinium trifluoroacetate.

XXII → XXIII involves treatment with the sodium or lithium salt of the appropriately 2-substituted dimethyl-2-oxo-ethyl phosphonate and purification by column chromatography.

XXIII → XXIV involves reduction with zinc borohydride or lithium triethylborohydride, hydrolysis, and separation of the C$_{15}$ epimers by column chromatography.

XXIV → XXV involves treatment with dihydropyran with an acid catalyst followed by mild aqueous base hydrolysis.

XXV → PGF$_{1\alpha}$, PGE$_1$, and PGA$_1$ N-substituted carboxamides follow exactly the same method as outlined for the PGF$_{2\alpha}$, PGE$_2$, PGA$_2$ series above.

Alternatively, the above named N-substituted prostaglandin carboxamides may be prepared as exemplified below. Treatment of the known carboxylic acid intermediates XXVI, XXVII, and XXVIII with the appropriately substituted isocyanate in the presence of an amine such as triethylamine provides the novel intermediates III, IV, and VI prepared above. Conversions of these novel intermediates into the corresponding N-substituted prostaglandin carboxamides follow exactly the same methods described above.
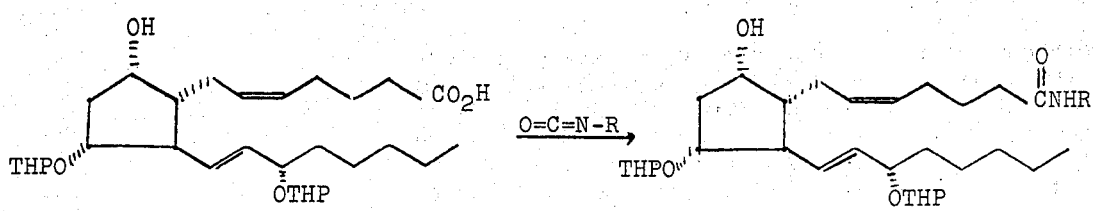
XXVI → III
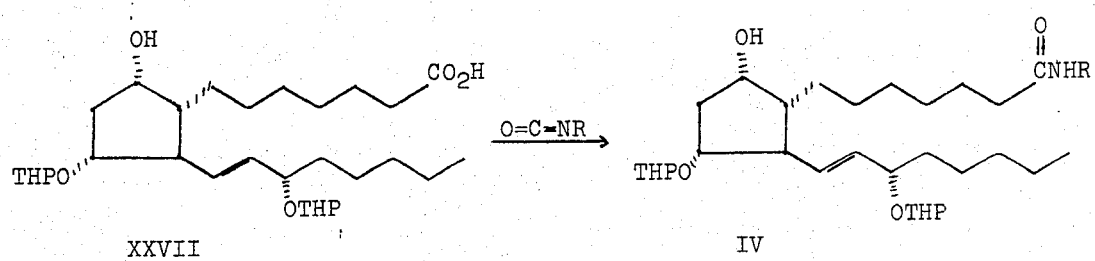
XXVII → IV
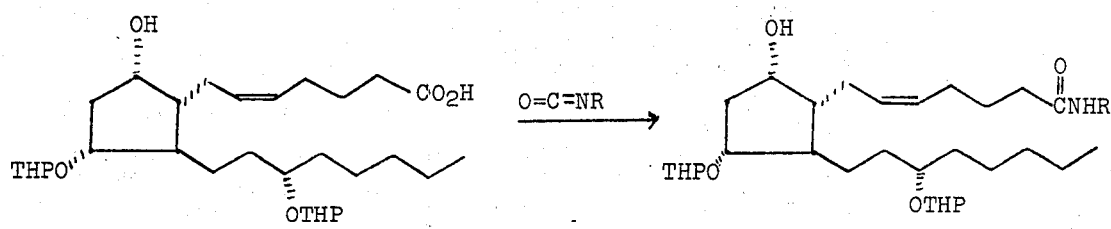
XXVIII → VII
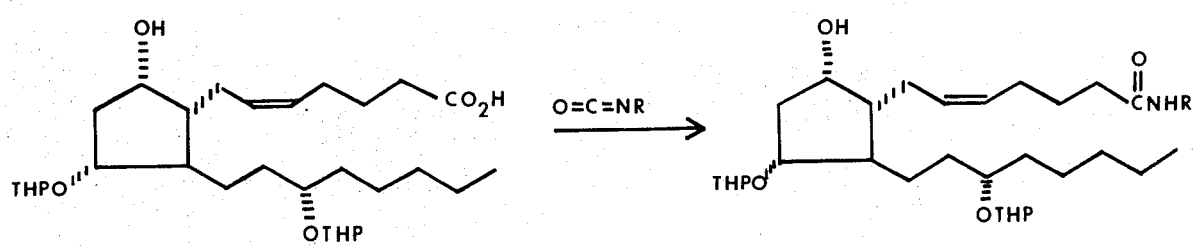
XXVIII → VII In numerous in vivo and in vitro tests we have demonstrated that the prostaglandin N-substituted carboxamide analogs possess the same physiological activities as exhibited by the natural prostaglandins. These tests include, among others, a test for effect on isolated smooth muscle from guinea pig uterus, gerbil colon, guinea pig ileum and rat uterus, inhibition of histamine induced bronchospasm in guinea pig, effects on dog blood pressure, and prevention of fertility in hamsters.

The physiological responses observed in these tests are useful in predicting potential utility of the test substance for the treatment of various natural and pathological conditions. The potential utility is magnified when the test substance exhibits a selective activity profile compared with the natural prostaglandins $E_2$ and $F_{2\alpha}$ (see Table I below).

For example, the N-acetyl 13,14-dihydroprostaglandin $E_1$ carboxamide and the N-acetyl prostaglandin $A_2$ carboxamide exhibited equipotent hypotensive effects in dogs with a longer duration of action than $PGE_2$. Furthermore the spasmogenic effects on the various smooth muscle preparations were significantly less for the N-acetyl 13,14-dihydroprostaglandin $E_1$ carboxamide or the N-acetyl $PGA_2$ carboxamide than those for $PGE_2$. Thus the N-acetyl 13,14-dihydroprostaglandin $E_1$ carboxamide and the N-acetyl $PGA_2$ carboxamide display superior potential to $PGE_2$ as a selective hypotensive agent.

TABLE I

| | Compound Tested Prostaglandin | R | Threshold Doses for Spasmogenic Effect on Isolated Smooth Muscle ng/ml. | | | |
|---|---|---|---|---|---|---|
| | | | Rat Uterus | Guinea Pig Uterus | Guinea Pig Ileum | Gerbil Colon |
| 1. | $PGE_2$ | — | 10–30 | 0.1–1.0 | 10–30 | 10–30 |
| 2. | $PGF_2\alpha$ | — | 10–30 | 1–10 | 10–30 | 25–50 |
| 3. | $PGE_2$ | Acetyl | 500–1000 | 3 | 100–500 | ≥1000 |
| 4. | 13,14-dihydro $PGE_1$ | Acetyl | >1000 | — | ≥1000 | >1000 |
| 5. | $PGF_2\alpha$ | Acetyl | 1000–3000 | 30–100 | 600–1000 | — |
| 6. | $PGA_2$ | Acetyl | — | — | — | — |
| 7. | $PGE_2$ | Propionyl | 1000 | 1 | 10 | — |
| 8. | $PGE_2$ | Cyclopropylcarbonyl | 250–500 | — | 500 | — |
| 9. | $PGF_2\alpha$ | Cyclopropylcarbonyl | 1000 | — | 1000 | — |
| 10. | $PGE_2$ | Pivaloyl | 50–100 | 1–3 | 500 | — |
| 11. | $PGE_2$ | Methanesulfonyl | 10–30 | 3–6 | 30–60 | 30–60 |
| 12. | $PGF_2\alpha$ | Methanesulfonyl | ≥1000 | 1000 | ≥1000 | ≥1000 |
| 13. | $PGE_2$ | p-toluenesulfonyl | 100–500 | — | >1000 | — |
| 14. | $PGF_2\alpha$ | p-toluenesulfonyl | 100 | — | >1000 | — |
| 15. | $PGE_2$ | benzenesulfonyl | 100–300 | — | 100 | — |
| 16. | $PGF_2\alpha$ | benzenesulfonyl | 100 | — | 100 | — |
| 17. | $PGE_0$ | methanesulfonyl | — | 100–300 | 30–100 | — |
| 18. | 15-methyl $PGE_2$ | methanesulfonyl | 100–300 | 0.3–1 | 30 | — |
| 19. | $PGE_2$ | 2-Thiophenesulfonyl | — | 600–1000 | 60–100 | — |
| 20. | $PGF_2\alpha$ | 2-Thiophenesulfonyl | — | 600–1000 | 600–1000 | — |
| 21. | $PGF_2\beta$ | Methanesulfonyl | 1000 | 3–10 | 1000 | — |
| 22. | 16,16-dimethyl $PGE_2$ | Methanesulfonyl | 30 | 0.3 | — | — |
| 23. | 16,16-dimethyl $PGE_2$ | Acetyl | 300–1000 | 0.3 | — | — |

| | Compound Tested* | Histamine Induced Bronchospasm in guinea pig % Protection by 100 μg/ml. Aerosol dose | Threshold Dose for Effect on Anesthesized Dog Blood Pressure g/kg i.v. (−) — depressor (+) — pressor | Relative Potency ($PGE_2 = 100$) for Inducing diarrhea in Mice [$ED_{50}$ for $PGE_2 = 0.5$ mg/kg i.v.] |
|---|---|---|---|---|
| | Prostaglandin | | | |
| 1. | | 75–85 | 0.16 (−) | 100 |
| 2. | | — | 1,2,4 (+) 10 (−) | 10 |
| 3. | | 65–75 | 0.16 (−) | 150 |
| 4. | | 30–35 | 0.08 (−) | — |
| 5. | | — | — | 80 |
| 6. | | — | 0.1 (−) | |
| 7. | | 74 | — | |
| 8. | | 59 | 10 (+) | |
| 9. | | — | 10 (+) | |
| 10. | | 0 | No response at doses ≤ 20 | |
| 11. | | 0 | 10 (−) | 10–20 |
| 12. | | — | No response at doses ≤ 20 | 33 |
| 13. | | 19 | No response at doses ≤ 20 | |
| 14. | | — | No response at dose ≤ 20 | |
| 15. | | 0 | No response at doses ≤ 20 | |
| 16. | | — | No response at doses ≤ 10 | |
| 17. | | 0 | — | — |
| 18. | | 43 | — | 900 |
| 19. | | 0 | — | — |
| 20. | | — | — | — |
| 21. | | 0 | No response at doses ≤ 40 | No response at 1 mg. |
| 22. | | 28 | 4.0 | 2700 |
| 23. | | 24 | No response at doses ≤ 20 | 1100 |

*Numbers of compounds and R substituents correspond to those on page 18

The N-acetyl prostaglandin $E_2$ carboxamide, N-propionoyl prostaglandin $E_2$, and the N-cyclopropylcarbonyl prostaglandin $E_2$ carboxamide exhibited similar potency to $PGE_2$ (70 and 59 vs. 80%) in protecting guinea pigs against histamine-induced bronchospasm. These carboxamide analogs, however, exhibited significantly smaller spasmogenic effects in various smooth muscle preparations than $PGE_2$. Furthermore, the N-acetyl prostaglandin $E_2$ carboxamide and N-cyclopropylcarbonyl prostaglandin $E_2$ carboxamide were markedly less potent than $PGE_2$ in lowering blood pressure in guinea pig and dog respectively. Accordingly the compounds are more selective bronchodilators than and cause less undesirable side effects than the natural prostaglandins.

The N-trimethylacetyl prostaglandin $E_2$ arboxamide, the N-methanesulfonyl prostaglandin $E_2$ carboxamide, and the N-p-toluenesulfonyl prostaglandin $F_{2\alpha}$ carboxamide all exhibited spasmogenic effects on the estrogenized rat uterus of comparable potency to those of $PGE_2$. In comparison, these carboxamide analogs were significantly less potent than $PGE_2$ in other smooth muscle preparations, on effects on dog blood pressure, and in protecting against histamine induced bronchospasm in the guinea pig. The biological profiles displayed by the N-trimethylacetyl prostaglandin $E_2$ carboxamide, the N-methanesulfonyl prostaglandin $E_2$ carboxamide, and the N-p-toluenesulfonyl prostaglandin $F_{2\alpha}$ carboxamide indicate superior potential to $PGE_2$ as inducers of labor, abortefacients, and in the control of fertility, in that they are expected to produce a lower incidence of undesirable side effects than $PGE_2$. In vivo antifertility activity of a magnitude comparable to $PGE_2$ and $PGF_{2\alpha}$ was demonstrated both with N-methanesulfonyl prostaglandin $E_2$ carboxamide and N-methanesulfonyl prostaglandin $F_{2\alpha}$ carboxamide in rats. The fact that the latter compound exhibited insignificant uterine stimulant activity at the doses tested (Table I) suggests that its antifertility effects are due to a luteolytic mechanism of action not involving smooth muscle stimulation.

The new compounds of this invention can be used in a variety of pharmaceutical preparations which contain the compound or a salt thereof, and they may be administered by a variety of routes, such as intravenous, oral and topical including aerosol, intravaginal, and intranasal among others.

The natural prostaglandins are well known agents for the induction of abortion, and the N-substituted prostaglandin carboxamides of the E and F series share this utility. For such treatment an aqueous suspension of a substituted PGE-carboxamide or N-substituted PGF-carboxamide is administered at a level of from about 0.2–5.0 mg/dose for N-substituted PGE carboxamide or 30–50 mg/dose for N-substituted PGF carboxamide with from 1–7 oral doses per day being employed in either case.

If an intravaginal treatment for abortion induction is desired, a suitable agent is a sterile ethanolic solution of either of these two N-substituted prostaglandin carboxamides or lactose tablets of the same two agents. In such treatments suitable doses are from about 15–200 mg/dose for N-substituted PGE carboxamides or from about 35–500 mg/dose for N-substituted PGF carboxamides with 1 or 2 doses being employed.

In cases where a midterm abortion is necessary, an effective agent is an ethanol-dextrose solution of N-substituted $PGE_2$ carboxamide administered as an intravenous infusion. A suitable dosage is about 5–500 μg/min administered for a period of from about 1–48 hours. Alternatively for a midterm abortion, an effective agent is a ethanol-dextrose solution of N-substituted $PGF_{2\alpha}$ carboxamide administered as an intraamniotic injection. A suitable dosage is about 1–50 mg/injection with 1–12 doses being employed with an interval of 3–24 hours between doses. For extraamniotic, intrauterine administration doses of 0.1 to 5 mg of N-substituted $PGE_2$ carboxamide are injected up to 12 times over a 24 hour period.

Another use for the N-substituted prostaglandin carboxamides is as an inducer of labor. For this purpose an ethanol-saline solution of the $PGE_2$ analog is employed as an intravenous infusion in the amount of from about 3–100 μg/kg/min for from about 1–24 hours.

Another use for the N-substituted prostaglandin carboxamides is for fertility control. For this purpose a lactose tablet impregnated with a sterile 95% solution of the $PGE_2$ or $PGF_{2\alpha}$ is employed for intravaginal administration in the amount of 5–500 mg/dose with 1–2 doses being employed 2–7 days after the expected day of menstruation had passed.

Another known use for natural prostaglandins is as regulators of cardiac rhythm. The prostaglandin carboxamides, particularly those of the E series, share this property.

Perhaps the most important application for the N-substituted prostaglandin carboxamides, on the basis of the known uses of the natural prostaglandins, is to increase nasal patency or to produce bronchodilation. An appropriate dosage from for these uses is an aqueous ethanolic solution of N-acetyl $PGE_2$-carboxamide or a suspension employed as an aerosol using fluorinated hydrocarbons as propellant in the amount of from about 10–500 μg/dose, respectively.

N-Substituted PGA-carboxamides have utility in hypertension, for example the treatment of hypertensive crisis. For such treatment an ethanolic solution of the drug is administered as an intravenous infusion at about 1–30 μg/kg/min for a total dose of from about 1–40 mg/kg/day.

The 9, 11, and 15 alkanoates, formates, and benzoates of the PGE, A, and F carboxamides have the same utility as the non-esterified compounds. They often show a further reduction in undesirable side effects.

The 15-lower alkyl substituted PGE, A, and F carboxamides have the same utility as the unsubstituted prostaglandins but have a longer duration of action.

The PGFα carboxamides have the same utilities as the PGFα carboxamides; in addition to having applications as bronchodilators.

The novel prostaglandins with a β-OH at the 15-position are in general less potent, although frequently more selective than the corresponding α-hydroxyl epimers. Additionally, the prostaglandins having a β-hydroxyl at C-15 are valuable intermediates to prostaglandins having a α-hydroxyl at C-15 through a recycling process involving an oxidation and reduction at C-15.

To prepare any of the above dosage forms or any of the numerous other forms possible, various reaction-inert diluents, excipients or carriers may be employed. Such substances include, for example, water, ethanol, gelatins, lactose, starches, magnesium stearate, talc, vegetable oils, benzyl alcohols, gums, polyalkylene glycols, petroleum jelly, cholesterol, and other known carriers for medicaments. If desired these pharmaceutical compositions may contain auxiliary substances such as preserving agents, wetting agents, stabilizing agents, or other therapeutic agents such as antibiotics.

The following examples are merely illustrative, and in no way limit the scope of the appended claims. All temperatures are given in Centigrade and all melting and boiling points are uncorrected.

EXAMPLE I

A stirred solution of 100 g. (0.55 mole) of 5-bromovaleramide, 62.4 g. (0.61 mole) of acetic anhydride, and 5.4 g. (0.055 mole) of concentrated sulfuric was heated on a steam bath under nitrogen for 1.5 hours (internal temperature 93°). The mixture was then cooled to room temperature diluted with 250 ml. of water. The resultant tan granular precipitate was collected by filtration and dissolved in 600 ml. of methylene chloride. The solution was washed with saturated sodium bicarbonate (100 ml.) and saturated brine (100 ml.), was dried (anhydrous magnesium sulfate), treated with Darco, and filtered. Hexane was added to effect crystallization which afforded 64.8 g. (53.0% yield) of N-acetyl-5-bromovaleramide melting at 88°–90°.

The ir spectrum ($CHCl_3$) of the product exhibited absorption bands at 5.72 $\mu$ (moderately strong) 5.80 $\mu$ (strong) attributable to the carbonyl groups. The nmr spectrum ($CDCl_3$) showed a triplet centered at 3.46 $\delta$ (J = 6 cps) for $BrCH_2$—, a triplet centered at 2.63 $\delta$ (J = 6 cps) for

a singlet at 2.36 $\delta$ for

a multiplet at 1.67–2.17 $\delta$ for —$CH_2$—$CH_2$—, and a broad singlet at 9.00–9.58 $\delta 0$ for —N—H.

A solution of 50.5 g. (0.227 mole) of N-acetyl-5-bromovaleramide and 64.6 g. (0.274 mole) of triphenylphosphine in 250 ml. of xylene was heated at reflux under nitrogen for 4 hours then was let cool to room temperature. The xylene was decanted from the resulting oil which was recyrstallized from methylene chloride:ethyl acetate to afford colorless needles of [4-(acetylaminocarbonyl)butyl]triphenylphosphonium bromide weighing 50.2 g. (45.7% yield) melting at 164°–165°.

The ir spectrum ($CHCl_3$) of the product exhibited absorption bands at 5.72 $\mu$ (moderately strong) and 5.80 $\mu$ (strong) attributable to the carbonyl groups. The nmr spectrum ($CDCl_3$) exhibited a multiplet at 3.42-3.98 $\delta$ for the P—$CH_2$—, a multiplet at 2.44-2.96 $\delta$ for the

a singlet at 2.23 $\delta$ for the

a multiplet at 1.48–2.13 for the $CH_2CH_2$, and a multiplet at 7.60–8.14 $\delta$ for the aromatic protons.

The above product may be caused to react with the known 2-[5α-hydroxy-3α-(tetrahydropyran-2-yloxy)-2β-(3α-(tetrahydropyran-2-yloxy)-trans-1-cis-5-octadien-1-yl)cyclopent-1α-yl]acetaldehyde, γ-hemiacetal (E. J. Corey, et al., J. Am. Chem. Soc., 93, 1490 (1971) to product N-acetyl-9α-hydroxy-11α,15α-bis-(tetrahydropyran-2-yloxy)-cis-5-trans-13-cis-17-prostatrienamide which may be converted by known reactions (E. J. Corey, ibid) into the N-acetyl prostaglandin $F_{3\alpha}$ carboxamide or the N-acetyl prostaglandin $E_3$.

The above product may be caused to react with the mixed 2-[5α-hydroxy-3α-(tetrahydropyran-2-yloxy)-2β-(3β-methyl-3α-(tetrahydropyran-2-yloxy)oct-1-yl)cyclopent-1α-yl]acetaldehyde, γ-hemiacetal and 2-[5α-hydroxy-3α-(tetrahydropyran-2-yloxy)-2β-(3α-methyl-3α-(tetrahydropyran-2-yloxy)oct-1-yl)cyclopent-1α-yl]acetaldehyde, γ-hemiacetal, prepared in Example XXVIII to produce the epimeric N-acetyl-9α-hydroxy-11α,15-bis-(tetrahydropyran-2-yloxy)-15-methyl-trans-13-prostenamides called Compounds A. Compound A may be hydrolyzed as described in Example III to produce the N-acetyl-15-methyl-13,14-dihydro-prostaglandin $F_{2\alpha}$ carboxamides (which may be subjected to catalytic hyrogenation as described in Example VII to produce N-acetyl 15-methyl-13,14-dihydroprostaglandin $F_{1\alpha}$ carboxamides). Compound A may be subjected to oxidation as described in Example IV followed by hyrolysis as described in Example V to produce N-acetyl 15-methyl 13,14-dihydro prostaglandin $E_2$ carboxamides called Compound B. Compound B may be dehydrated as described in Example VI to produce N-acetyl 15 -methyl-13,14-dihydroprostaglandin $A_2$ carboxamides. Compound B may be catalytically hydrogenated as described in Example VII to produce N-acetyl 15-methyl-13,14-dihydro-prostaglandin $E_1$ carboxamides which may be dehydrated as described in Example VI to produce N-acetyl 15-methyl-13,14-dihydroprostaglandin $A_1$ carboxamides. Compound B may also be reduced as described in Example XXXVI to produce N-acetyl 15-methyl-13,14-dihydroprostaglandin $F_{2\beta}$.

The above product may be caused to react with the 2-[5α-hydroxy-3α-(tetrahydropyran-2-yloxy)-2β-(3α-(tetrahydropyran-2-yloxy)oct-1-yl)cyclopent-1α-yl]acetaldehyde, γ-hemiacetal (prepared in Example XXVII) to produce N-acetyl-9α-hydroxy-11α,15α-bis-(tetrahydropyran-2-yloxy)-cis-5-prostenamide called Compound C. Compound C may be hydrolyzed as described in Example III to produce the N-acetyl 13,14-dihydroprostaglandin $F_2$ carboxamide. Compound C may be subjected to oxidation as described in Example IV followed by hydrolysis as described in Example V to produce the N-acetyl 13,14-dihydroprostaglandin $E_2$ carboxamide. The latter may be dehydrated as described in Example VI to produce the N-acetyl 13,14-dihydroprostaglandin $A_2$ carboxamide, or reduced as described in Example XXXVI to produce the N-acetyl-13,14-dihydroprostaglandin $F_{2\beta}$.

The above product may be caused to react with the known 2-[5α-hydroxy-3α-(tetrahydropyran-2-yloxy)-2β-(3β-(tetrahydropyran-2-yloxy)oct-1-yl)cyclopent-1α-yl]acetaldehyde, γ-hemiacetal to produce N-acetyl-9α-hydroxy-11α,15α-bis(tetrahydropyran-2-yloxy)-cis-5-prostenamide called Compound D. Compound D may be hydrolyzed as described in Example III to produce the N-acetyl 15-epi-13,14-dihydroprostaglandin $F_{2\alpha}$ carboxamide. Compound D may be subjected to oxidation as described in Example Iv followed by hydrolysis as described in Example V to produce the N-acetyl 15-epi-13,14-dihydroprostaglandin $E_2$ carboxamide. The latter may be dehydrated as described in Example VI to produce the N-acetyl 15-epi-13,14-dihydroprostaglandin $A_2$ carboxamide or reduced as described in Example XXXVI to produce the N-acetyl 15-epi-13,14-dihydroprostaglandin $F_{2\beta}$.

The above product may be caused to react with the 2-[5α-hydroxy-3α-(tetrahydropyran-2-yloxy)-2β-(3β-(tetrahydropyran-2-yloxy)-1-trans-octen-1-yl)cyclopent-1α-yl]acetaldehyde, γ-hemiacetal prepared in Example XXIv to produce N-acetyl-9α-hydroxy-11α,15β-bis-(tetrahydropyran-2-yloxy)-cis-5-trans-13-prostadienamide called Compound E. Compound E may be hydrolyzed as described in Example III to produce the N-acetyl 15-epi-prostaglandin $F_{2\alpha}$ carboxamide. Compound E may be subjected to oxidation as described in Example Iv followed by hydrolysis as described in Example V to produce the N-acetyl 15-epi-prostaglandin $E_2$ carboxamide. The latter may be dehydrated as described in Example VI to produce the N-acetyl 15-epi-prostaglandin $A_2$ carboxamide or reduced as described in Example XXXVI to the N-acetyl 15-epi-prostaglandin $F_{2\beta}$ carboxamide.

The above product may be caused to react with the 2-[3α,5α-dihydroxy-2β-(3α-hydroxy-oct-1-yl)cyclopent-1α-yl)cyclopent-1α-yl]acetaldehyde, γ-hemiacetal prepared in Example XXVI to provide the N-acetyl 13,14-dihydroprostaglandin $F_{2\alpha}$ carboxamide.

The above product may be caused to react with the 2-[3α,5α-dihydroxy-2β-(3β-hydroxy-trans-1-octen-1-yl)cyclopent-1α-yl]acetaldehyde, γ-hemiacetal prepared in Example XXI to provide the N-acetyl 15-epi prostaglandin $F_{2\alpha}$ carboxamide.

The above product may be caused to react with the 2-[3α,5α-dihydroxy-2β-(3β-hydroxyoct-1-yl)cyclopent-1α-yl]acetaldehyde, γ-hemiacetal prepared in Example XXI to provide the N-acetyl 15-epi-13,14-dihydroprostaglandin $F_{2\alpha}$.

The above product may be caused to react with the 2-[3α,5α-dihydroxy-2β-(3α-hydroxy-3β-methyl-trans-1-octen-1-yl)cyclopent-1α-yl]acetaldehyde, γ-hemiacetal prepared in Example XXXVII to provide the N-acetyl 15-methyl-prostaglandin $F_{2\alpha}$ carboxamide.

The above product may be caused to react with the 2-[3α,5α-dihydroxy-2β-(3α-hydroxy-3β-methyl-oct-1-yl)cyclopent-1α-yl]acetaldehyde, γ-hemiacetal prepared in Example XXXVII to provide the N-acetyl 15-methyl-13,14-dihydroprostaglandin $F_{2\alpha}$.

EXAMPLE II

To a solution of 5.82 g. (12.0 mmoles) of the [4-(Acetylaminocarbonyl)butyl]triphenylphosphonium bromide in 6.0 ml. of dry dimethyl sulfoxide was added dropwise 9.8 ml. (23.5 mmoles) of a 2.4 M. solution of sodium methylsulfinylmethide in dimethyl sulfoxide. To this red ylide solution was added dropwise a solution of 1.32 g. (3.00 mole) of 2-[5α-hydroxy-3α-(tetrahydropyran-2-yloxy)-2β-(3α-(tetrahydropyran-2-yloxy)-trans-1-octen-1-yl)cyclopent-1α-yl]acetaldehyde, γ-hemiacetal in 3.0 ml. of dry dimethyl sulfoxide over a period of 0.5 hour. After being stirred for 20 hours at room temperature the reaction was poured onto ice water. The aqueous solution was covered with ether and the vigorously stirred mixture was acidified to pH 3 by the addition of 10% aqueous hydrochloric acid. The acidified aqueous layer was further extracted with ether (2×). The combined ethereal extracts were dried (anhydrous magnesium sulfate) and were concentrated to afford a semisolid weighing 4.0 g. This semisolid was purified by column chromatography on silica gel (Baker "Analyzed" Reagent 60–200 mesh) using chloroform and then ethyl acetate as eluents. After removal of high $R_f$ impurities, 1.15 g. (67.8% yield) of N-acetyl-9α-hydroxy-11α,15α-bis(tetrahydropyran-2-yloxy)-cis-5-trans-13-prostadienamide were collected as a viscous, colorless oil.

The ir spectrum ($CHCl_3$) of the product exhibited a strong absorption at 5.80 μ (carbonyls). The nmr spectrum ($CDCl_3$) exhibited a multiplet at 5.27–5.68 δ for the olefinic protons, a broad singlet at 4.60–4.80 δ for OH and NH, multiplets at 3.25–4.30 δ for —CHO and —$CH_2O$—, a singlet at 2.37 δ for the —$COCH_3$, and multiplets at 0.68–2.37 δ for the remaining protons.

The above product may be subjected to carefully controlled catalytic reduction to produce N-acetyl-9α-hydroxy-11α,15α-bis(tetrahydropyran-2-yloxy)-trans-13-prostenamide which may be converted by known reactions (E. J. Corey, et al., J. Am. Chem. Soc., 92, 2586 (1970) to N-acetyl prostaglandin $F_1$ carboxamide and N-acetyl 15-methylprostaglandin $E_1$ carboxamide. The latter may be converted as described in Example VI to N-acetyl prostaglandin $A_1$ carboxamide or reduced as described in Example XXXVI to N-acetyl prostaglandin $F_{1\beta}$ carboxamide.

The above product may be subjected to catalytic reduction to produce the N-acetyl-9α-hydroxy-11α,15α-bis-(tetrahydropyran-2-yloxy)prostanamide called Compound A. Compound A may be hydrolyzed as described in Example III to produce the N-acetyl-13,14-dihydroprostaglandin $F_{1\alpha}$ carboxamide. Compound A may be subjected to oxidation as described in Example IV followed by hydrolysis as described in Example V to produce the N-acetyl-13,14-dihydroprostaglandin $E_1$ carboxamide called Compound B. Compound B may be dehydrated as described in Example VI to produce the N-acetyl-13,14-dihydroprostaglandin $A_1$ carboxamide or reduced as described in Example XXXVI to the N-acetyl-13,14-dihydroprostaglandin $F_{1\beta}$ carboxamide.

EXAMPLE III

A solution of 108 mg. (0.192 mmole) of the product of Example II in 2 ml. of a 65:35 mixture of acetic acid:water was stirred under nitrogen at 42° for 3 hours. The solvent was then removed under reduced pressure and the resultant oil was purified by column chromatography (Mallinckrodt CC-4) using chloroform, ethyl acetate, then a 9:1 mixture of methylene chloride-methanol as eluents. After removal of less polar impurities the N-acetyl 9α,11α,15α-hydroxy-5-cis-13-trans-prostadienamide was collected as a viscous, colorless oil weighing 42 mgs. (89% yield).

The nmr ($CDCl_3$) of the product exhibited a multiplet at 5.65-5.22 δ (4H) for the olefinic protons, a multiplet at 4.31–3.80 δ (3H) for the CHO, a broad singlet at 3.20–2.73 δ (4H) for the OH and NH, a singlet at 2.41 δ (3H) for the $COCH_3$, and multiplets at 2.60–0.71 δ (23H) for the remaining protons.

The above product may be hydrogenated as described in Example VII to the N-acetyl-13,14-dihydroprostaglandin $F_{1\alpha}$.

EXAMPLE IV

To a solution cooled to −10° under nitrogen of 1.15 g. (2.04 mmole) of the N-acetyl-9α-hydroxy-11α,15α-bis-(tetrahydropyran-2-yloxy)-cis-5-trans-13-prostadienamide prepared in Example II above in 30 ml. of reagent grade acetone was added dropwise 0.90 ml. of Jones' reagent. After 30 minutes the reaction was quenched by the addition of 0.90 ml. of isopropanol. The mixture was stirred in the cold for 10 minutes then was diluted with ethyl acetate. The organic layer was washed with water (2×) and saturated brine (1×), was dried (anhydrous magnesium sulfate), and was concentrated to afford the crude oily N-acetyl-9-oxo-11α,15α-bis-(tetrahydropyran-2-yloxy)-cis-5-trans-13-prostadienamide weighing 1.12 g. (97.5% yield).

The ir spectrum ($CHCl_3$) of the product exhibited a strong absorption at 5.67 μ (ketone carbonyl) and 5.95 μ (imide carbonyls).

A solution of 5.0 g. (8.89 mmoles) of the product of Example II, 5.45 g. (26.5 mmoles) of dicyclohexylcarbodiimide, and 1.71 g. (8.89 mmoles) of pyridinium trifluoroacetate in 75 ml. of benzene was stirred under nitrogen at room temperature for 4.0 hours. The solution then was diluted with ethyl acetate (150 ml.), the precipitated dicyclohexylurea was collected by filtration, the solution was washed with water (3×), and with saturated brine (1×), was dried (anhydrous magnesium sulfate), and was concentrated to afford the oily, crude N-acetyl-9-oxo-11α,15α-bis-(tetrahydropyran-2-yloxy)-cis-5-trans-13-prostadienamide weighing 6.56 g. (>100% yield).

EXAMPLE V

A solution of 1.12 g. (0.20 mmoles) of the N-acetyl-9-oxo-11α,15α-bis-(tetrahydropyran-2-yloxy)-cis-5-trans-13-prostadienamide of Example IV in 14.0 ml. of a 65:35 mixture of acetic acid:water was stirred under nitrogen at room temperature for 18 hours then was concentrated by rotary evaporation. The resultant crude oil was purified by column chromatography on silica gel (Mallinckrodt CC-7) using mixtures of chloroform ethyl acetate as eluent. After elution of less polar impurities the crystalline N-acetyl-9-oxo-11α,1-5α-dihydroxy-cis-5-trans-13-prostadienamide, the N-acetyl prostaglandin $E_2$ carboxamide, was collected weighing 407 mg. (51.8% yield) melting at 86°–86.5° from ethyl acetate:hexane.

The ir spectrum ($CHCl_3$) of the product exhibited strong absorptions at 5.78 μ (ketone carbonyl) and 5.92 μ (imide carbonyls). The nmr spectrum ($CDCl_3$) of the product exhibited two multiplets at 5.26–5.72 δ for the olefinic protons, a multiplet at 3.85–4.28 δ for the —CHO, a singlet at 2.35 δ for the —COCH$_3$, and multiplets at 0.68–2.82 δ for the remaining protons.

The above product may be reduced as described in Example XXXVI to the N-acetyl prostaglandin $F_{2\beta}$ carboxamide.

EXAMPLE VI

A solution of 32 mg. of the N-acetyl-9-oxo-11α,15α-dihydroxy-cis-5-trans-13-prostadienamide as prepared in Example V in 1.0 ml. of 97% formic acid was stirred under nitrogen at room temperature for 2.0 hours. The mixture was then concentrated (rotary evaporation followed by oil pump) to afford a pale-yellow, crude product which was purified by column chromatography on silica gel (SilicAR CC-4) using a 2:1 mixture of cyclohexane:ethyl acetate as eluent. The product, N-acetyl-9-oxo-15α-hydroxy-cis-5-$\Delta^{10}$-trans-13-prostatrienamide, the N-acetyl prostaglandin $A_2$ carboxamide, was collected as a colorless oil weighing 15 mg.

The ir spectrum ($CHCl_3$) of the product exhibited absorption bands at 1720 cm$^{-1}$ attributable to the carbonyl groups and 960 cm$^{-1}$ attributable to the trans double bond. The mass spectrum of the product exhibited a parent ion at 375 as well as an M-18 peak. Furthermore the uv spectrum (MeOH) after base treatment exhibited an absorption at 278 mμ.

EXAMPLE VII

A mixture of N-acetyl-9-oxo-11α,15α-dihydroxy-cis-5-trans-13-prostadienamide as prepared in Example V, (38 mg., 0.097 mmole), 5% palladium on carbon (12 mg.) and methanol (7 ml.) was stirred at room temperature under one atmosphere of hydrogen pressure for 90 minutes. The mixture was filtered to remove the catalyst, and the filtrate was concentrated to give a thick, clear, colorless oil (38 mg.). Chromatography of the oil on an acidic silica gel column (SilicAR CC-4) using chloroform followed by chloroform-methanol mixtures as eluent separated mixed fractions of the desired product and less polar impurities (23 mg.) from a fraction of the pure product, N-acetyl-9-oxo-11α,1-5α-dihydroxy-prostenamide, the N-acetyl 13,14-dihydroprostaglandin $E_1$ carboxamide, as white crystalline solid (13 mg., 34%), m.p. 67°–71°. The ir spectrum ($CHCl_3$) of the product exhibited sharp absorption bands at 1740 cm$^{-1}$ and 1705 cm$^{-1}$ (C=O), and broad bands at 3390 cm$^{-1}$ and 3600 cm$^{-1}$ (NH and OH). The absence of absorption in the 965 cm$^{-1}$ region of the spectrum indicated the absence of a trans double bond. The mass spectrum of the product exhibited significant peaks at m/e 379 (M$^+$—H$_2$O), 361 (M$^+$2H$_2$O), 308 and 302 which may be compared to related peaks in the mass spectrum of the starting material at m/e 375, 357, 304 and 298. Thin layer chromatography of the product on silica gel glass plates developed with chloroformmethanol, 5:1, and visualized by heating with vanillin-phosphoric acid reagent exhibited a single spot at $R_f$ 0.62.

The above product may be converted by known reactions (Example VI) to N-acetyl 13,14-dihydroprostaglandin $A_1$carboxamide or reduced as described in Example XXXVI to the N-acetyl 13,14-dihydroprostaglandin $F_{1\beta}$ carboxamide.

EXAMPLE VIII

A mixture of 10.0 g. (55.6 mmoles) of 5-bromovaleramide, 10 ml. of propionic anhydride and 5 drops of concentrated sulfuric acid was heated at 110° (oil bath) for 5 hours. The mixture was then cooled and was diluted with water (50 ml.). The aqueous layer was washed with methylene chloride (3×) and the combined organic extracts were dried (anhydrous magnesium sulfate) and concentrated to afford a semi-solid. The crude semi-solid was purified by silica gel chromatography using benzene then chloroform as eluents. The desired N-propionyl-5-bromovaleramide was obtained as a white solid weighing 7.71 g. (59.0% yield).

The product was recrystallized from methylene chloride:hexane as white microcrystals melting at 94°–97°.

The ir (CHCl$_3$) spectrum of the product exhibited carbonyl absorptions at 1695 cm$^{-1}$ (strong) and 1730 cm$^{-1}$ (moderate). The nmr (CDCl$_3$) spectrum of the product exhibited a triplet at 3.44 δ (J = 6 cps) for the C$\underline{H}_2$Br, a multiplet at 2.90–2.42 δ for the C$\underline{H}_2$CONHCOC$\underline{H}_2$, a multiplet at 2.10–1.68 δ for the C$\underline{H}_2$–C$\underline{H}_2$, and a triplet at 1.19 δ (J = 7 cps) for the C$\underline{H}_3$.

A solution of 7.40 g. (31.8 mmoles) of the N-propionyl-5-bromovaleramide prepared above and 12.5 g. (47.8 mmoles) of triphenylphosphine in 74 ml. of acetonitrile was heated at reflux under nitrogen overnight. The reaction was cooled and concentrated by rotary evaporation. The resultant white foam was triturated with benzene (6×) then was further purified by silica gel chromatography using chloroform then 10% methanol in chloroform as eluents. The desired [4-propionylaminocarbonylbutyl]-triphenylphosphonium bromide was collected as a white hygroscopic solid weighing 9.24 g. (58.4% yield).

The nmr spectrum (CDCl$_3$) exhibited a singlet at 10.3 δ for the N$\underline{H}$, a multiplet at 8.14–7.27 δ for the aromatic protons, a multiplet at 3.97–3.33 δ for the C$\underline{H}_2$P, a multiplet at 2.92–2.30 δ for the C$\underline{H}_2$CONHCOC$\underline{H}_2$, a multiplet at 2.21–1.40 δ for the C$\underline{H}_2$—C$\underline{H}_2$, and a triplet at 1.03 δ (J = 8 cps) for the C$\underline{H}_3$.

The above product may be caused to react with the known 2-[5α-hydroxy-3α-(tetrahydropyran-2-yloxy)-2β-(3α-(tetrahydropyran-2-yloxy)-trans-1-cis-5-octadien-1-yl)cyclopent-1α-yl]acetaldehyde, γ-hemiacetal (E. J. Corey, et al., J. Am. Chem. Soc., 93, 1490 (1971) to produce N-propionoyl-9α-hydroxy-11α,15α-bis-(tetrahydropyran-2-yloxy)-cis-5-trans-13-cis-17-prostatrienamide which may be converted by known reactions (E. J. Corey, ibid) into the N-propionoyl prostaglandin F$_3$ $_\alpha$ carboxamide or the N-acetyl prostaglandin E$_3$ carboxamide.

The above product may be caused to react with the mixed 2-[5α-hydroxy-3α-(tetrahydropyran-2-yloxy)-2β-(3β-methyl-3α-(tetrahydropyran-2-yloxy)-trans-1-octen-1-yl)cyclopent-1α-yl]acetaldehyde, γ-hemiacetal and 2-[5α-hydroxy-3α-(tetrahydropyran-2-yloxy)-2β-(3α-methyl-3β-(tetrahydropyran-2-yloxy)-trans-1-octen-1-yl)cyclopent-1α-yl]acetaldehyde, hemiacetal prepared in Example XL to produce N-propionoyl-9α-hydroxy-11α,15-bis-(tetrahydropyran-2-yloxy)-15-methyl-cis-5-trans-13-prostadienamides called Compound A. Compound A may be hydrolyzed as described in Example III to produce the N-propionoyl-15-methyl prostaglandin F$_2$ $_\alpha$ carboxamide (which may be subjected to catalytic hydrogenation as described in Example VII to produce N-propionoyl 15-methyl-13,14-dihydroprostaglandin F$_1$ $_\alpha$ carboxamide). Compound A may be subjected to oxidation as described in Example IV followed by hydrolysis as described in Example V to product N-propionoyl 15-methyl prostaglandin E$_2$ carboxamide called Compound B. Compound B may be dehydrated as described in Example VI to product N-propionoyl 15-methylprostaglandin A$_2$ carboxamide. Compound B may be catalytically hydrogenated as described in Example VII to produce N-propionoyl 15-methyl-13,14-dihydroprostaglandin E$_1$ carboxamide which may be dehydrated as described in Example VI to produce N-propionoyl 15-methyl-13,14-dihydroprostaglandin A$_1$, carboxamide. Compound B may be reduced as described in Example XXXVI to the N-propionoyl 15-methyl prostaglandin F$_{2\beta}$ carboxamide.

Compound A may be subjected to carefully controlled catalytic reduction to produce N-propionoyl-9α-hydroxy-11α,15-bis(tetrahydropyran-2-yloxy)-15-methyl-trans-13-prostenamides which may be converted by known reactions (E. J. Corey, et al., J. Am. Chem. Soc., 92, 2586 (1970) to N-propionoyl 15-methyl prostaglandin F$_1$ carboxamide and N-propionoyl 15-methylprostaglandin E$_1$ carboxamide. The latter may be converted as described in Example VI to N-propionoyl 15-methylprostaglandin A$_1$ carboxamide or reduced as described in Example XXXVI to produce the N-propionoyl 15-methyl prostaglandin F$_1$ $_\beta$ carboxamide.

The above product may be caused to react with the 2-[5α-hydroxy-3α-(tetrahydropyran-2-yloxy)-2β-(3α-(tetrahydropyran-2-yloxy)oct-1-yl)cyclopent-1α-yl]acetaldehyde, γ-hemiacetal (prepared in Example XXVII) to produce N-propionoyl-9α-hydroxy-11α,1-5α-bis-(tetrahydropyran-2-yloxy)-cis-5-prostenamide called Compound C. Compound C may be hydrolyzed as described in Example III to produce the N-propionoyl 13,14-dihydroprostaglandin F$_2$ $_\alpha$ carboxamide. Compound C may be subjected to oxidation as described in Example IV followed by hydrolysis as described in Example V to produce the N-propionoyl 13,14-dihydroprostaglandin E$_2$ carboxamide. The latter may be dehydrated as described in Example VI to produce the N-propionoyl 13,14-dihydroprostaglandin A$_2$ carboxamide or reduced as described in Example XXXVI to the N-propionoyl 13,14-dihydroprostaglandin F$_2$ $_\beta$ carboxamide.

The above product may be caused to react with the mixed 2[5α-hydroxy-3α-(tetrahydropyran-2-yloxy)-2β-(3β-methyl-3α-(tetrahydropyran-2-yloxy)oct-1-yl)cyclopent-1α-yl]acetaldehyde, γ-hemiacetal and 2-]5α-hydroxy-3α-(tetrahydropyran-2-yloxy)-2β-(3α-methyl-3α-(tetrahydropyran-2-yloxy)oct-1-yl)cyclopent-1α-yl]-acetaldehyde, γ-hemiacetal prepared in Example XXVIII to produce N-propionoyl-9α-hydroxy-15-methyl-11α,15-bis(tetrahydropyran-2-yloxy)-cis-5-prostenamides called Compound D. Compound D may be hydrolyzed as described in Example III to produce the N-propionoyl 15-methyl-13,14-dihydroprostaglandin F$_2$ $_\alpha$ carboxamides. Compound D may be subjected to oxidation as described in Example IV followed by hydrolysis as described in Example V to produce the N-propionoyl 15-methyl-13,14-dihydroprostaglandin E$_2$ carboxamides. The latter may be dehydrated as described in Example VI to produce the N-propionoyl 15-methyl-13,14-dihydroprostaglandin A$_2$ carboxamide or reduced as described in Example XXXVI to the N-propionoyl 15-methyl-13,14-dihydroprostaglandin F$_2$ $_\beta$ carboxamides.

The above product may be caused to react with the 2-[5α-hydroxy-3α-(tetrahydropyran-2-yloxy)-2β-(3β-(tetrahydropyran-2-yloxy)oct-1-yl)cyclopent-1α-yl]acetaldehyde, γ-hemiacetal prepared in Example XXIII to produce N-propionoyl-9α-hydroxy-11α,15β-bis(tetrahydropyran-2-yloxy)-cis-5-prostenamide called Compound E. Compound E may be hydrolyzed as described in Example III to produce the N-propionoyl-15-epi-13,14-dihydroprostaglandin F$_2$ $_\alpha$ carboxamide. Compound E may be subjected to oxidation as described in Example IV followed by hydrolysis as described in Example V to produce the N-propionoyl- 15-epi-13,14-dihydroprostaglandin $E_2$ carboxamide. The latter may be dehydrated as described in Example VI to produce the N-propionoyl-15-epi-13,14-dihydroprostaglandin $A_2$ carboxamide or reduced as described in Example XXXVI to the N-propionoyl-15-epi-13,14-dihydroprostaglandin $F_2$ $\beta$ carboxamide.

The above product may be caused to react with the 2-[5α-hydroxy-3α-(tetrahydropyran-2-yloxy)-2β-(tetrahydropyran-2-yloxy)-trans-1-octen-1-yl)cyclopent-1α-yl]acetaldehyde, γ-hemiacetal prepared in Example XXIV to produce N-propionoyl-9α-hyroxy-11α,15β-bis (tetrahydropyran-2-yloxy)-cis-5-trans-13-prostadienamide called Compound F. Compound F may be hydrolyzed as described in Example III to produce the N-propionoyl-15-epiprostaglandin $F_2$ $_\alpha$ carboxamide. Compound F may be subjected to oxidation as described in Example IV followed by hydrolysis as described in Example V to produce the N-propionoyl-15-epiprostaglandin $E_2$ carboxamide. The latter may be dehydrated as described in Example VI to produce the N-propionoyl-15-epiprostaglandin $A_2$ carboxamide or reduced as described in Example XXXVI to the N-propionoyl-15-epi-prostaglandin $F_2$ $\beta$ carboxamid The above product may be caused to react with the 2-[3α,5α-dihydroxy-2β-(3α-hydroxy-1-trans-octen-1-yl)cyclopent-1α-yl]acetaldehyde, γ-hemiacetal prepared in Example XXIV to produce the N-propionoyl-prostaglandin $F_{2\beta}$ carboxamide.

The above product may be caused to react with the 2-]3α, 5α-dihydroxy-2β-(3α-hydroxyoct-1-yl)cyclopent-1α-yl]acetaldehyde, γ-hemiacetal prepared in Example XXIV to produce the N-propionoyl-13,14-dihydroprostaglandin $F_2$ $_\alpha$ carboxamide.

The above product may be caused to react with the 2-[3α,5α-dihydroxy-2β-(3β-hydroxy-trans-1-octen-1-yl)cyclopent-1α-yl]acetaldehyde, γ-hemiacetal prepared in Example XXI to provide the N-propionoyl 15-epi-prostaglandin $F_2$ $_\alpha$ carboxamide.

The above product may be caused to react with the 2-[3α, 5α-dihydroxy-2β-(3β-hydroxyoct-1-yl)cyclopent-1α-yl]acetaldehyde, γ-hemiacetal prepared in Example XXI to provide the N-propionoyl 15-epi-13,14-dihydroprostaglandin $F_2$ $_\alpha$.

The above product may be caused to react with the 2-[3α,5α-dihydroxy-2β-(3α-hydroxy-3β-methyl-trans-1-octen-1-yl)cyclopent-1α-yl]acetaldehyde, γ-hemiacetal prepared in Example XXXVI to provide the N-propionoyl 15-methyl-prostaglandin $F_2$ $_\alpha$ carboxamide.

The above product may be caused to react with the 2-[3α, 5α-dihydroxy-2β-(3α-hydroxy-3β-methyl-oct-1-yl)cyclopent-1α-yl]acetaldehyde, γ-hemiacetal prepared in Example XXXVII to provide the N-propionoyl 15-methyl-13,14-dihydroprostaglandin $F_2$ $_\alpha$.

EXAMPLE IX

To a solution of 2.03 g. (4.00 mmoles) of the phosphonium bromide of Example VIII (dried in vacuo overnight at 110°) in 5 ml. of dimethyl sulfoxide was added 8.97 ml. (17.0 mmoles) of a 1.89 M solution of sodium methylsulfinylmethide in dimethyl sulfoxide To the resultant red ylide solution was added dropwise a solution of 876 mgs. (2.00 mmole) of the known 2-[5α-hydroxy-3α-(tetrahydropyran-2-yloxy)-2β-[3α-(tetrahydropyran-2-yloxy)-1-trans-octen-1-yl]cyclopent-1α-yl]acetaldehyde, γ-hemiacetal in 2.0 ml. of dimethyl sulfoxide. The mixture was stirred for 2.5 hours under nitrogen then was poured onto a stirred mixture of ice-water:ether. The aqueous layer was acidified (pH~ 3) with 10% hydrochloric acid and the acidified aqueous layer was extracted with ether (2×). The combined ethereal extracts were dried (anhydrous magnesium sulfate) and were concentrated to afford a crude oil. The oil was purified by column chromatography on silica gel (Baker 60–200 mesh) using benzene, chloroform, then ethyl acetate as eluents. After removal of less polar impurities the colorless, oily N-propionoyl-4α-hydroxy-11α, 15α-bis-(tetrahydropyran-2-yloxy)-cis-5-trans-13-prostadienamide was collected weighing 507 mgs. (43.6% yield).

The nmr spectrum ($CDCl_3$) of the oily product exhibited a multiplet at 5.66–5.27 δ for the olefinic protons, a broad singlet at 4.70 δ for the —O—C$\underline{H}$—O—,multiplets at 4.26–3.22 δ for the —C$\underline{H}$O and C$\underline{H}_2$—0, a broad singlet at 9.10 for the N$\underline{H}$, a quartet centered at 2.63 δ for the

a triplet centered at 1.20 δ for the C$\underline{H}_3$, and multiplets at 2.83–0.67 δ for the remaining protons.

The above product may be subjected to catalytic reduction to produce the N-propionoyl-9α-hydroxy-11α,15α-bis-(tetrahydropyran-2-yloxy)prostanamide called Compound A. Compound A may be hydrolyzed as described in Example III to produce the N-propionoyl-13,14-dihydroprostaglandin $F_1$ $_\alpha$ carboxamide. Compound A may be subjected to oxidation as described in Example IV followed by hydrolysis as described in Example V to produce the N-propionoyl-13,14-dihydroprostaglandin $E_1$ carboxamide called Compound B. Compound B may be dehydrated as described in Example VI to produce the N-propionoyl-13,14-dihydroprostaglandin $A_1$ carboxamide or reduced as described in Example XXXVI to afford the N-propionoyl-13,14-dihydroprostaglandin $F_1$ $\beta$ carboxamide.

The above starting material may be subjected to catalytic reduction to produce N-propionoyl-9α-hydroxy-11α,15α-bis-(tetrahydropyran-2-yloxy)-trans-13-prostenamide which may be converted by known reactions (E. J. Corey, et al., *J. Am. Chem. Soc.*, 92, 2586 (1970) to N-propionoyl prostaglandin $F_1$ $_\alpha$ carboxamide or N-propionoyl prostaglandin $E_1$ carboxamide. The latter may be converted by known reactions (Example VI) to N-propionoyl prostaglandin $A_1$ carboxamide or (Example XXXVI) to N-propionoyl prostaglandin $F_1$ $\beta$ carboxamide.

The above product may also be hydrolyzed as described in Example III to provide the N-propionoyl prostaglandin $F_2$ $_\alpha$ carboxamide. This material may be subjected to catalytic reduction as described in Example VII to the N-propionoyl-13,14-dihydroprostaglandin $F_1$ $_\alpha$ carboxamide.

EXAMPLE X

To a solution, cooled to −15°, to 749 mgs. (1.3 mmoles) of the chromatographed alcohol of Example IX in 8.0 ml. of acetone was added 0.56 ml. of Jones' reagent. The mixture was stirred in the cold for 15 minutes then was quenched by the addition of 0.56 ml. of 2-propanol. The quenched mixture was diluted with ethyl acetate, was washed with water (2X) and saturated brine (1X), was dried (anhydrous magnesium sulfate), and was concentrated to afford a crude oil which as purified by column chromatography (Baker "Analyzed" 60–200 mesh) using chloroform as eluent. Concentration of the first four fractions afforded the product, N-propionoyl-9-oxo-11α,15α-bis-(tetrahydropyran-2-yloxy)-cis-5-trans-13-prostadienamide, as a colorless oil weighing 416 mg. (55.6% yield).

EXAMPLE XI

A solution of 416 mg. of the chromatographed ketone of Example X and 5.0 ml. of a 65:35 mixture of acetic acid:water was stirred under nitrogen at room temperature overnight. Concentration of the mixture afforded an oil which was purified by column chromatography on silica gel (Mallinckrodt CC-4) using mixtures of chloroform:ethyl acetate as eluents. After removal of less polar impurities, the crystalline N-propionoyl-9-oxo-11α, 15α-dihydroxy-cis-5-trans-13-prostadienamide, the N-propionyl prostaglandin $E_2$ carboxamide, was collected weighing 76 mg. melting at 49°–51° from ethyl acetate:hexane.

The ir spectrum (CHCl$_3$) of the product exhibited strong adsorptions at 1735 and 1695 cm$^{-1}$ for the carbonyl groups and a medium adsorption at 970 cm$^{-1}$ for the trans double bond. The nmr (CDCl$_3$) spectrum of the product exhibited a multiplet at 5.70–5.43 δ for the trans double bond, a multiplet at 5.43–5.10 δ for the cis double bond, a multiplet at 4.30–3.69 δ for the CHO, a broad singlet at 3.42–2.80 δ for the OH and NH, a quartet centered at 2.60 δ for the COCH$_2$, a triplet centered at 1.13 δ for the —CH$_3$, and multiplets at 2.72–0.60 δ for the remaining protons.

The above product may be dehydrated as described in Example VI to the N-propionoyl prostaglandin $A_2$ carboxamide.

The above product may be catalytically hydrogenated as described in Example VII to the N-propionoyl 13,14-dihydro prostaglandin $E_1$ carboxamide. The latter may be dehydrated as described in Example VI to the N-propionoyl 13,14-dihydro prostaglandin $A_1$ carboxamide or reduced as described in Example XXXVI to provide the N-propionoyl 13,14-dihydroprostaglandin $F_1$ $_\beta$ carboxamide.

The above product may also be reduced as described in Example XXXVI to the N-propionoyl prostaglandin $F_2$ $_\beta$ carboxamide.

EXAMPLE XII

A solution of 7.96 g. of 5-bromovaleric acid chloride, 3.40 g. of cyclopropanecarboxamide, 3.16 g. of pyridine, and 20 ml. of 1,2-dimethoxyethane was heated to reflux under nitrogen for 1.5 hours, then was concentrated by rotary evaporation. The resultant semi-solid was triturated with methylene chloride (2X). The combined methylene chloride layers were washed with saturated brine, were dried (anhydrous magnesium sulfate), were treated with activated charcoal, and were filtered. The filtrate was concentrated on a steambath with addition of hexane until crystallization started. Thus, 3.98 g. (40% yield) of white, crystalline N-cyclopropanecarbonyl-5-bromovaleramide was obtained melting at 114°–115°C.

The nmr spectrum (CDCl$_3$) of the crystalline product exhibited a singlet at 9.60 δ for the NH, a multiplet at 3.73–3.26 δ for the -CH$_2$Br, a multiplet at 2.95–2.51 δ for the

a multiplet at 2.27–1.60 δ for the CH$_2$CH$_2$ and

and a multiplet at 1.20–0.68 δ for the remaining cyclopropyl protons.

A mixture of 4.96 g. (20 mmoles) of the N-cyclopropanecarbonyl-5-bromovaleramide prepared above, 7.86 g. (30 mmoles) of triphenylphosphine, and 50 ml. of acetonitrile were heated at reflux temperatures under nitrogen for 112 hours. The mixture was then concentrated and the resultant white foam was purified by column chromatography on Silica gel (Baker 60–200 mesh) using 5% methanol in methylene chloride as eluent. After removal of starting materials and less polar impurities, the desired [4-(cyclopropanecarbonylaminocarbonyl)butyl]triphenylphosphonium bromide was obtained as a white hygroscopic foam weighing 2.42 g. (23.8% yield).

The above product may be caused to react with the known 2-[5α-hydroxy-3α-hydroxy-3α-(tetrahydropyran-2-yloxy)-2β-(3α-(tetrahydropyran-2-yloxy)-trans-1-cis-5-octadien-1-yl)cyclopent-1α-yl]acetaldehyde, γ-hemiacetal (E. J. Corey, et al., J. Am. Chem. Soc., 93, 1490 (1971) to produce N-acetyl-9α-hydroxy-11α, 15α-bis-(tetrahydropyran-2-yloxy)-cis-5-trans-13-cis-17-prostatrienamide which may be converted by known reactions (E. J. Corey, ibid) into the N-cyclopropanecarbonyl prostaglandin $F_3$ $_\alpha$ carboxamide or the N-cyclopropanecarbonyl prostaglandin $E_3$ carboxamide.

The above product may be caused to react with the mixed 2-[5α-hydroxy-3α-(tetrahydropyran-2-yloxy)-2β-(3β-methyl-3α-(tetrahydropyran-2-yloxy)-trans-1-octen-1-yl)cyclopent-1α-yl]acetaldehyde, γ-hemiacetal and 2-[5α-hydroxy-3α-(tetrahydropyran-2-yloxy)-2β-(3α-methyl-3β-(tetrahydropyran-2-yloxy)-trans-1-octen-1-yl)cyclopent-1α-yl]acetaldehyde, γ-hemiacetal to produce N-cyclopropanecarbonyl-9α-hydroxy-11α,15-bis-(tetrahydropyran-2-yloxy)-15-methyl-cis-5-trans-13-prostadienamides called Compound A. Compound A may be hydrolyzed as described in Example III to produce the N-cyclopropanecarbonyl-15-methyl prostaglandin $F_2$ $_\alpha$ carboxamide (which may be subjected to catalytic hydrogenation as described in Example VII to produce N-cyclopropanecarbonyl-15-methyl-13,14-dihydroprostaglandin $F_1$ $_\alpha$ carboxamide). Compound A may be subjected to oxidation as described in Example IV followed by hydrolysis as described in Example V to produce N-cyclopropanecarbonyl 15-methyl prostaglandin $E_2$ carboxamide called Compound B. Compound B may be dehydrated as described in Example VI to produce N-cyclopropanecarbonyl 15-methylprostaglandin $A_2$ carboxamide. Compound B may also be catalytically hydrogenated as described in Example VII to produce N-cyclopropanecarbonyl 15-methyl-13,14-dihydroprostaglandin $E_1$ carboxamide which may be dehydrated as described in Example VI to produce N-cyclopropanecarbonyl 15-methyl-13,14-dihydroprostaglandin $A_1$ carboxamide or reduced as described in Example XXXVI to the N-cyclopropanecarbonyl 15-methyl-13,14-dihydroprostaglandin $F_1$ $\beta$ carboxamide. Compound B may also be reduced as described in Example XXXVI to the N-cyclopropanecarbonyl 15-methyl prostaglandin $F_2$ $\beta$ carboxamide.

Compound A may be subjected to carefully controlled catalytic reduction to produce N-cyclopropanecarbonyl-9α-hydroxy-11α,15α-bis-(tetrahydropyran-2-yloxy)-15β-methyl-trans-13-prostenamide which may be converted by known reactions (E. J. Corey, et al., *J. Am. Chem. Soc.*, 92, 2586 (1970)) to N-cyclopropanecarbonyl 15-methyl prostaglandin $F_1$ $\alpha$ carboxamide and N-cyclopropanecarbonyl 15-methylprostaglandin $E_1$ carboxamide. The latter may be converted as described in Example VI to N-cyclopropanecarbonyl 15-methylprostaglandin $A_1$ carboxamide or reduced as described in Example XXXVI to the N-cyclopropanecarbonyl 15-methylprostaglandin $F_1$ $\beta$ carboxamide.

The above product may be caused to react with the 2-[3α, 5α-hydroxy-2β-(3α-hydroxy-trans-1-octen-1-yl)cyclopent-1α-yl] acetaldehyde, γ-hemiacetal prepared in Example XXV to provide the N-cyclopropanecarbonyl prostaglandin $F_2$ $\alpha$ carboxamide.

The above product may be caused to react with the 2-[3α,5α-dihydroxy-2β(3α-hydroxyoct-1-yl)cyclopent-1α-yl]acetaldehyde, γ-hemiacetal prepared in Example XXIV to provide the N-cyclopropanecarbonyl 13,14-dihydroprostaglandin $F_2$ $\alpha$.

The above product may be caused to react with the 2-[5α-hydroxy-3α-)tetrahydropyran-2-yloxy)-2β-(3α-(tetrahydropyran-2-yloxy)oct-1-yl)cyclopent-1α-yl]acetaldehyde, γ-hemiacetal prepared in Example XXVII to product N-cyclopropanecarbonyl-9α-hydroxy-11α,15α-bis-(tetrahydropyran-2-yloxy)-cis-5-prostenamide called Compound C. Compound C may be hydrolyzed as described in Example III to produce the N-cyclopropanecarbonyl 13,14-dihydroprostaglandin $F_2$ $\alpha$ carboxamide. Compound C may be subjected to oxidation as described in Example IV followed by hydrolysis as described in Example V to produce the N-cyclopropanecarbonyl 13,14-dihydroprostaglandin $E_2$ carboxamide. The latter may be dehydrated as described in Example VI to produce the N-cyclopropanecarbonyl 13,14-dihydroprostaglandin $A_2$ carboxamide or reduced as described in Example XXXVI to the N-cyclopropanecarbonyl 13,14-dihydroprostaglandin $F_2$ $\beta$ carboxamide.

The above product may be caused to react with the mixed 2-[5α-hydroxy-3α-(tetrahydropyran-2-yloxy)-2β-(3β-methyl-3α-(tetrahydropyran-2-yloxy)oct-1-yl)cyclopent-1α-yl]acetaldehyde, γ-hemiacetal and 2-[5α-hydroxy-3α-(tetrahydropyran-2-yloxy)-2β-(3α-methyl-3β-(tetrahydropyran-2-yloxy)oct-1-yl)cyclopent-1α-yl]acetaldehyde, γ-hemiacetal prepared in Example XXVIII to product N-cyclopropanecarbonyl-9α-hydroxy-15-methyl-11α,15-bis-(tetrahydropyran-2-yloxy)-cis-5-prostenamide called Compound D. Compound D may be hydrolyzed as described in Example III to product the N-cyclopropanecarbonyl 15-methyl-13,14-dihydroprostaglandin $F_2$ $\alpha$ carboxamide. Compound D may be subjected to oxidation as described in Example IV followed by hydrolysis as described in Example V to produce the N-cyclopropanecarbonyl 15-methyl-13,14-dihydroprostaglandin $E_2$ carboxamide. The latter may be dehydrated as described in Example VI to produce the N-cyclopropanecarbonyl 15-methyl-13,14-dihydroprostaglandin $A_2$ carboxamide or reduced as described in Example XXXVI to the N-cyclopropanecarbonyl 15-methyl-13,14-dihydroprostaglandin $F_2$ $\beta$ carboxamide.

The above product may be caused to react with the 2-[5α-hydroxy-3α-(tetrahydropyran-2-yloxy)-2β-(3β-(tetrahydropyran-2-yloxy)oct-1-yl)cyclopent-1α-yl]acetaldehyde, γ-hemiacetal prepared in Example XXIII to produce N-cyclopropanecarbonyl-9α-hydroxy-11α,15β-bis-(tetrahydropyran-2-yloxy)-cis-5-prostenamide caled Compound E. Compound E may be hydrolyzed as described in Example III to produce the N-cyclopropanecarbonyl 15-epi-13,14-dihydroprostaglandin $F_2$ $\alpha$ carboxamide. Compound E may be subjected to oxidation as described in Example IV followed by hydrolysis as described in Example V to produce the N-cyclopropanecarbonyl-15-epi-13,14-dihydroprostaglandin $E_2$ carboxamide. The latter may be dehydrated as described in Example VI to produce the N-cyclopropanecarbonyl-15-epi-13,14-dihydroprostaglandin $A_2$ carboxamide or reduced as described in Example XXXVI to the N-cyclopropanecarbonyl-15-epi-13,14-dihydroprostaglandin $F_2$ $\beta$ carboxamide.

The above product may be caused to react with the 2-[5α-hydroxy-3α-(tetrahydropyran-2-yloxy)-2β-(3β-(tetrahydropyran-2-yloxy)-trans-1-octen-1-yl)cyclopent-1α-yl]acetaldehyde, γ-hemiacetal prepared in Example XXIV to produce N-cyclopropanecarbonyl-9α-hydroxy-11β,15α-bis(tetrahydropyran-2-yloxy)-trans-13-cis-5-prostenamide called Compound F. Compound F may be hydrolyzed as described in Example III to produce the N-cyclopropanecarbonyl-15-epi-prostaglandin $F_2$ $\alpha$ carboxamide. Compound F may be subjected to oxidation as described in Example IV followed by hydrolysis as described in Example V to produce the N-cyclopropanecarbonyl prostaglandin $E_2$ carboxamide. The latter may be dehydrated as described in Example VI to produce the N-cyclopropanecarbonyl-15-epi-prostaglandin $A_2$ carboxamide or reduced as described in Example XXXVI to the N-cyclopropanecarbonyl-15-epi-prostaglandin $F_2$ $\beta$ carboxamide.

The above product may be caused to react with the 2-[3α,5α-dihydroxy-2β-(3β-hydroxy-trans-1-octen-1-yl)cyclopent-1α-yl]acetaldehyde, γ-hemiacetal prepared in Example XXI to provide the N-cyclopropanecarbonyl 15-epi-prostaglandin $F_2$ $\alpha$ carboxamide.

The above product may be caused to react with the 2-[3α,5α-dihydroxy-2β-(3β-hydroxyoct-1-yl)cyclopent-1α-yl]acetaldehyde, γ-hemiacetal prepared in Example XXI to provide the N-cyclopropanecarbonyl 15-epi-13,14-dihydroprostaglandin $F_2$ $\alpha$.

The above product may be caused to react with the 2-[3α,5α-dihydroxy-2β-(3α-hydroxy-3β-methyl-trans-1-octen-1-yl)-cyclopent-1α-yl]acetaldehyde, γ-hemiacetal prepared in Example XXXVII to provide the N-cyclopropanecarbonyl 15-methylprostaglandin $F_2$ $\alpha$ carboxamide.

The above product may be caused to react with the 2-[3α,5α-dihydroxy-2β-(3α-hydroxy-3β-methyl-oct-1-yl)cyclopent-1α-yl]-acetaldehyde, γ-hemiacetal prepared in Example XXXVII to provide the N-cyclopropanecarbonyl 15-methyl-13,14-dihydroprostaglandin $F_2$ $\alpha$.

EXAMPLE XIII

To a solution of 1.53 g. (3.00 mmoles) of the phosphonium bromide of Example XII (dried in vacuo overnight at 110°) in 4.0 ml of dimethyl sulfoxide was added 3.38 ml. (6.93 mmoles) of a 2.05 M solution of sodium methylsulfinylmethide in dimethyl sulfoxide. To the resultant red ylide solution was added dropwise a solution of 438 mgs. (1.00 mmole) of the known 2-[5α-hydroxy-3α-(tetrahydropyran-2-yloxy)-2β-[3α-(tetrahydropyran-2-yloxy)-1-trans-octen-1-yl]cyclopent-1α-yl]acetaldehyde, γ-hemiacetal in 2.0 ml. of dimethyl sulfoxide. The mixture was stirred overnight under nitrogen then was poured onto a stirred mixture of icewater:ether. The aqueous layer was acidified (pH ~ 3) with 10% hydrochloric acid and the acidified aqueous layer was extracted with ether (2X). The combined ethereal extracts were dried (anhydrous magnesium sulfate) and were concentrated to afford a crude oil. The oil was purified by column chromatography on silica gel (Baker 60–200 mesh) using 10% benzene in chloroform as eluent. After removal of less polar impurities the colorless, oily N-cyclopropanecarbonyl-4α-hydroxy-11α,15α-bis-(tetrahydropyran-2-yloxy)-cis-5-trans-13-prostadienamide was collected weighing 289 mgs. attributable 49.0% yield).

The ir spectrum (CHCl$_3$) of the oily product exhibited strong absorptions at 1670 and 1720 cm$^{-1}$ attributable to the carbonyl groups and at 970 cm$^{-1}$ attributable to the trans double bond. The nmr spectrum (CDCl$_3$) of the oily product exhibited a multiplet at 5.66–5.27 δ for the olefinic protons, a broad singlet at 4.70 δ for the —O—CH—O—, multiplets at 4.26–3.22 δ for the —CHO and CH$_2$—O, a broad singlet 9.10 for the NH, and multiplets at 2.83–0.63 δ for the remaining protons.

The above product may also be subjected to carefully controlled catalytic reduction to produce N-cyclopropanecarbonyl-9α-hydroxy-11α,15α-bis-(tetrahydropyran-2-yloxy)-trans-13-prostenamide which may be converted by known reactions (E. J. Corey, et al., *J. Am. Chem. Soc.*, 92, 2586 (1970) to N-cyclopropanecarbonyl prostaglandin F$_1$ $_\alpha$ carboxamide or N-cyclopropanecarbonyl prostaglandin E$_1$ carboxamide. The latter may be converted by known reactions (Example VI) to N-cyclopropanecarbonyl prostaglandin A$_1$ carboxamide or (Example XXXVI) to N-cyclopropanecarbonyl prostaglandin F$_1$ $_\beta$ carboxamide.

The above product may also be subjected to catalytic reduction to produce the N-cyclopropanecarbonyl-9α-hydroxy-11α,15α-bis-(tetrahydropyran-2-yloxy)prostanamide called Compound A. Compound A may be hydrolyzed as described in Example III to produce the N-cyclopropanecarbonyl-13,14-dihydroprostaglandin F$_1$ $_\alpha$ carboxamide. Compound A may be subjected to oxidation as described in Example IV followed by hydrolysis as described in Example V to produce the N-cyclopropanecarbonyl-13,14-dihydroprostaglandin E$_1$ carboxamide called Compound B. Compound B may be dehydrated as described in Example VI to produce the N-cyclopropanecarbonyl-13,14-dihydroprostaglandin A$_1$ carboxamide or reduced as described in Example XXXVI to produce the N-cyclopropanecarbonyl-13,14-dihydroprostaglandin F$_1$ $_\beta$ carboxamide.

EXAMPLE XIV

A solution of the chromatographed alcohol of Example XIII (90 mgs.) in 2.0 ml. of a 65:35 mixture of acetic acid:water was stirred at 42° for 4.5 hours under nitrogen. Concentration of the reaction mixture afforded an oil which was purified by column chromatography on silica gel (SilicAR CC-4). After elution of less polar impurities with a 2:1 mixture of ethyl acetate:benzene, elution with a 9:1 mixture of methylene chloride: methanol gave the colorless, semi-solid product, N-cyclopropanecarbonyl-9α,11α,15α-trihydroxy-cis-5-trans-β-prostadienamide, weighing 39 mg. (60.7% yield) melting at 99°–102° (from ether).

The ir spectrum (CHCl$_3$) of the oily product exhibited strong absorptions at 1680 and 1720 cm$^{-1}$ attributable to the carbonyl groups and 970 cm$^{-1}$ attributable to the trans double bond. The nmr spectrum (CDCl$_3$) showed a broad singlet at 9.36 δ for the NH, a multiplet at 5.70–5.10 δ for the olefinic protons, multiplets at 4.27–3.00 δ for the -CHO, and multiplets at 2.84–0.56 δ for the remaining protons.

The above product may be catalytically hydrogenated as described in Example VII to produce the N-cyclopropanecarbonyl 13,14-dihydroprostaglandin F$_1$ $_\alpha$ carboxamide.

EXAMPLE XV

To a solution, cooled to −15°, of 200 mgs. of the chromatographed alcohol of Example XIII in 3.0 ml. of acetone was added 82 μl. of Jones' reagent. The mixture was stirred in the cold for 20 minutes then was quenched by the addition of 82 μl. of 2-propanol. The quenched mixture was diluted with ethyl acetate, was washed with water (2X) and saturated brine (1X), was dried (anhydrous magnesium sulfate), and was concentrated to afford the product, N-cyclopropanecarbonyl-9-oxo-11α,15α-bis-(tetrahydropyran-2-yloxy)-cis-5-trans-13-prostadienamide, as a colorless oil weighing 184 mg. (92.0% yield). The crude product was used without purification.

EXAMPLE XVI

A solution of 184 mg. of the crude ketone of Example XV and 4.0 ml. of a 65:35 mixture of acetic acid:water was heated, under nitrogen, at 42° for 4.5 hours. Concentration of the mixture afforded an oil which was purified by column chromatography on silica gel (SilicAR CC-4). After elution with a 2:1 mixture of ethyl acetate:benzene to remove less polar impurities, elution with ethyl acetate afforded the colorless, oily product, N-cyclopropanecarbonyl-9-oxo-11α,15α-dihydroxy-cis-5-trans-13-prostadienamide, the N-cyclopropanecarbonyl prostaglandin E$_2$ carboxamide, weighing 83 mg. (63.5% yield).

The ir spectrum (CHCl$_3$) of the oily product exhibited strong absorptions at 1730 cm$^{-1}$ for the ketone carbonyl, at 1680 and 1730 cm$^{-1}$ for the imide carbonyls, and 970 cm$^{-1}$ for the trans double bond. The nmr spectrum (CDCl$_3$) of the oily product exhibited a singlet at 9.17 δ for the NH, a multiplet at 5.70–5.49 δ for the trans olefin, a multiplet at 5.49–5.17 δ for the cis olefin, a multiplet at 4.30-3.77 δ for the CH-O, a singlet at 3.50 δ and multiplets at 3.04–0.63 δ for the remaining protons.

The above product may be dehydrated as described in Example VI to the N-cyclopropanecarbonyl prostaglandin A$_2$ carboxamide.

The above product may be reduced as described in Example XXXVI to the N-cyclopropanecarbonyl prostaglandin F$_2$ $_\beta$ carboxamide.

The above product may also be catalytically hydrogenated as described in Example VII to the N-cyclopropanecarbonyl 13,14-dihydroprostaglandin E$_1$ carboxamide. The latter may be dehydrated as described in Example VI to the N-cyclopropanecarbonyl 13,14- dihydroprostaglandin $A_1$ carboxamide or reduced as described in Example XXXVI to the N-cyclopropanecarbonyl 13,14-dihydroprostaglandin $F_1 \beta$ carboxamide.

EXAMPLE XVII

A mixture of 3.6 g. (20 mmoles) of 5-bromovaleramide and 12.0 g. (0.10 mole) of trimethylacetyl chloride (Aldrich) was heated at reflux under nitrogen for 4.5 hours. The excess acid chloride was removed under reduced pressure and the resultant oil was recrystallized from hexane as white needles weighing 1.83 g. (28.8% yield) and melting at 53°–57°.

The nmr spectrum ($CDCl_3$) showed a singlet at 1.16 $\delta$ for $C(\underline{CH}_3)_3$, a multiplet at 1.56–2.08 $\delta$ for $—\underline{CH}_2C-\underline{H}_2—$, a multiplet at 2.47–3.03 $\delta$ for

and a multiplet at 3.15–3.66 $\delta$ for $—\underline{CH}_2Br$.

A solution of 1.82 g. (6.80 mmoles) of the N-trimethylacetyl-5-bromovaleramide prepared above and 2.67 g. (10.2 mmoles) of triphenylphosphine in 18 ml. of acetonitrile was heated to reflux under nitrogen for 96 hours. The solution was concentrated and the resultant solid was triturated with benzene (4x). The triturated solid was purified by silica gel column chromatography using first ethyl acetate to remove high $R_f$ impurities then with a 9:1 mixture of methylene chloride:methanol. The salt, [4-trimethylacetylaminocarbonylbutyl]triphenylphosphonium bromide, was obtained as crystals from methylene chloride:ethyl acetate weighing 0.750 g. melting at 133.5°–138°.

The ir spectrum ($CHCl_3$) of the product exhibited a strong absorption at 1734 $cm^{-1}$ attributable to the carbonyl groups. The nmr spectrum ($CDCl_3$) showed a singlet at 1.25 $\delta$ for the $C(\underline{CH}_3)_3$, a multiplet at 1.57–2.10 $\delta$ for the $—\underline{CH}_2\underline{CH}_2—$, a multiplet at 2.63–3.10 $\delta$ for the $—\underline{CH}_2C—$, a broad multiplet at 3.37–3.97 $\delta$ for the $—\underline{CH}_2P$, a multiplet at 7.50–7.98 $\delta$ for the $\phi_3P$, and a singlet at 9.52 $\delta$ for the $N—\underline{H}$.

The above product may be caused to react with the known 2-[5α-hydroxy-3α-(tetrahydropyran-2-yloxy)-2β-(3α-(tetrahydropyran-2-yloxy)-trans-1-cis-5-octadien-1-yl)cyclopent-1α-yl]acetaldehyde, γ-hemiacetal (E. J. Corey, et al., J. Am. Chem. Soc., 93, 1490 (1971) to produce N-trimethylacetyl-9α-hydroxy-11α,15α-bis-(tetrahydropyran-2-yloxy)-cis-5-trans-13-cis-17-prostatrienamide which may be converted by known reactions (E. J. Corey, ibid) into the N-trimethylacetyl prostaglandin $F_3 \alpha$ carboxamide or the N-trimethylacetyl prostaglandin $E_3$.

The above product may be caused to react with the mixed 2-[5α-hydroxy-3α-(tetrahydropyran-2-yloxy)-2β-(3β-methyl-3α-(tetrahydropyran-2-yloxy)-trans-1-octen-1-yl)cyclopent-1α-yl]acetaldehyde, γ-hemiacetal and 2-[5α-hydroxy-3α-(tetrahydropyran-2-ylox y)-2β-(3α-methyl-3β-(tetrahydropyran-2-yloxy)-trans-1-octen-1-yl)cyclopent-1α-yl]acetaldehyde, γ-hemiacetal to produce N-trimethylacetyl-9α-hydroxy-11α,1-5α-bis-(tetrahydropyran-2-yloxy)-15β-methyl-cis-5-trans-13-prostadienamide and N-trimethylacetyl-9α-hydroxy-11α,15β-bis-(tetrahydropyran-2-yloxy)-15α-methyl-cis-5-trans-13-prostadienamide called Compound A. Compound A may be hydrolyzed as described in Example III to produce the N-trimethylacetyl-15-methyl prostaglandin $F_2 \alpha$ carboxamides (which may be subjected to catalytic hydrogenation as described in Example VII to produce N-trimethylacetyl 15-methyl-13,14-dihydroprostaglandin $F_1 \alpha$ carboxamide). Compound A may be subjected to oxidation as described in Example IV followed by hydrolysis as described in Example V to produce N-trimethylacetyl 15-methyl prostaglandin $E_2$ carboxamide called Compound B. Compound B may be dehydrated as described in Example VI to produce N-trimethylacetyl 15-methylprostaglandin $A_2$ carboxamide. Compound B may also be catalytically hydrogenated as described in Example VII to produce N-trimethylacetyl 15-methyl-13,14-dihydroprostaglandin $E_1$ carboxamide which may be dehydrated as described in Example VI to produce N-trimethylacetyl 15-methyl-13,14-dihydroprostaglandin $A_1$ carboxamide or reduced as described in Example XXXVI to the N-trimethylacetyl 15-methyl-13,14-dihydroprostaglandin $F_1 \beta$ carboxamide.

Compound A may be subjected to carefully controlled catalytic reduction to produce N-trimethylacetyl-9α-hydroxy-11α,15-bis-(tetrahydropyran-2-yloxy)-15-methyl-trans-13-prostenamide which may be converted by known reactions (E. J. Corey, et al., J. Am. Chem. Soc., 92, 2586 (1970) to N-trimethylacetyl 15-methyl prostaglandin $F_1 \alpha$ carboxamide and N-trimethylacetyl 15-methylprostaglandin $E_1$ carboxamide. The latter may be converted as described in Example VI to N-trimethylacetyl 15-methylprostaglandin $A_1$ carboxamide or as described in Example XXXVI to N-trimethylacetyl 15-methylprostaglandin $F_1 \beta$ carboxamide.

The above product may be caused to react with the hemiacetal, 2-[3α,5α-dihydroxy-2β-(3α-hydroxy-trans-1-octen-1-yl)cyclopent-1α-yl]acetaldehyde, γ-hemiacetal, prepared in Example XXV to produce N-trimethylacetyl prostaglandin $F_2 \alpha$ .

The above product may be caused to react with the hemiacetal, 2-[3α,5α-dihydroxy-2β-(3α-hydroxyoct-1-yl)cyclopent-1α-yl]acetaldehyde, γ-hemiacetal, prepared in Example XXVI to provide N-trimethylacetyl 13,14-dihydroprostaglandin $F_2 \alpha$ .

The above product may be caused to react with the 2-[5α-hydroxy-3α-(tetrahydropyran-2-yloxy)-2β-(3α-(tetrahydropyran-2-yloxy)oct-1-yl)cyclopent-1α-yl]acetaldehyde, γ-hemiacetal prepared in Example XXVII to produce N-trimethylacetyl-9α-hydroxy-11α,15α-bis-(tetrahydropyran-2-yloxy)-cis-5-prostenamide called Compound C. Compound C may be hydrolyzed as described in Example III to produce the N-trimethylacetyl 13,14-dihydroprostaglandin $F_2 \alpha$ carboxamide. Compound C may be subjected to oxidation as described in Example IV followed by hydrolysis as described in Example V to produce the N-trimethylacetyl 13,14-dihydroprostaglandin $E_2$ carboxamide. The latter may be dehydrated as described in Example VI to produce the N-trimethylacetyl 13,14-dihydroprostaglandin $A_2$ carboxamide or reduced as described in Example XXXVI to the N-trimethylacetyl 13,14-dihydroprostaglandin $F_2 \beta$ carboxamide.

The above product may be caused to react with the mixed 2-[5α-hydroxy-3α-(tetrahydropyran-2-yloxy)-2β-(3β-methyl-3α-(tetrahydropyran-2-yloxy)oct-1-yl)cyclopent-1α-yl]acetaldehyde, γ-hemiacetal and 2-[5α-hydroxy-3α-(tetrahydropyran-2-yloxy)-2β-(3α-methyl-3β-(tetrahydropyran-2-yloxy)oct-1-yl)cyclopent-1α-yl]-acetaldehyde, γ-hemiacetal to produce N-trimethylacetyl-9α-hydroxy-15-methyl-11α,15-bis(- tetrahydropyran-2-yloxy)-cis-5-prostenamide called Compound D. Compound D may be hydrolyzed as described in Example III to produce the N-trimethylacetyl 15-methyl-13,14-dihydroprostaglandin $F_2\alpha$ carboxamide. Compound D may be subjected to oxidation as described in Example IV followed by hydrolysis as described in Example V to produce the N-trimethylacetyl 15-methyl-13,14-dihydroprostaglandin $E_2$ carboxamide. The latter may be dehydrated as described in Example V to produce the N-trimethylacetyl 15-methyl-13,14-dihydroprostaglandin $A_2$ carboxamide or reduced as described in Example XXXVI to produce the N-trimethylacetyl 15-methyl-13,14-dihydroprostaglandin $F_2\beta$ carboxamide.

The above product may be caused to react with the 2-[5α-hydroxy-3α-(tetrahydropyran-2-yloxy)-2β-(3β-(tetrahydropyran-2-yloxy)oct-1-yl)cyclopent-1α-yl]acetaldehyde, γ-hemiacetal prepared in Example XXIII to produce N-trimethylacetyl-9α-hydroxy-11α,15β-bis-(tetrahydropyran-2-yloxy)-cis-5-prostenamide called Compound E. Compound E may be hydrolyzed as described in Example III to produce the N-trimethylacetyl-15-epi-13,14-dihydroprostaglandin $F_2\alpha$ carboxamide. Compound E may be subjected to oxidation as described in Example IV followed by hydrolysis as described in Example V to produce the N-trimethylacetyl 15-epi-13,14-dihydroprostaglandin $E_2$ carboxamide. The latter may be dehydrated as described in Example VI to produce the N-trimethylacetyl 15-epi-13,14-dihydroprostaglandin $A_2$ carboxamide or reduced as described in Example XXXVI to produce the N-trimethylacetyl 13,14-dihydroprostaglandin $F_2\beta$ carboxamide.

The above product may be caused to react with the 2-[5α-hydroxy-3α-(tetrahydropyran-2-yloxy)-2β-(3β-(tetrahydropyran-2-yloxy)-1-trans-octen-1-yl)cyclopent-1α-yl]acetaldehyde, γ-hemiacetal prepared in Example XXIV to produce N-trimethylacetyl-9α-hydroxy-11α,15β-bis(tetrahydropyran-2-yloxy)-trans-13-cis-5-prostadienamide called Compound F. Compound F may be hydrolyzed as described in Example III to produce the N-trimethylacetyl 15-epi-prostaglandin $F_2\alpha$ carboxamide. Compound F may be subjected to oxidation as described in Example IV followed by hydrolysis as described in Example V to produce the N-trimethylacetyl 15-epi prostaglandin $E_2$ carboxamide. The latter may be dehydrated as described in Example VI to produce the N-trimethylacetyl 15-epi prostaglandin $A_2$ carboxamide or reduced as described in Example XXXVI to produce the N-trimethylacetyl 15-epi-prostaglandin $F_2\beta$ carboxamide.

The above product may be caused to react with the 2-[3α-dihydroxy-2α-(3α-hydroxy-trans-1-octen-1-yl)cyclopent-1α-yl]acetaldehyde, γ-hemiacetal prepared in Example XXI to provide the N-trimethylacetyl 15-epi-prostaglandin $F_2\alpha$ carboxamide.

The above product may be caused to react with the 2-[3α, 5α-dihydroxy-2β-(3β-hydroxyoct-1-yl)cyclopent-1α-yl]acetaldehyde, γ-hemiacetal prepared in Example XXI to provide the N-trimethylacetyl 15-epi-13,14-dihydroprostaglandin $F_2\alpha$.

The above product may be caused to react with the 2-[3α,5α-dihydroxy-2β-(3α-hydroxy-3β-methyl-trans-1-octen-1-yl)cyclopent-1α-yl]acetaldehyde, γ-hemiacetal prepared in Example XXXVII to provide the N-trimethylacetyl 15-methylprostaglandin $F_2\alpha$.

The above product may be caused to react with the 2-[3α,5α-dihydroxy-2β-(3α-hydroxy-3β-methyl-trans-1-octen-1-yl)cyclopent-1α-yl]acetaldehyde, γ-hemiacetal prepared in Example XXXVII to provide the N-trimethylacetyl 15-methylprostaglandin $F_2\alpha$carboxamide.

The above product may be caused to react with the 2-[3α, 5α-dihydroxy-2β-(3α-hydroxy-3β-methyl-oct-1-yl) cyclopent-1α-yl]acetaldehyde, γ-hemiacetal prepared in Example XXXVII to provide the N-trimethylacetyl 15-methyl-13,14-dihydroprostaglandin $F_2\alpha$.

EXAMPLE XVIII

To a solution of 1.22 g. (2.32 mmoles) of [4-trimethylacetylaminocarbonylbutyl]triphenylphosphonium bromide, as prepared in Example XVII, in 4.0 ml. of dry dimethyl sulfoxide was added 2.22 ml. (4.54 mmoles) of a 2.05 M solution of sodium methylsulfinylmethide in dimethyl sulfoxide. To this red ylide solution was added dropwise a solution of 0.219 g. (0.5 mmole) of 2-[5α-hydroxy-3α-(tetrahydropyran-2-2-yloxy)-2β-(3α-(tetrahydropyran-2-yloxy)-trans-1-octen-1-yl)cyclopent-1α-yl]acetaldehyde, γ-hemiacetal in 1.0 ml. of dry dimethyl sulfoxide. After being stirred at room temperature under nitrogen for 20 hours the reaction was poured onto ice water. The aqueous solution was covered with ether and was acidified to pH ~ 3 by the addition of 10% hydrochloric acid. The aqueous mixture was further extracted with ether (3X); the combined ethereal extracts were dried (anhydrous magnesium sulfate) and concentrated to afford a viscous oil. Purification of the crude product was effected by silica gel column chromatography using chloroform as eluent. The resultant semi-solid was triturated with ether:hexane afforded the oily N-trimethylacetyl-9α-hydroxy-11α,15α-bis-(tetrahydropyran-2-yloxy)-cis-5-trans-13-prostadienamide weighing 401 mg.

The nmr spectrum (CDCl$_3$) showed a singlet at 1.20 δ for the C(CH$_3$)$_3$, a broad singlet at 4.48–4.73 δ for the OCHO, and a multiplet at 5.15–5.60 δ for the olefinic protons as distinct absorptions.

The above product may be hydrolyzed as described in Example III to provide the N-trimethylacetyl prostaglandin $F_2\alpha$ carboxamide which may be catalytically reduced as described in Example VII to provide the N-trimethylacetyl 13,14-dihydroprostaglandin $F_1\alpha$carboxamide.

The above product may also be subjected to catalytic reduction to produce N-trimethylacetyl-9α-hydroxy-11α,15α-bis(tetrahydropyran-2-yloxy)-trans-13-prostenamide which may be converted by known reactions (E. J. Corey, et al., *J. Am. Chem. Soc.*, 92, 2586 (1970) to N-trimethylacetyl prostaglandin $F_1\alpha$ carboxamide or N-trimethylacetyl prostaglandin $E_1$ carboxamide. The latter may be converted by known reactions (Example VI) to N-trimethylacetyl prostaglandin $A_1$ carboxamide or (Example XXXVI) to N-trimethylacetyl-prostaglandin $F_1\beta$ carboxamide.

The above product may also be subjected to catalytic reduction to produce the N-trimethylacetyl-9α-hydroxy-11α,15α-bis(tetrahydropyran-2-yloxy)prostanamide called Compound A. Compound A may be hydrolyzed as described in Example III to produce the N-trimethylacetyl-13,14-dihydroprostaglandin $F_1\alpha$ carboxamide. Compound A may be subjected to oxidation as described in Example IV followed by hydrolysis as described in Example V to produce the N-trimethylacetyl-13,14-dihydroprostaglandin $E_1$ carboxamide called Compound B. Compound B may be dehydrated as described in Example VI to produce the N-trimethylacetyl-13,14-dihydroprostaglandin $A_1$ carboxamide or reduced as described in Example XXXVI to produce the N-trimethylacetyl-13,14-dihydroprostaglandin $F_1\beta$ carboxamide.

EXAMPLE XIX

To a solution cooled to −20° under nitrogen of 0.401 g. of the N-trimethylacetyl-9α-hydroxy-11α,15α-bis-(tetrahydropyran-2-yloxy)-cis-5-trans-13-prostadienamide of Example XVIII in 4.0 ml. of reagent grade acetone was added 0.165 ml. of Jones' reagent. The mixture was stirred in the cold for 20 minutes then was quenched by the addition of 0.165 ml. of isopropanol. The mixture was stirred for 5 minutes then was diluted with ethyl acetate; the diluted solution was washed with water (2X) and with saturated brine (1X), was dried (anhydrous magnesium sulfate) and was concentrated to give the crude, oily N-trimethylacetyl-9-oxo-11α,1-5α-bis-(tetrahydropyran-2-yloxy)-cis-5-trans-13-prostadienamide weighing 352 mg. which was used without purification.

EXAMPLE XX

A solution of 352 mg. of the crude N-trimethylacetyl-9-oxo-11α,15α-bis-tetrahydropyran-2-yloxy)-cis-5-trans-13-prostadienamide of Example XIX in 4.0 ml. of a 65:35 mixture of acetic acid:water was stirred under nitrogen for 4.5 hours at 40° ± 2° then was concentrated. The resultant oil was subjected to column chromatography on silica gel (SilicAR CC-4) using benzene: ethyl acetate as eluent. After removal of high $R_f$ impurities, the oily product, N-trimethylacetyl-9-oxo-11α,15α-dihydroxy-cis-5-trans-13-prostadienamide, the N-trimethylacetyl prostaglandin $E_2$ carboxamide, was eluted weighing 45 mg.

The ir spectrum ($CHCl_3$) of the product exhibited strong absorptions at 1680 and 1730 $cm^{-1}$ attributable to the carbonyl groups and at 965 $cm^{-1}$ attributable to the trans double bond. The nmr spectrum ($CDCl_3$) showed a singlet at 1.22 δ for the $C(CH_3)_3$, a broad singlet at 3.31 δ for the OH, a multiplet at 3.90–4.23 δ for the CHO, a multiplet at 5.23–5.52 δ for the cis olefin, a multiplet at 5.52–5.76 δ for the trans olefin, a broad singlet at 8.20 δ for the N-H, and multiplets at 0.70–3.05 δ for the remaining protons. The uv spectrum (MeOH) after base (KOH) treatment exhibited the characteristic PGB absorption at 278 mμ.

The above product may be dehydrated as described in Example VI to provide the N-trimethylacetyl prostaglandin $A_2$ carboxamide or reduced as described in Example XXXVI to provide the N-trimethylacetyl prostaglandin $F_2 \beta$ carboxamide.

The above product may also be catalytically reduced as described in Example VII to produce the N-trimethylacetyl 13,14-dihydroprostaglandin $E_1$ carboxamide. The latter may be dehydrated as described in Example VI to produce the N-trimetylacetyl 13,14-dihydroprostaglandin $A_1$ carboxamide or reduced as described in Example XXXVI to produce the N-trimethylacetyl 13,14-dihydroprostaglandin $F_1 \beta$ carboxamide.

EXAMPLE XXI

A heterogeneous mixture of 2.24 g. (5.0 mmoles) of the known (E. J. Corey, et al., JACS, 93, 1491 (1971)) 2-[5α-hydroxy-3α-p-phenylbenzoyloxy-2β-(3β-hydroxy-trans-1-octen-1-yl)cyclopent-1α-yl]acetic acid, γ-lactone and 0.680 g. (5.0 mmoles) of anhydrous potassium carbonate in 22 ml. of absolute methanol was stirred at room temperature under nitrogen for 2.0 hours. The reaction mixture was then cooled in ice and was quenched by the addition of 10 ml. of 1.0N aqueous hydrochloric acid. The quenched mixture was diluted with water (22 ml.) and filtered to remove the precipitated methyl p-phenylbenzoate. The filtrate was extracted with ethyl acetate(3 × 5 ml.); the combined orgnaic extracts were washed with saturated sodium bicarbonate and saturated brine, were dried (anhydrous magnesium sulfate), and were concentrated to afford the desired 2-[3α,5α-dihydroxy-2β-)3β-hydroxy-trans-1-octen-1-yl)cyclopent-1α-yl]acetic acid, γ-lactone as a viscous oil weighing 1.17 g. (87.4% yield). The ir and nmr spectra of the product were superimposable on those of the known 15α-epimer.

The above starting material may be reduced as described in Example XXV to proudce the 2-[3α,5α-dihydroxy-2β-(3β-hydroxy-trans-1-octen-1-yl)cyclopent-1α-yl]acetaldehyde, γ-hemiacetal.

The above starting material may be catalytically reduced as described in Example XXVI to provide the 2-[5α-hydroxy-3α-p-phenylbenzoyloxy-2β-(3β-hydroxyoct-1-yl)cyclopent-1α-yl]acetic acid, γ-lactone which may be reduced as described in Example XXV to provide the 2-[3α,5α-dihydroxy-2β-(3β-hydroxyoct-1-yl)cyclopent-1α-yl]acetaldehyde, γ-hemiacetal.

EXAMPLE XXII

To a solution of 1.17 g. (4.37 mmoles) of the 2-[3α,-5α-dihydroxy-2β(3β-hydroxy-trans-1-octen-1-yl)cyclopent-1α-yl]acetic acid, γ-lactone prepared above in Example XXI and 1.17 ml. of 2,3-dihydropyran in 12 ml. of methylene chloride was added 12 mg. of p-toluenesulfonic acid monohydrate. The reaction was stirred under nitrogen at room temperature for 15 minutes then was diluted with ether (100 ml.). The diluted solution was washed with saturated sodium bicarbonate and saturated brine, was dried (anhydrous magnesium sulfate), and was concentrated to afford the desired 2-[5α-hydroxy-3α-(tetrahydropyran-2-yloxy)-2β-(3β-(tetrahydropyran-2-yloxy)-trans-octen-1-yl)cyclopent-1α-yl]acetic acid, γ-lactone as a viscous oil weighing 2.10 g. (>100% yield). The ir and nmr spectra were superimposable on those of the known 15α-epimer.

EXAMPLE XXIII

A heterogeneous mixture of 2.02 g. of the 2-[5α-hydroxy-3α-(tetrahydropyran-2-yloxy)-2β-(3β-(tetrahydropyran-2-yloxy)-trans-1-octen-1-yl)cyclopent-1α-yl]acetic acid, γ-lactone prepared above and 202 mg. of 5% palladium on carbon in 20 ml. of absolute methanol is stirred under 1 atmosphere of hydrogen for 4.5 hours at room temperature. The mixture is then filtered (Celite); concentration of the filtrate provides the desired 2-[5α-hydroxy-3α(tetrahydropyran-2-yloxy)-2β-(3β-(tetrahydropyran-2-yloxy)oct-1-yl)cyclopent-1α-yl]acetic acid, γ-lactone.

This compound may be reduced as described in Example XXIV to provide the 2-[5α-hydroxy-3α-(tetrahydropyran -2-yloxy)-2β-(3β-(tetrahydropyran-2-yloxy)oct-1-yl)cyclopent-1α-yl]acetaldehyde, γ-hemiacetal.

EXAMPLE XXIV

To a solution, cooled to −78° under nitrogen, of 1.90 g. (4.37 mmoles) the 2-[5α-hydroxy-3α-(tetrahydropyran-2-yloxy)-2β-(3β-(tetrahydropyran-2-yloxy)-trans-octen-1-yl)cyclopent-1α-yl]acetic acid, γ-lactone prepared above in Example XXXIII in 25 ml. of dry toluene was added dropwise 5.92 ml. of a 20% solution of diisobutylaluminum hydride in hexane (Alfa Inorganics). The reaction was stirred for 45 minutes at −78° then was quenched by the dropwise addition of methanol until gas evolution ceased. The quenched reaction was let warm to room temperature, was diluted with ether, was washed with a 50% sodium potassium tartrate solution and with saturated brine, was dried (anhydrous magnesium sulfate), and was concentrated to provide a viscous, yellow oil which was purified by column chromatography (Baker Silica Gel 60–200 mesh) using mixtures of benzene:ethyl acetate as eluents. After removal of less polar impurities the desired 2-[5α-hydroxy-3α-(tetrahydropyran-2-yloxy)-2β-(3β-tetrahydropyran-2-yloxy)trans-octen-1-yl)cyclopent-1α-yl]acetaldehyde, γ-hemiacetal was collected as a colorless oil weighing 1.59 g. (83.5% yield). The ir and nmr spectra were superimposable on those of the known 15α-epimer.

EXAMPLE XXV

To a solution cooled to −78° of 866 mg. (1.93 mmoles) of the known 2-[3α-p-phenylbenzoyloxy-5α-hydroxy-2β-(3α-hydroxy-trans-1-octen-1-yl)cyclopent-1α-yl]acetic acid, γ-lactone in 12 ml. of toluene was added 4.82 ml. (3.88 mmoles) of a 0.805 M solution of diisobutylaluminum hydride in hexane. The reaction was stirred in the cold under nitrogen for 30 minutes then was quenched by the addition of methanol (0.5 ml.). The reaction was let warm to room temperture then was concentrated to a white semisolid. The semisolid was slurried with methanol (3x), was filtered through Celite 545, and was concentrated. Purification of the crude product by silica gel chromatography using mixtures of chloroform:ethyl acetate as eluents afforded the desired 2-[2β-(3α-hydroxy-trans-1-octen-1-yl)-3α,5α-dihydroxycyclopent-1α-yl]acetaldehyde, γ-hemiacetal as a colorless oil weighing 304 mg. (59.5% yield).

The ir spectrum (CHCl$_3$) of the product exhibited strong adsorptions at 970 cm$^{-1}$ (trans olefin) and 3380 cm$^{-1}$ (OH). The nmr spectrum (CDCl$_3$) showed multiplets at 5.64–5.20 δ (2H) for the trans olefin, at 4.66–4.22 δ (1H) for the O—CH—O, at 4.18–3.19 δ (3H) for the OCH, and at 2.62–0.40 δ (20H) for the remaining protons.

EXAMPLE XXVI

A heterogeneous mixture of 954 mg. (2.14 mmoles) of the known 2-[3α-p-phenylbenzoyloxy-5α-hydroxy-2β-(3α-hydroxy-trans-1-octen-1-yl)cyclopent-1α-yl]acetic acid, γ-lactone and 95 mg. of 10% palladium on carbon in 10 ml. of absolute methanol is stirred under one atmosphere of hydrogen at room temperature for 4.5 hours. The mixture is then filtered through a pad of Celite and concentrated to afford the desired 2-[3α-p-phenylbenzoyloxy-2β-(3α-hydroxyoct-1-yl)-5α-hydroxy-cyclopent-1α-yl]acetic acid, γ-lactone.

This compound may be reduced as described in Example XXV to 2-[3α,5α-dihydroxy-2β-(3α-hydroxyoct-1-yl)cyclopent-1α-yl]acetaldehyde, γ-hemiacetal.

EXAMPLE XXVII

A mixture of the known 2-[5α-hydroxy-3α-(tetrahydropyran-2-yloxy)-2β-(3α-(tetrahydropryan-2-yloxy)-trans-1-octen-1-yl)cyclopentan-1α-yl]acetic acid, γ-lactone (0.840 g., 1.92 mmoles), 5% palladium on carbon (0.10 g.) and absolute ethanol (25 ml.) is stirred magnetically under 1 atmosphere of hydrogen at room temperature for 5 hours. The resulting mixture is filtered, ad the filtrate is concentrated to afford a thick, colorless oil, 2-[5α-hydroxy-3α-(tetrahydropyran-2-yloxy)-2β-(3α-(tetrahydropyran-2-yloxy)oct-1-yl)cyclopent-1α-yl]acetic acid, γ-lactone. The compound is converted by the method of Example XXV to 2-[5α-hydroxy-3α-(tetrahydropyran-b 2-yloxy)-2β-(3α-(tetrahydropyran-2-yloxy)oct-1-yl)cyclopentan-1α-yl]acetaldehyde, γ-hemiacetal.

EXAMPLE XXVIII

A mixture of 2.68 g. (6.00 mmoles) of the γ-lactone starting material of Example XXXVII and 0.636 g. of 10% palladium on carbon in 29 ml. of absolute ethanol was stirred under 1 atmosphere of hydrogen at ambient temperature for 5 hours, then the mixture was filtered through Celite 545. Concentration of the filtrate afforded the desired 2-[3α-p-biphenylcarboxy-5α-hydroxy-2β-[3-oxooct-1-yl]cyclopent-1α-yl]acetic acid, γ-lactone.

This compound may be converted by the process of Example XXXVII to 2-[3α-p-biphenylcarboxy-5α-hydroxy-2β-[3α-hydroxy-3β-methyloct-1-yl]cyclopent-1α-yl]acetic acid, γ-lactone, and 2-[3α-p-phenylbenzoyloxy-5α-hydroxy-2β-3β-hydroxy-3α-methyloct-1-yl]cyclopent-1α-yl]acetic acid, γ-lactone which may be converted by the process of Example XXXVIII to 2-[3α,5α-dihydroxy-2β-(3α-hydroxy-3β-methyloct-1-yl)cyclopent-1α-yl]acetic acid, γ-lactone.

EXAMPLE XXIX

The compound of Example XXXIX may be converted by the process of Example XXVII to 2-[5α-hydroxy-3α-(tetrahydropyran-2-yloxy)-2β-(3β-methyl-3α-(tetrahydropyran-2-yloxy)oct-1-yl)cyclopent-1α-yl]acetic acid, γ-lactone and 2-[5α-hydroxy-3α-(tetrahydropyran-2-yloxy)-2β-(3α-methyl-3β-(tetrahydropyran-2-yloxy)oct-1-yl)cyclopent-1α-yl]acetic acid, γ-lactone which may be converted by the process of Example XL to 2-[5α-hydroxy-3α-(tetrahydropyran-2-yloxy)-2β-(3β-methyl-3α-(tetrahydropyran-2-yloxy)oct-1-yl)cyclopent-1α-yl]acetaldehyde, γ-hemiacetal and 2-[5α-hydroxy-3α-(tetrahydropyran-2-yloxy)-2β-(3α-methyl-3β-(tetrahydropyran-2-yloxy)oct-1-yl)cyclopent-1α-yl]acetaldehyde, γ-hemiacetal.

EXAMPLE XXX

A mixture of 23.5 g. (0.25 mole) of methanesulfonamide and 49.8 g. (0.25 mole) of 5-bromovaleric acid chloride was heated at 80-85° (oil bath) for 45 minutes. The brown reaction mixture was allowed to cool and was dissolved in ethyl acetate. The organic solution was washed with water and saturated brine, was dried (anhydrous magnesium sulfate), was Darcoed, concentrated, and cooled to afford the white, crystalline N-methanesulfonyl-5-bromovaleramide weighing 48.2 g. (74.8% yield) which melted at 97°–98°.

The nmr spectrum (CDCl$_3$) showed a broad singlet at 4.26–3.95 δ for the N—H, a multiplet at 3.66–3.23 for the —$CH_2$Br, a singlet at 3.31 δ for the $SO_2$—$CH_3$, a multiplet at 2.63–2.20 δ for the —$CH_2$CO, and a multiplet at 2.12–1.52 δ for the $CH_2$–$CH_2$. The ir spectrum ($CHCl_3$) showed a strong absorption at 1720 $cm^{-1}$ attributable to the carbonyl group.

A solution of 48.2 g. (0.187 mole) of the N-methanesulfonyl-5-bromovaleramide, prepared as above, 53.8 g. (0.206 mole) of triphenylphosphine, and 120 ml. of xylene was heated to reflux under nitrogen for 2 hours. The solution was then let cool to room temperature and the resultant solid collected by filtration. Recrystallization of the crude solid from methylene chloride: ethyl acetate afforded the white, crystalline [(4-methanesulfonylaminocarbonyl)butyl]triphenylphosphonium bromide weighing 42.5 g. (43.8% yield) melting at 188°–190°.

The ir spectrum (KBr) of the product exhibited a strong absorption at 5.85 μ attributable to the carbonyl group. The nmr spectrum ($CDCl_3$) exhibited a complex multiplet at 8.14–7.27 δ for the aromatic protons, a multiplet at 4.00–3.30 δ for the -$CH_2$P, a singlet at 3.12 δ for the -$SO_2CH_3$, a multiplet at 3.00–2.38 δ for the $CH_2$CO, and a multiplet at 2.23–1.38 δ for the $CH_2CH_2$. A titration of the solid product indicated the pKa ½ to be 5.25.

The above product may be caused to react with the known 2-[5α-hydroxy-3α-(tetrahydropyran-2-yloxy)-2β-(3α-(tetrahydropyran-2-yloxy)-trans-1-cis-5-octadien-1-yl)cyclopent-1α-yl]acetaldehyde, γ-hemiacetal (E. J. Corey, et al., J. Am. Chem. Soc., 93, 1490 (1971) to produce N-methanesulfonyl-9α-hydroxy-11α,15α-bis-(tetrahydropyran-2-yloxy)-cis-5-trans-13-cis-17-prostatrienamide which may be converted by known reactions (E. J. Corey, ibid) into the N-methanesulfonyl prostaglandin $F_3$ $_α$ carboxamide or the N-methanesulfonyl prostaglandin $E_3$ carboxamide.

The above product may be caused to react with the 2-[3α,5α-dihydroxy-2β-(3α-hydroxyoct-1-yl)cyclopent-1α-yl]acetaldehyde, γ-hemiacetal prepared in Example XXVI to produce the N-methanesulfonyl 13,14-dihydroprostaglandin $F_2$ $_α$ carboxamide.

The above product may be caused to react with the 2-[5α-hydroxy-3α-(tetrahydropyran-2-yloxy)-2β-(3α-(tetrahydropyran-2-yloxy)oct-1-yl)cyclopent-1α-yl]acetaldehyde, γ-hemiacetal prepared in Example XXVII to produce N-methanesulfonyl-9α-hydroxy-11α,15α-bis-(tetrahydropyran-2-yloxy)-cis-5-prostenamide called Compound A. Compound A may be hydrolyzed as described in Example III to produce the N-methanesulfonyl-13,14-dihydroprostaglandin $F_2$ $_α$ carboxamide. Compound A may be subjected to oxidation as described in Example IV followed by hydrolysis as described in Example V to produce the N-methanesulfonyl 13,14-dihydroprostaglandin $E_2$ carboxamide. The latter may be dehydrated as described in Example VI to produce the N-methanesulfonyl 13,14-dihydroprosaglandin $A_2$ carboxamide or reduced as described in Example XXXVI to produce the N-methanesulfonyl 13,14-dihydroprostaglandin $F_2$ $_β$ carboxamide.

The above product may be caused to react with the mixed 2-[5α-hydroxy-3α-(tetrahydropyran-2-yloxy)-2β-(3β-methyl-3α-(tetrahydropyran-2-yloxy)oct-1-yl)cyclopent-1α-yl]acetaldehyde, γ-hemiacetal and 2-[5α-hydroxy-3α-(tetrahydropyran-2-yloxy)-2β-(3α-methyl-3β-(tetrahydropyran-2-yloxy)oct-1-yl)cyclopent-1α-yl]acetaldehyde, γ-hemiacetal prepared in Example XXIX to produce N-methanesulfonyl-9α-hydroxy-15-methyl-11α,15-bis(tetrahydropyran-2-yloxy)-cis-5-prostenamide called Compound B. Compound B may be hydrolyzed as described in Example III to produce the N-methanesulfonyl 15-methyl-13,14-dihydroprostaglandin $F_2$ $_α$ carboxamide. Compound B may be subjected to oxidation as described in Example IV followed by hydrolysis as described in Example V to produce the N-methanesulfonyl 15-methyl-13,14-dihydroprostaglandin $E_2$ carboxamide. The latter may be dehydrated as described in Example VI to produce the N-methanesulfonyl 15-methyl-13,14-dihydroprostaglandin $A_2$ carboxamide or reduced as described in Example XXXVI to produce the N-methanesulfonyl 15-methyl-13,14-dihydroprostaglandin $F_2$ $_β$ carboxamide.

The above product may be caused to react with the 2-[5α-hydroxy-3α-(tetrahydropyran-2-yloxy)-2β-(3β-(tetrahydropyran-2-yloxy)oct-1-yl)cyclopent-1α-yl]acetaldehyde, γ-hemiacetal prepared in Example XXIII to produce N-methanesulfonyl-9α-hydroxy-11α,15β-bis-(tetrahydropyran-2-yloxy)-cis-5-prostenamide called Compound C. Compound C may be hydrolyzed as described in Example III to produce the N-methanesulfonyl 15-epi-13,14-dihydroprostaglandin $F_2$ $_α$ carboxamide. Compound C may be subjected to oxidation as described in Example IV followed by hydrolysis as described in Example V to produce the N-methanesulfonyl 15-epi-13,14-dihydroprostaglandin $E_2$ carboxamide. The latter may be dehydrated as described in Example VI to produce the N-methanesulfonyl 15-epi-13,14-dihydroprostaglandin $A_2$ carboxamide or reduced as described in Example XXXVI to produce the N-methanesulfonyl 15-epi 13,14-dihydroprostaglandin $F_2$ $_β$ carboxamide.

The above product may be caused to react with the 2-[5α-hydroxy-3α-(tetrahydropyran-2-yloxy)-2β-(3β-(tetrahydropyran-2-yloxy)-1-trans-octen-1-yl)cyclopent-1α-yl]acetaldehyde, γ-hemiacetal prepared in Example XXIV to produce N-methanesulfonyl-9α-hydroxy-11α,15β-bis-(tetrahydropyran-2-yloxy)-cis-5-trans-13-prostadienamide called Compound D. Compound D may be hydrolyzed as described in Example III to produce the N-methanesulfonyl 15-epi-prostaglandin $F_2$ $_α$ carboxamide. Compound D may be subjected to oxidation as described in Example IV followed by hydrolysis as described in Example V to produce the N-methanesulfonyl-15-epi-prostaglandin $E_2$ carboxamide. The latter may be dehydrated as described in Example VI to produce the N-methanesulfonyl-15-epi-prostaglandin $A_2$ carboxamide or reduced as described in Example XXXVI to the N-methanesulfonyl-15-epi-prostaglandin $F_2$ $_β$ carboxamide.

The above product may be caused to react with the 2-[3α,5α-dihydroxy-2β-(3β-hydroxy-trans-1-octen-1-yl)cyclopent-1α-yl]acetaldehyde, γ-hemiacetal prepared in Example XXI to provide the N-methanesulfonyl prostaglandin $F_2$ $_α$ carboxamide.

The above product may be caused to react with the 2-[3α,5α-dihydroxy-2β-(3β-hydroxyoct-1-yl)cyclopent-1α-yl]acetaldehyde, γ-hemiacetal prepared in Example XXI to provide the N-methanesulfonyl 13,14-dihydroprostaglandin $F_2$ $_α$ .

The above product may be caused to react with the 2-[3α,5α-dihydroxy-2β-(3α-hydroxy-3β-methyl-trans-1-octen-1-yl)cyclopent-1α-yl]acetaldehyde, γ-hemiacetal prepared in Example XXXVII to provide the N-methanesulfonyl 15-methylprostaglandin $F_2$ $_α$ carboxamide.

The above product may be caused to react with the 2-[3α,5α-dihydroxy-2β-(3α-hydroxy-3β-methyloct-1-yl)cyclopent-1α-yl]acetaldehyde, γ-hemiacetal prepared in Example XXXVII to provide the N-methanesulfonyl 15-methyl-13,14-dihydroprostaglandin $F_{2\alpha}$.

EXAMPLE XXXI

To a solution of the phosphonium bromide of Example XXX (10.4 g.; 20.0 mmoles) in 12.0 ml. of dry dimethyl sulfoxide was added dropwise 21.8 ml. (39.0 mmoles) of a 1.8 M solution of sodium methylsulfinylmethide in dry dimethyl sulfoxide. The resultant red ylide solution was stirred under nitrogen for 5 minutes then a solution of 2.19 g. (5.0 mmoles) of the known 2-[5α-hydroxy-3α-(tetrahydropyran-2-yloxy)-2β-[3α-(tetrahydropyran-2-yloxy)-trans-1-octen-1-yl]cyclopent-1α-yl]acetaldehyde, γ-hemiacetal in 5.0 ml. of dry dimethyl sulfoxide was added dropwise over a period of 30 minutes. The solution was stirred overnight then was poured onto a mixture of ether:ice-water. The vigorously stirred solution was acidified to pH ~ 3 with 10% aqueous hydrochloric acid. The acidified aqueous layer was extracted with ether and the combined ethereal extracts were dried (anhydrous magnesium sulfate) and concentrated to afford a crude yellow oil. The oil was purified by column chromatography on silica gel (Mallinckrodt CC-4) using mixtures of benzene:chloroform as eluents. After removal of less polar impurities the colorless, oily N-methanesulfonyl-9α-hydroxy-11α,15α-bis-(tetrahydropyran-2-yloxy)-cis-5-trans-13-prostadienamide was collected weighing 2.59 g. (86.4% yield).

The nmr spectrum (CDCl$_3$) of the product exhibited a multiplet at 5.70–5.13 δ attributable to the olefinic protons, a broad singlet at 4.80–4.52 δ attributable to the OCHO, multiplets at 4.30–3.00 δ attributable to the CHO and CH$_2$O, a singlet at 3.22 δ attributable to the SO$_2$CH$_3$, and multiplets at 2.75–0.68 δ for the remaining protons.

The above product may be subjected to catalytic reduction to produce N-methanesulfonyl-9α-hydroxy-11α,15α-bis-(tetrahydropyran-2-yloxy)-trans-13-prostenamide which may be converted by known reactions (E. J. Corey, et al., *J. Am. Chem. Soc.*, 92, 2586 (1970)) to N-methanesulfonyl prostaglandin $F_{1\alpha}$ carboxamide or N-methanesulfonyl prostaglandin $E_1$ carboxamide. The latter may be converted by known reactions (Example VI) to N-methanesulfonyl prostaglandin $A_1$ carboxamide or (Example XXXVI) to the N-methanesulfonyl prostaglandin $F_{1\beta}$ carboxamide.

The above product may be subjected to catalytic reduction to produce the N-methanesulfonyl-9α-hydroxy-11α,15α-bis-(tetrahydropyran-2-yloxy)prostanamide called Compound A. Compound A may be hydrolyzed as described in Example III to produce the N-methanesulfonyl-13,14-dihydroprostaglandin $F_{1\alpha}$ carboxamide. Compound A may be subjected to oxidation as described in Example IV followed by hydrolysis as described in Example V to produce the N-methanesulfonyl-13,14-dihydroprostaglandin $E_1$ carboxamide called Compound B. Compound B may be dehydrated as described in Example VI to produce the N-methanesulfonyl-13,14-dihydroprostaglandin $A_1$ carboxamide or reduced as described in Example XXXVI to produce the N-methanesulfonyl-13,14-dihydroprostaglandin $F_{1\beta}$ carboxamide.

EXAMPLE XXXII

A solution of 3.16 g. of the bis-THP ether of Example XXXI and 32 ml. of a 65:35 mixture of acetic acid:water was stirred at room temperature overnight under nitrogen. The solution was then concentrated and the resultant oil was purified by column chromatography on silica gel (SilicAR CC-7) using mixtures of chloroform:ethyl acetate as eluents. After removal of less polar impurities crystalline N-methanesulfonyl-9α,11α,15α-trihydroxy-cis-5-trans-13-prostadienamide, the N-methanesulfonylprostaglandin $F_{2\alpha}$ carboxamide weighing 1.14 g. was collected which melted at 121°–121.5° (from ethyl acetate:ether).

The ir spectrum (CHCl$_3$) exhibited strong absorptions at 1720 cm$^{-1}$ for the carbonyl groups and 970 cm$^{-1}$ for the trans double bond. The mass spectrum showed peaks for loss of one, two, and three molecules of water and a peak for loss of H$_2$O + C$_5$H$_{11}$.

The above product may be catalytically reduced as described in Example VII to provide the N-methanesulfonyl 13,14-dihydroprostaglandin $F_{1\alpha}$ carboxamide.

EXAMPLE XXXIII

To a solution of 2.48 g. of the alcohol of Example XXXI in 14 ml. of acetone cooled to −15° under nitrogen was added 1.70 ml. of Jones' reagent. The mixture was stirred in the cold for 20 minutes then was quenched in the cold by the addition of 1.70 ml. of isopropanol. The mixture was diluted with ethyl acetate; the diluted solution was washed with water (2X) and with saturated brine (IX), was dried (anhydrous magnesium sulfate), and was concentrated to afford the oily, colorless N-methanesulfonyl-9-oxo-11α-bis-(tetrahydropyran-2-yloxy)-cis-5-trans-13-prostadienamide weighing 2.45 g. (98.6% yield) which was used without purification.

EXAMPLE XXXIV

A solution of 2.45 g. of the bis-THP ether of Example XXXIII in 24 ml. of a 65:35 mixture of acetic acid:water was heated to 40±2° under nitrogen for 6 hours. The mixture was then concentrated and the resultant oily product was purified by column chromatography on silica gel (SilicAR CC-4) using mixtures of chloroform:ethyl acetate as eluents. After removal of less polar impurities the solid N-methanesulfonylprostaglandin $E_2$ carboxamide weighing 865 mg. (49.2% yield) which melted at 118.5–119° (from acetone:hexane).

The ir spectrum (CHCl$_3$) of the crystalline product exhibited absorptions at 1720 cm$^{-1}$ for the imide carbonyl, at 1730 cm$^{-1}$ for the ketone carbonyl, and at 970 cm$^{-1}$ for the trans double bond. The nmr spectrum (CDCl$_3$) of the crystalline product showed a multiplet at 5.70–5.44 δ for the trans olefin, multiplet at 5.44–5.18 δ for the cis olefin, a multiplet at 4.33–3.80 δ for the CH-OH, a singlet at 3.23 δ for the SO$_2$CH$_3$ and multiplets at 2.78–1.65 δ for the remaining protons.

Anal: Calc'd for C, 58.72; H, 8.21; N, 3.26; S, 7.46. Found C, 59.01; H, 8.12; N, 3.19; S, 7.54.

The above product may be dehydrated as described in Example VI to provide the N-methanesulfonyl prostaglandin $A_2$ carboxamide.

EXAMPLE XXXV

A heterogeneous mixture of 50 mg. (0.116 mmole) of the product of Example XXXIV and 10 mg. of 5% palladium on carbon in 5 ml. of absolute methanol was stirred at room temperature under one atmosphere of hydrogen for 1.5 hours. The mixture was then filtered through a pad of Celite and the filtrate was concentrated to afford the crystalline N-methanesulfonyl-9-oxo-11α,15α-dihydroxyprostanamide weighing 38 mg. and melting at 91°–93°.

The ir spectrum (film) of the product exhibited a strong absorption at 1735 and 1720 cm$^{-1}$ for the carbonyl groups and no absorption for the trans double bond. The nmr spectrum (CD$_3$OD) exhibited no olefinic resonances, multiplets at 4.34–3.90 δ and 3.80–3.48 δ for the C<u>H</u>O, a singlet at 3.15 δ for the SO$_2$CH$_3$, and multiplets at 2.97–0.78 δ for the remaining protons.

The above product may be dehydrated as described in Example VI to provide the N-methanesulfonyl 13,14-dihydroprostaglandin A$_1$ carboxamide or reduced as described in Example XXXVI to provide the N-methanesulfonyl 13,14-dihydroprostaglandin F$_{1\ \beta}$ carboxamide.

EXAMPLE XXXVI

To a solution, cooled in ice, of 100 mg. (0.234 mmole) of the product of Example XXXIV in 10 ml. of absolute methanol was added an ice-cooled solution of 300 mg. of sodium borohydride in 35 ml. of absolute methanol. The solution was stirred at 0°–5° under nitrogen for 20 minutes then the reaction was quenched by the addition of 2 ml. of water. The methanol was removed by rotary evaporation and the resultant aqueous solution was acidified to pH ∼ 3 with 10% hydrochloric acid. The acidified aqueous layer was extracted with ethyl acetate (5 × 10 ml.). The combined organic extracts were washed with water and saturated brine, were dried (anhydrous magnesium sulfate) and were concentrate to afford a white foam. Purification of the crude product by silica gel chromatography (Mallinckrodt CC-7) using mixtures of methanol in methylene chloride as eluents afforded first the crystalline N-methanesulfonyl-9α,11α,15α-trihydroxy-5-cis-13trans-prostadienamide then the crystalline N-methanesulfonyl9β-11α,15α-trihydroxy-5-cis-13 -trans-prostadienamide weighing 45 mg. and melting at 138°–139.5°.

The ir spectra (KBr) of both crystalline products were virtually identical.

EXAMPLE XXXVII

To a solution cooled to −78° of 2.68 g. (6.00 mmoles) of 2-[3α-p-phenylbenzoyloxy-5α-hydroxy-2β-[3-oxo-trans-1-octen-1-yl]cyclopent-1α-yl]acetic acid, γ-lactone, a known compound (see *JACS*, 93, 1491 (1971), in 26 ml. of anhydrous ether (Mallinckrodt) and 20 ml. of tetrahydrofuran (distilled from lithium aluminum hydride) was added dropwise 6.5 ml. (6.00 mmoles) of a 0.92 N solution of methyllithium in ether (Alfa). After being stirred at −78° for 15 minutes the reaction was quenched by the dropwise addition of glacial acetic acid until the pH of the reaction was approximately 7. The mixture was then diluted with methylene chloride and the diluted organic solution was washed with water (IX) and with saturated brine (IX), was dried (anhydrous magnesium sulfate), and was concentrated to afford 2.71 g. of the viscous, oily epimeric alcohols (97.8% yield).

The crude product was purified by column chromatography on 108 g. of silica gel (Baker 'Analyzed' Reagent 60-200 mesh) using a mixture of benzene:ethyl acetate as eluent. After elution of higher R$_f$ impurities, the desired mixture of epimers, 2-[3α-p-biphenylcarboxy-5α-hydroxy-2β-[3α-hydroxy-3β-methyl-trans-1-octen-1-yl]cyclopent-1α-yl]acetic acid, γ-lactone and 2-[3α-p-biphenylcarboxyl-5α-hydroxy-2β-[3β-hydroxy-3β-hydroxy-3α-methyl-trans-1-octen-1-yl] cyclopent-1α-yl]acetic acid, γ-lactone was eluted weighing 0.853 g. (30.8% yield). The epimeric product may be separated by thin layer or liquid-liquid chromatography.

The ir spectrum (CHCl$_3$) of the product exhibited strong absorptions at 1710 cm$^{-1}$ for the ester carbonyl and 1770 cm$^{-1}$ for the lactone carbonyl. The nmr spectrum (CDCl$_3$) of the product showed a multiplet at 7.28–8.22 δ for the aromatic protons, a multiplet at 5.56–5.77 δ for the olefinic protons, a multiplet at 4.90–5.45 δ for the —C<u>H</u>OCO—, a singlet at 1.27 δ (—C<u>H</u>$_3$), and multiplets at 0.57–3.10 δ for the remaining protons.

The above product may be reduced as described in Example XXV to prepare the 2-[3α,5α-dihydroxy-2β-(3β-hydroxy-3α-methyl-trans-1-octen-1-yl)cyclopent-1α-yl]acetaldehyde, γ-hemiacetal and 2-[3α,5α-dihydroxy-2β-(3α-hydroxy-3β-methyl-trans-1-octen-1-yl)cyclopent-1α-yl]acetaldehyde, γ-hemiacetal.

The above product may also be catalytically hydrogenated as described in Example XXVI and then reduced as described in Example XXV to prepare the 2-[3α,5α-dihydroxy-2β-(3β-hydroxy-3α-methyloct-1-yl)cyclopent-1α-yl]acetaldehyde, γ-hemiacetal and 2-[3α,5α-dihydroxy-2β-(3α-hydroxy-3β-methyloct-1-yl)cyclopent1α-yl]acetaldehyde, γ-hemiacetal.

EXAMPLE XXXVIII

A heterogeneous mixture of 1.30 g. (2.81 mmoles) of the chromatographed ester of Example XXXVII, 25 ml. of methanol, and 0.388 g. (2.81 mmoles) finely powdered anhydrous potassium carbonate was stirred under nitrogen for 2.0 hours at room temperature then was cooled in ice. To the cooled solution was added 5.60 ml. (5.60 mmoles) of 1.0 N hydrochloric acid. The cold, acidified solution was stirred for 10 minutes then was diluted with 25 ml. of saturated brine. After filtration of the resultant solids the filtrate was extracted with ethyl acetate (3X). The combined ethyl acetate extracts were washed with water (IX), were dried (anhydrous magnesium sulfate), and were concentrated to afford 0.744 g. (94.0% yield) of yellow, oily diol, 2-[3α,5α-dihydroxy-2β-(3α-hydroxy-3β-methyl-trans-1-octen-1-yl)cyclopent-1α-yl]acetic acid, γ-lactone and 2-[3α,5α-dihydroxy-2β-(3β-hydroxy-3α-methyl-trans-1-octen-1-yl)cyclopent-1α -yl]acetic acid, γ-lactone.

This oil was purified by column chromatography on silica gel (Baker "Analyzed" Reagent 60–200 mesh) using a 1:1 mixture of methylene chloride:ethyl acetate as eluent. After elution of higher R$_f$ impurities 0.507 g. of the desired diols were collected (64.0% yield).

The ir spectrum (CHCl$_3$) of the diols exhibited a strong absorption at 1770 cm$^{-1}$ for the lactone carbonyl. The nmr spectrum (CDCl$_3$) of the diol products exhibited a multiplet at 5.46–5.70 δ for the olefinic protons, a multiplet at 4.75–5.14 δ for the HO—C<u>H</u>, a multiplet at 3.75–4.21 δ for the <u>H</u>COCO—, a singlet at 1.26 δ for the —C<u>H</u>$_3$, and multiplets at 0.68–3.11 δ for the remaining protons.

EXAMPLE XXXIX

To a solution, cooled in ice, of 0.507 g. (1.80 mmole) of the chromatographed diol of Example XXXVIII in 5.4 ml. of methylene chloride was added 0.54 ml. of dihydropyran (distilled from lithium aluminum hydride), and 18 mg. of p-toluenesulfonic acid monohydrate. The solution was stirred in the cold for 15 minutes then was diluted with ether. The organic solution was washed with saturated sodium bicarbonate (1 X), was dried (anhydrous magnesium sulfate), and was concentrated to afford 0.870 g. (>100% yield) of the pale yellow, oily bis-THP ethers 2-[5α-hydroxy-3α-(tetrahydropyran-2-yloxy)-2β-(3β-methyl-3β-(tetrahydropyran-2-yloxy)-trans-1-octen-1-yl)cyclopent-1α-yl]acetic acid, γ-lactone and 2-[5α-hydroxy-3α-(tetrahydropyran-2-yloxy)-2β-(3α-methyl-3β-(tetrahydropyran-2-yloxy)-trans-1-octen-1-yl)cyclopent-1α-yl]acetic acid, γ-lactone, which was used without further purification. The structure of the product was substantiated by the virtual identity of its ir spectrum with that of the known 15-normethyl compound (see JACS, 92, 397 (1970).

EXAMPLE XL

To a solution cooled to $-78°$ of 0.810g. (1.80 mmoles) of the crude bis-THP ether lactone of Example XXXIX in toluene was added 2.3 ml. (1.85 mmoles) of a 0.805 M solution of diisobutylaluminum hydride in hexane (Alfa). The solution was stirred at $-78°$ for 15 minutes then was quenched by the dropwise addition of methanol until gas evolution ceased. The quenched mixture was warmed to room temperature then was concentrated. The resultant oil was dissolved in ether and the ethereal solution was washed with a 50% sodium potassium tartrate solution (2X) and with saturated brine (1X), was dried (anhydrous magnesium sulfate), and was concentrated to afford 0.800 g. (98.5% yield) of the oily hemiacetals 2-[5α-hydroxy-3α-(tetrahydropyran-2-yloxy)-2β-(3β-methyl-3α-(tetrahydropyran-2-yloxy)-trans-1-octen-1-yl)cyclopent-1α-yl]acetaldehyde, γ-hemiacetal and 2-[5α-hydroxy-3α-(tetrahydropyran-2-yloxy)-2β-(3α-methyl-3β-(tetrahydropyran-2-yloxy)-trans-1-octen-1-yl)cyclopent-1α-yl]acetaldehyde, γ-hemiacetal.

The oil was purified by column chromatography on silica gel (Baker 'Analyzed' Reagent 60–200 mesh) using first benzene as eluent to remove high $R_f$ impurities than a 2:1 mixture of benzene:ethyl acetate to elute the colorless, oily product weighing 0.601 g. (74.0% yield). The structure was confirmed by the virtual identity of its ir spectrum with that of the known 15-normethyl compound (see JACS,92, 397 (1970).

EXAMPLE XLI

To a solution of the phosphonium bromide of Example XXX (2.68 g., 5.1 mmoles which was dried overnight at 144°) in 5 ml. of dry dimethyl sulfoxide was added dropwise 6.22 ml. (9.7 mmoles) of a 1.56 M solution of sodium methylsulfinylmethide in dry dimethyl sulfoxide. The resultant red ylide solution was stirred under nitrogen for 15 minutes then a solution of 770 mg. (1.50 mmoles) of the product of Example XL in 2 ml. of dry dimethyl sulfoxide was added. The mixture was stirred under nitrogen overnight then was poured onto a mixture of ice water:ether. The aqueous layer was acidified with 10% aqueous hydrochloride acid then was extracted with ethyl acetate (3X). The combined organic extracts were dried (anhydrous magnesium sulfate) and were concentrated to afford a crude yellow oil which was purified by silica gel (Baker 'Analyzed' 60-200 mesh) column chromatography using mixtures of chloroform:ethyl acetate as eluents. After elution of less polar impurities the oily products N-methanesulfonyl-9α-hydroxy-11α,15α -bis-(tetrahydropyran-2-yloxy)-15β-methyl-cis-5-trans-13-prostadienamide and N-methanesulfonyl-9α-hydroxyl1-1α,15β-bis-(tetrahydropyran-2-yloxy)-15α-methyl-cis-d5-trans-13-prostadienamide were collected weighing 300 mg.

The nmr spectrum ($CDCl_3$) of the chromatographed product exhibited a multiplet at 5.60-5.09 δ for the olefinic protons, a broad singlet at 4.74-4.44 δ for the OCHO, multiplets at 4.21-3.92 δ for the $CH_2O$ and CHO, a singlet at 3.24 δ for the $SO_2CH_3$, two singlets at 1.30 and 1.11 δ for the C—$CH_3$, and multiplets at 2.67 -0.56 δ for the remaining protons.

The above product may also be subjected to catalytic reduction to produce N-methanesulfonyl-9α-hydroxy-11α,15-bis-(tetrahydropyran-2-yloxy)-15-methyl-trans-13-prostenamides which may be converted by known reactions (E. J. Corey, et al., *J. Am. Chem. Soc.*, 92, 2586 (1970) to N-methanesulfonyl 15-methyl prostaglandin $F_{1\alpha}$ carboxamide or N-methanesulfonyl 15-methyl prostaglandin $E_1$ carboxamide. The latter may be converted by known reactions (Example VI) to N-methanesulfonyl 15-methyl prostaglandin $A_1$ carboxamide or reduced as described in Example XXXVI to N-methanesulfonyl 15-methyl prostaglandin $F_{1\beta}$ carboxamide.

The above product may be subjected to catalytic reduction to produce the N-methanesulfonyl-9α-hydroxy-11α,15-bis-(tetrahydropyran-2-yloxy)-15-methyl-prostanamide called Compound A. Compound A may be hydrolyzed as described in Example III to produce the N-methanesulfonyl-15-methyl 13,14-dihydroprostaglandin $F_{1\alpha}$ carboxamide. Compound A may be subjected to oxidation as described in Example IV followed by hydrolysis as described in Example V to produce the N-methanesulfonyl-15-methyl-13,14-dihydroprostaglandin $E_1$ carboxamide called Compound B. Compound B may be dehydrated as described in Example VI to produce the N-methanesulfonyl-15-methyl-13,14-dihydroprostaglandin $A_1$ carboxamide or reduced as described in Example XXXVI to produce the N-methanesulfonyl-15-methyl-13,14-dihydroprostaglandin $F_{1\beta}$ carboxamide.

The above product may also be hydrolyzed as described in Example III to provide the N-methanesulfonyl 15-methyl-prostaglandin $F_{2\alpha}$ carboxamide which may be catalytically hydrogenated as described in Example VII to provide the N-methanesulfonyl 15-methyl-13,14-dihydroprostaglandin $F_{1\alpha}$ carboxamide.

EXAMPLE XLII

To a solution, cooled to $-15°$, of 0.600 g. (0.98 mmole) of the bis-THP ethers of Example XLI in 11 ml. of acetone was added 0.83 ml. of Jones' reagent. The mixture was stirred under nitrogen in the cold for 20 minutes then was quenched by the addition of 0.83 ml. of isopropanol. The mixture was stirred for an additional 5 minutes then was diluted with ethyl acetate. The organic layer was washed with water (2X) and saturated brine (1X), was dried (anhydrous magnesium sulfate), and was concentrated to afford the crude, oily N-methanesulfonyl-9-oxo-11α,15α-bis-(tetrahydropyran-2-yloxy)-15β-methyl-cis-5-trans-13-prostadienamide and N-methanesulfonyl-9-oxo-11α,15β-bis(tetrahydropyran-2-yloxy)-15α-methyl-cis-5-trans-13-prostadienamide weighing 523 mg. (87.1%) which was used without purification.

EXAMPLE XLIII

A solution of 523 mg. (0.855 mmole) of the crude bis-THP ethers of Example XLII in 5.0 ml. of a 65:35 mixture of acetic acid-water was stirred under nitrogen at room temperature overnight then was concentrated. The crude oily product was purified by silica gel column chromatography (Mallinckrodt CC-7) using mixtures of chloroform:ethyl acetate as eluents. After elution of less polar impurities the colorless oily N-methanesulfonyl-9-oxo-11α,15α-dihydroxy-15β-methyl-5-cis-13-trans-prostadienamide and N-methanesulfonyl-9-oxo-11α,15β-dihydroxy-15α-methyl-5-cis-13-trans-prostadienamide was collected weighing 159 mg. (42.0% yield).

The nmr spectrum (CDCl$_3$) of the product exhibited a multiplet at 5.72–5.49 δ for the trans double bond, a multiplet at 5.49–5.12 δ for the cis double bond, a multiplet at 4.37–3.48 δ for the CHO, a singlet at 3.26 δ for the SO$_2$CH$_3$, and multiplets at 2.74–0.63 δ for the remaining protons.

The mass spectrum showed an m/e at 443 for the parent molecule, a m/e at 425 for M—H$_2$O, and an m/e at 407 for m—2H$_2$O.

The above product may be dehydrated as described in Example VI to produce the N-methanesulfonyl 15-methyl prostaglandin A$_2$ carboxamide or reduced as described in Example XXXVI to produce the N-methanesulfonyl 15-methyl prostaglandin F$_2$ $\beta$ carboxamide.

The above product may be catalytically reduced as described in Example VII to provide the N-methanesulfonyl 15-methyl-13,14-dihydroprostaglandin E$_1$ carboxamide. The latter may be dehydrated as described in Example VI to provide the N-methanesulfonyl 15-methyl-13,14-dihydroprostaglandin A$_1$ carboxamide or reduced as described in Example XXXVI to provide the N-methanesulfonyl 15-methyl-13,14-dihydroprostaglandin F$_1$ $\beta$ carboxamide.

EXAMPLE XLIV

Dimethyl 2-Oxo-3,3-dimethylheptylphosphonate:

A solution of 18.4 g. (0.116 moles) dimethyl methylphosphonate (Aldrich) in 200 ml. dry tetrahydrofuran is cooled to −78° in a dry nitrogen at atmosphere. To the stirred phosphonate solution is added 67.3 ml. (127.8 mmoles) of 1.90 M n-butyllithium in hexane solution (Alfa Inorganics, Inc.) dropwise over a period of 40 minutes at such a rate that the reaction temperature never rose above −65°. After an additional 5 minutes stirring at −78°, 10.2 g. (58.1 mmoles) methyl 2,2-dimethylhexanoate in 10 ml. of tetrahydrofuran is added dropwise at a rate that kept the reaction temperature less than −70° (20 minutes). After 1.0 hour at −78° the reaction mixture is allowed to warm to ambient temperature, neutralized with 10 ml. acetic acid and rotary evaporated to a white gel. The gelatinous material is taken up in 75 ml. water, the aqueous phase extracted with 100 ml. portions of chloroform (3x), the combined organic extracts are backwashed (50 cc H$_2$O), dried (MgSO$_4$), and concentrated (water aspirator) to a crude residue and distilled (b.p. 80°–85° at 0.05 mm) to give dimethyl 2-oxo-3,3-dimethylheptylphosphonate.

The nmr spectrum (CDCl$_3$) of the distilled product exhibited a doublet centered at 3.78 δ (J = 11 cps) for the OC$\underline{H}_3$, a doublet centered at 3.09 δ (J = 23 cps) for the COC$\underline{H}_2$P, a singlet at 1.10 δ for the gem dimethyl groups, and multiplets at 1.60–0.71 δ for the remaining protons.

EXAMPLE XLV

To a suspension, under nitrogen, of 1.32 g. (31.5 mmoles) of sodium hydride (56.6% dispersion in mineral oil) in 400 ml. of dry dimethoxyethane was added dropwise 8.60 g. (34.4 mmoles) of the product of Example XLIV. The solution was stirred for 1.0 hour then a slurry of 10.0 g. (28.6 mmoles) of the known 2-[3α-p-phenylbenzoyloxy-5α-hydroxy-2β-formylcyclopent-1α-yl]acetic acid, γ-lactone in 80 ml. of dry dimethoxyethane. The mixture was stirred for 1.0 hour then was neutralized (pH ∼ 7) by the addition of glacial acetic acid. The neutralized reaction was concentrated by rotary evaporation to afford a brown solid. This solid was dissolved in methylene chloride, was washed with water and brine, was dried (anhydrous magnesium sulfate), Darcoed, and concentrated to afford after recrystallization from ethanol the desired 2-[3α-p-phenylbenzoyloxy-5α-hydroxy-2β-(3-oxo-4,4-dimethyl-trans-1-octen-1-yl)cyclopent-1α-yl]acetic acid, γ-lactone weighing 7.67 g. (55.6% yield).

The ir spectrum (CHCl$_3$) of the crystalline product exhibited a strong absorption at 1775 cm$^{-1}$ for the lactone carbonyl, a strong absorption at 1715 cm$^{-1}$ for the ester carbonyl, medium absorptions at 1685 and 1625 cm$^{-1}$ for the ketone carbonyl, and a medium absorption at 975 cm$^{-1}$ for the trans double bond. The nmr spectrum (CDCl$_3$) of the product exhibited multiplets at 8.18–7.20 δ for the aromatic protons, a multiplet at 6.74–6.60 δ for the vinyl protons, a multiplet at 5.46–4.91 δ for the CHO, multiplets at 3.08–2.23 δ for the COCH$_2$, a singlet at 1.07 δ for the gem dimethyl groups, and multiplets at 1.70–0.52 δ for the remaining protons.

Anal. Calc'd for C, 75.92; H, 7.22; Found: C, 75.67; H, 7.37

EXAMPLE XLVI

To a solution, cooled to −78° under nitrogen, of 15.1 g. (31.8 mmoles) of the product of Example XLV in 250 ml. of dry tetrahydrofuran was added dropwise 77 ml. (31.8 mmoles) of a 0.413 M solution of lithium tri-sec-butylborohydride in tetrahydrofuran. The mixture was stirred for 45 minutes at −78° then was quenched in the cold by the addition of 100 ml. of a 9:1 mixture of water:glacial acetic acid. The quenched solution was let warm to room temperature then the tetrahydrofuran was removed by rotary evaporation. The resultant biphasal mixture was diluted with water then was extracted with methylene chloride. The combined organic extracts were washed with saturated sodium bicarbonate, were dried (anhydrous magnesium sulfate), and were concentrated to afford a crude oil. Purification of the oil by silica gel chromatography (Baker "Analyzed" 60-200 mesh) using 2% ether in methylene chloride as eluent afforded after removal of less polar impurities the desired 2-[3α-p-phenylbenzoyloxy-5α-hydroxy-2β -(3α-hydroxy-4,4-dimethyl-trans-1-octen-1-yl)cyclopent-1α-yl]acetic acid, γ-lactone as a colorless waxy solid weighing 2.26 g. (15.0% yield) and 2-[3α-p-phenylbenzoyloxy-5α-hydroxy- 2β(3β-hydroxy-4,4-dimethyl-trans-1-octen-1-yl)cyclopent-1α-yl]acetic acid, γ-lactone as a viscous, colorless oil.

The latter product may be converted into the 2-[5α-hydroxy-3α-(tetrahydropyran-2-yloxy)-2β-(3β-(tetrahydropyran-2-yloxy)-4,4-dimethyl-trans-1-octen-1-yl)cyclopent-1α-yl]acetaldehyde, γ-hemiacetal by the procedures of Examples XLVII to XLIX.

The ir spectrum (CHCl$_3$) of the less polar product exhibited a strong absorption at 1775 cm$^{-1}$ for the lactone carbonyl, a strong absorption at 1715 cm$^{-1}$ for the ester carbonyl, a medium absorption at 1610 cm$^{-1}$ for the phenyl groups, and a medium absorption at 970 cm$^{-1}$ for the trans double bond. The nmr (CDCl$_3$) of the product exhibited a multiplet at 8.20–7.22 δ for the aromatic protons, a multiplet at 5.76–5.52 δ for the vinyl protons, a multiplet at 5.43–4.88 δ for the CHOCO, a doublet at 3.80 δ (J = 5 cps) for the CHOH, two singlets at 0.80 and 0.86 δ for the gem dimethyl groups, and multiplets at 3.00–0.57 δ for the remaining protons. The ir and nmr spectra of the more polar product were superimposable on those above.

EXAMPLE XLVII

A heterogeneous mixture of 2.87 g. (6.03 mmoles) of the product of Example XLVI and 0.830 g. (7.72 mmoles) of anhydrous potassium carbonate in 29 ml. of absolute methanol and 20 ml. of tetrahydrofuran was stirred under nitrogen for 1.5 hours. The reaction was then cooled in ice and quenched by the addition of 12.0 ml. (12.0 mmoles) of 1.0 N hydrochloric acid; the quenched reaction was further diluted with 49 ml. of water with the concomitant formation of a white precipitate. The precipitate (methyl p-phenylbenzoate) was collected by filtration and the filtrate was extracted with ethyl acetate (3 × 50 ml.). The combined organic extracts were washed with saturated brine, were dried (anhydrous magnesium sulfate), and were concentrated to afford the desired 2-[3α,5α-dihydroxy-2β-(3α-hydroxy-4,4-dimethyl-trans-1-octen-1-yl)cyclopent-1α-yl]acetic acid, γ-lactone as a colorless oil weighing 1.72 g. (97.0% yield) which was used without purification.

The ir spectrum (CHCl$_3$) of the crude product exhibited a strong absorption at 1775 cm$^{-1}$ for the lactone carbonyl and a medium absorption at 970 cm$^{-1}$ for the trans double bond. The nmr spectrum (CDCl$_3$) of the product exhibited a multiplet at 5.72–5.43 δ for the vinyl protons, a multiplet at 5.11–4.72 δ for the CHOCO, a multiplet at 4.23 δ for the CHOH, a broad singlet at 3.24–2.86 δ for the OH, two singlets at 0.80 and 0.88 δ for the gem dimethyl groups, and multiplets at 2.84–0.60 δ for the remaining protons.

EXAMPLE XLVIII

A solution of 1.72 g. (5.85 mmoles) of the product of Example XLVII, 1.7 ml. of distilled dihydropyran, and 17 mg. of p-toluenesulfonic acid monohydrate in 17 ml. of dry methylene chloride was stirred under nitrogen at room temperature for 2.0 hours then was diluted with ether. The organic solution was washed with saturated sodium bicarbonate, was dried (anhydrous magnesium sulfate), and was concentrated to afford a colorless oil. Purification of the colorless oil by silica gel chromatography (Baker "Analyzed" 60-200 mesh) using mixtures of benzene:ethyl acetate as eluents afforded, after removal of less polar impurities the desired 2-[5α-hydroxy-3α-(tetrahydropyran-2-yloxy)-2β-(3α-(tetrahydropyran-2-yloxy)-4,4-dimethyl-trans-1-octen-1-yl]cyclopent-1α-yl]acetic acid, γ-lactone as a colorless oil weighing 1.49 g. (55.2% yield).

The ir spectrum (CHCl$_3$) of the chromatographed product exhibited a strong absorption at 1770 cm$^{-1}$ for the lactone carbonyl and a medium absorption at 975 cm$^{-1}$ for the trans double bond. The nmr spectrum of the chromatographed product exhibited a multiplet at 5.73–5.42 δ for the vinyl protons, a multiplet at 5.26–4.88 δ for the CHOCO, a multiplet at 4.88–4.52 δ for the OCHO, multiplets at 4.37–3.31 δ for the CHO and CH$_2$O 2 singlets at 0.94 and 0.98 δ for the gem dimethyl groups, and multiplets at 2.97–0.70 δ for the remaining protons.

EXAMPLE XLIX

To a solution, cooled to −78° under nitrogen, of 1.49 g. (3.22 mmoles) of the chromatographed product of Example XLVIII in 17 ml. of dry toluene was added 3.99 ml. (3.22 mmoles) of a 20% solution of diisobutylaluminum hydride in hexane. The reaction mixture was stirred at −78° for 1 hour then was quenched by the addition of methanol until gas evolution ceased. The reaction mixture was then let warm to room temperature, was concentrated by rotary evaporation. The resultant gel was stirred with 150 ml. of methanol and the insoluble aluminum salts were removed by filtration. The filtrate was concentrated to an oil which was purified by silica gel chromatography (Baker "Analyzed" 60–200 mesh) using mixtures of benzene:ethyl acetate as eluents. After removal of less polar impurities the desired 2-[5α-hydroxy-3α-(tetrahydropyran-2-yloxy)-2β-(3α-(tetrahydropyran-2-yloxy)-4,4-dimethyl-trans-1-octen-1-yl]cyclopent-1α-yl]acetaldehyde, γ-hemiacetal was collected as a viscous, colorless oil weighing 1.06 g. (71.0% yield).

The ir spectrum (CHCl$_3$) exhibited a medium absorption at 975 cm$^{-1}$ for the trans double bond and no carbonyl absorption.

EXAMPLE L

To a solution of 835 mg. (1.61 mmoles) of the product of Example XXX in 2.0 ml. of dry dimethyl sulfoxide was added dropwise 1.42 ml. (2.72 mmoles) of a 1.91 M solution of sodium methylsulfinylmethide in dimethyl sulfoxide. To this red ylide solution was added dropwise a solution of 250 mg. (0.54 mmole) of the hemiacetal product of Example XLIX in 1.0 ml. of dry dimethyl sulfoxide over a period of 5 minutes. After being stirred for 20 hours at room temperature the reaction was poured onto ice water. The aqueous solution was covered with ethyl acetate and the vigorously stirred mixture was acidified to pH 3 by the addition of 10% aqueous hydrochloric acid. The acidified aqueous layer was further extracted with ethyl acetate (2x). The combined organic extracts were dried (anhydrous magnesium sulfate) and were concentrated to afford a crude oil. This oil was purified by column chromatography on silica gel (Baker "Analyzed" Reagent 60–200 mesh) using mixtures of chloroform:ethyl acetate as eluents. After removal of less polar impurities, the desired N-methanesulfonyl-9α-hydroxy-11α,15α-bis-(tetrahydropyran-2-yloxy)-16,16-dimethyl-cis-5-trans-13-prostadienamide were collected as a colorless oil weighing 249 mg. (75.5% yield).

The nmr spectrum (CDCl$_3$) of the chromatographed product exhibited a multiplet at 5.70–5.13 δ for the vinyl protons, a multiplet at 4.80–4.46 δ for the OCHO, a singlet at 3.24 δ for the SO$_2$CH$_3$, multiplets at 4.26–3.05 δ for the CH$_2$O and CHO, a singlet at 0.80 δ for the gem dimethyl groups and multiplets at 2.71–0.50 δ for the remaining protons.

The above product may be hydrolyzed as described in Example III to afford the N-methanesulfonyl 16,16-dimethylprostaglandin F$_2$ $_\alpha$ carboxamide which may be catalytically reduced as described in Example VII to provide the N-methanesulfonyl 16,16-dimethyl-13,14-dihydroprostaglandin F$_1$ $_\alpha$ carboxamide.

The above starting material may be subjected to catalytic reduction to produce N-methanesulfonyl-9α-hydroxy-11α,15α-bis(tetrahydropyran-2-yloxy)-trans-16,16-dimethyl-13-prostenamide which may be converted by known reactions (E. J. Corey, et al., *J. Am. Chem. Soc.*, 92, 2586 (1970)) to N-methanesulfonyl 16,16-dimethyl prostaglandin F$_1$ $_\alpha$ carboxamide or N-methanesulfonyl 16,16-dimethyl prostaglandin E$_1$ carboxamide. The latter may be converted by known reactions (Example VI) to N-methanesulfonyl 16,16-dimethyl prostaglandin A$_1$ carboxamide or (Example XXXVI) to N-methanesulfonyl 16,16-dimethyl prostaglandin F$_1$ $_\beta$ carboxamide.

The above product may be subjected to catalytic reduction to produce the N-methanesulfonyl 16,16-dimethyl-9α-hydroxy-11α,15α-bis-(tetrahydropyran-2-yloxy)16,16-dimethyl prostanamide called Compound A. Compound A may be hydrolyzed as described in Example III to produce the N-methanesulfonyl 16,16-dimethyl-13,14-dihydroprostaglandin F$_1$ carboxamide. Compound A may be subjected to oxidation as described in Example IV followed by hydrolysis as described in Example V to produce the N-methanesulfonyl 16,16-dimethyl-13,14-dihydroprostaglandin E$_1$ carboxamide called Compound B. Compound B may be dehydrated as described in Example VI to produce the N-methanesulfonyl 16,16-dimethyl-13,14-dihydroprostaglandin A$_1$ carboxamide or reduced as described in Example XXXVI to produce the N-methanesulfonyl 16,16-dimethyl-13,14-dihydroprostaglandin F$_1$ $_\beta$ carboxamide.

EXAMPLE LI

To a solution cooled to −20° under nitrogen of 249 mg. (0.403 mmole) of the N-methanesulfonyl-9α-hydroxy-11α,15α-bis(tetrahydropyran-2-yloxy)-16,16-dimethyl-cis-5-trans-13-prostadienamide prepared in Example L above in 5 ml. of reagent grade acetone was added dropwise 0.202 ml. of Jones' reagent. After 15 minutes the reaction was quenched by the addition of 0.202 ml. of isopropanol. The mixture was stirred in the cold for 5 minutes then was diluted with ethyl acetate. The organic layer was washed with water (2x) and saturated brine (1x), was dried (anhydrous magnesium sulfate), and was concentrated to afford the desired N-methanesulfonyl-9-oxo-11α,15α-bis-(tetrahydropyran-2-yloxy)-16,16-dimethyl-cis-5-trans-13-prostadienamide as an oil weighing 220 mg. (88.4% yield) which was used without purification.

EXAMPLE LII

A solution of 220 mg. (0.36 mmole) of the N-methanesulfonyl-9-oxo-11α,15α-bis-(tetrahydropyran-2-yloxy)-16,16-dimethyl-cis-5-trans-13-prostadienamide of Example LI in 5 ml. of a 65:35 mixture of acetic acid:water was stirred under nitrogen at room temperature overnight then was concentrated by rotary evaporation. The resultant crude oil was purified by column chromatography on silica gel (Mallinckrodt CC-7) using mixtures of chloroform:ethyl acetate as eluents. After elution of less polar impurities the N-methanesulfonyl-9-oxo-11α,15α-dihydroxy-16,16-dimethyl-cis-5-trans-13-prostadienamide was collected as a viscous, colorless oil weighing 73 mg. (44.5% yield).

The ir spectrum (CHCl$_3$) of the chromatographed product exhibited strong absorptions at 1735 and 1720 cm$^{-1}$ for the carbonyl groups and at 970 cm$^{-1}$ for the trans double bond. The nmr spectrum (CDCL$_3$) of the product exhibited a multiplet at 5.78–5.50 δ for the trans double bond, a multiplet at 5.50–5.20 δ for the cis double bond, multiplets at 4.29–3.70 δ for the C$\underline{H}$O, a singlet at 3.27 δ for the SO$_2$C$\underline{H}$$_3$, a singlet at 0.86 δ for the gem dimethyl groups, and multiplets at 2.80–0.56 δ for the remaining protons.

The above product may be dehydrated as described in Example VI to produce the N-methanesulfonyl 16,16-dimethyl prostaglandin A$_2$ carboxamide or reduced as described in Example XXXVI to produce the N-methanesulfonyl 16,16-dimethylprostaglandin F$_2$ $_\beta$ carboxamide.

The above product may also be catalytically reduced as described in Example VII to provide the N-methanesulfonyl 13,14-dihydroprostaglandin E$_1$ carboxamide. The latter may be dehydrated as described in Example VI to provide the N-methanesulfonyl 16,16-dimethyl-13,14-dihydroprostaglandin A$_1$ carboxamide or reduced as described in Example XXXVI to provide the N-methanesulfonyl 16,16-dimethyl-13,14-dihydroprostaglandin F$_1$ $_\beta$ carboxamide.

EXAMPLE LIII

To a solution of 2.60 g. (5.36 mmoles) of the product of Example I in 20 ml. of dry dimethyl sulfoxide was added dropwise 5.45 ml. (10.22 mmoles) of a 1.88 M solution of sodium methylsulfinylmethide in dimethyl sulfoxide. To this red ylide solution was added dropwise a solution of 250 mg. (0.54 mmole) of the hemiacetal product of Example XLIX in 1.0 ml. of dry dimethyl sulfoxide over a period of 5 minutes. After being stirred for 20 hours at room temperature the reaction was poured onto ice water. The aqueous solution is covered with ethyl acetate and the vigorously stirred mixture was acidified to pH 3 by the addition of 10% aqueous hydrochloric acid. The acidified aqueous layer was further extracted with ethyl acetate (2x). The combined organic extracts were dried (anhydrous magnesium sulfate) and were concentrated to afford a crude product. This crude product is purified by column chromatography on silica gel (Baker 'Analyzed' Reagent 60-200 mesh) using mixtures of benzene:chloroform as eluents. After elution of less polar impurities the desired N-acetyl 9α-hydroxy-11α,15α-bis-(tetrahydropyran-2-yloxy)-16,16-dimethyl-cis-5-trans-13-prostadienamide was collected as a viscous colorless oil weighing 250 mg. (78.5% yield).

The nmr spectrum (CDCl$_3$) of the chromatographed product exhibited a singlet at 9.3 δ for the NH, a multiplet at 5.65–5.22 δ for the olefinic protons, a broad singlet at 4.65 δ for the OC$\underline{H}$O, multiplets at 4.20–3.20 δ for the CHO and CH$_2$O, a singlet at 2.32 δ for the COC$\underline{H}$$_3$, a singlet at 0.80 δ for the gem dimethyl groups, and multiplets at 2.69–0.61 δ for the remaining protons.

The above product may be hydrolyzed as described in Example III to provide the N-acetyl 16,16-dimethyl prostaglandin $F_2\alpha$ carboxamide which may be catalytically reduced to provide the N-acetyl 16,16-dimethyl-13,14-dihydroprostaglandin $F_1\alpha$ carboxamide.

The above starting material may be subjected to catalytic reduction to produce N-acetyl-9α-hydroxy-11α,15α-bis-(tetrahydropyran-2-yloxy)-16,16-dimethyl-trans-13-prostenamide which may be converted by known reactions (E. J. Corey, et al., *J. Am. Chem. Soc.*, 92, 2586 (1970) to N-acetyl 16,16-dimethyl prostaglandin $F_1\alpha$ carboxamide or N-acetyl 16,16-dimethyl prostaglandin $E_1$ carboxamide. The latter may be converted by known reactions (Example VI) to N-acetyl 16,16-dimethyl prostaglandin $A_1$ carboxamide or (Example XXXVI) to N-acetyl 16,16-dimethyl prostaglandin $F_1\alpha$ carboxamide.

The above product may be subjected to catalytic reduction to produce the N-acetyl-9α-hydroxy-11α,15α-bis-(tetrahydropyran-2-yloxy)-16,16-dimethyl prostanamide called Compound A. Compound A may be hydrolyzed as described in Example III to produce the N-acetyl-16,16-dimethyl-13,14-dihydroprostaglandin $F_1\alpha$ carboxamide. Compound A may be subjected to oxidation as described in Example IV followed by hydrolysis as described in Example V to produce the N-acetyl-16,16-dimethyl-13,14-dihydroprostaglandin $E_1$ carboxamide called Compound B. Compound B may be dehydrated as described in Example VI to produce the N-acetyl-16,16-dimethyl-13,14-dihydroprostaglandin $A_1$ carboxamide or reduced as described in Example XXXVI to produce the N-acetyl 16,16-dimethyl-13,14-dihydroprostaglandin $F_1\beta$ carboxamide.

EXAMPLE LIV

To a solution cooled to −20° under nitrogen of 250 mg. (0.424 mmole) of the N-acetyl-9α-hydroxy-11α,15α-bis-(tetrahydropyran-2-yloxy)-16,16-dimethyl-cis-5-trans-13-prostadienamide prepared in Example LIII above in 7 ml. of reagent grade acetone was added dropwise 0.212 ml. of Jones' reagent. After 15 minutes the reaction was quenched by the addition of 0.212 ml. of isopropanol. The mixture was stirred in the cold for 10 minutes then is diluted with ethyl acetate. The organic layer was washed with water (2x) and saturated brine (1x), was dried (anhydrous magnesium sulfate), and was concentrated to afford the desired N-acetyl-9-oxo-11α,15α-bis-(tetrahydropyran-2-yloxy)-16,16-dimethyl-cis-5-trans-13-prostadienamide as a viscous, colorless oil weighing 226 mg. (90.4% yield). The crude product was used with purification.

EXAMPLE LV

A solution of 226 mg. of the N-acetyl-9-oxo-11α,15α-bis-(tetrahydropyran-2-yloxy)-16,16-dimethyl-cis-5-trans-13-prostadienamide of Example LIV in 5.0 ml. of a 65:35 mixture of acetic acid:water was stirred under nitrogen at room temperature overnight then was concentrated by rotary evaporation. The resultant crude oil was purified by column chromatography on silica gel (Mallinckrodt CC-7) using mixtures of chloroform:ethyl acetate as eluents. After elution of less polar impurities the desired N-acetyl-9-oxo-11α,15α-dihydroxy-16,16-dimethyl-cis-5-trans-13-prostadienamide was collected as a viscous, colorless oil weighing 57 mg.

The ir spectrum (CHCl$_3$) of the product exhibited strong absorptions at 1745 and 1710 cm$^{-1}$ for the carbonyl groups and a medium adsorption at 975 cm$^{-1}$ for the trans double bond. The nmr spectrum (CDCl$_3$) exhibited a multiplet at 5.75–5.48 δ for the trans double bond, a multiplet at 5.48–5.20 δ for the cis double bond, a multiplet at 4.16–3.68 δ for the CHO, a singlet at 2.26 δ for the COC$\underline{H}_3$, a singlet at 0.88 δ for the gem dimethyl groups, and multiplets at 2.62–0.60 δ for the remaining protons.

The above product may be dehydrated as described in Example VI to the N-acetyl 16,16-dimethylprostaglandin $A_2$ carboxamide or reduced as described in Example XXXVI to the N-acetyl 16,16-dimethylprostaglandin $F_2\beta$ carboxamide.

The above product may be catalytically reduced as described in Example VII to the N-acetyl 16,16-dimethyl-13,14-dihydroprostaglandin $E_1$ carboxamide. The latter may be converted (Example VI) to the N-acetyl 16,16-dimethyl-13,14-dihydroprostaglandin $A_1$ carboxamide or (Example XXXVI) to the N-acetyl 16,16-dimethyl-13,14-dihydroprostaglandin $F_1\beta$ carboxamide.

EXAMPLE LVI

To a solution of 2.42 g. (5.00 mmoles) of the product of Example I in 5.0 ml. of dry dimethyl sulfoxide is added dropwise 10.5 ml. (10.0 mmoles) of a 0.95 M solution of sodium methylsulfinylmethide in dimethyl sulfoxide. To this red ylide solution is added dropwise a solution of 450 mg. (1.00 mmole) of the hemiacetal products of Example XL in 2.0 ml. of dry dimethyl sulfoxide over a period of 0.5 hour. After being stirred for 20 hours at room temperature the reaction is poured onto ice water. The aqueous solution is covered with ethyl acetate and the vigorously stirred mixture is acidified to pH 3 by the addition of 10% aqueous hydrochloric acid. The acidified aqueous layer is further extracted with ethyl acetate (2x). The combined organic extracts are dried (anhydrous magnesium sulfate) and are concentrated to afford a crude product. This crude product is purified by column chromatography to afford the desired N-acetyl-9α-hydroxy-11α,15α-bis-(tetrahydropyran-2-yloxy)-15β-methyl-cis-5-trans-13-prostadienamide and N-acetyl-9α-hydroxy-11α,15β-bis-(tetrahydropyran-2-yloxy)-15α-methyl-cis-5-trans-13-prostadienamide.

The above product may be hydrolyzed as described in Example III to the N-acetyl 15-methylprostaglandin $F_2\alpha$ carboxamide which may be catalytically reduced as described in Example VII to the N-acetyl 15-methyl-13,14-dihydroprostaglandin $F_1\alpha$ carboxamide.

The above starting material may be subjected to catalytic reduction to produce N-acetyl-9α-hydroxy-11α,15-bis-(tetrahydropyran-2-yloxy)-15-methyl-trans-13-prostenamide which may be converted by known reactions (E. J. Corey, et al., *J. Am. Chem. Soc.*, 92, 2586 (1970) to N-acetyl-15-methylprostaglandin $F_1\alpha$ carboxamide or N-acetyl-15-methylprostaglandin $E_1$ carboxamide. The latter may be converted by known reactions (Example VI) to N-acetyl-15-methylprostaglandin $A_1$ carboxamide or (Example XXXVI) to N-acetyl 15-methylprostaglandin $F_1\beta$ carboxamide.

The above product may be subjected to catalytic reduction to produce the N-acetyl-9α-hydroxy-11α,15-bis-(tetrahydropyran-2-yloxy)-15-methyl-prostanamide called Compound A. Compound A may be hydrolyzed as described in Example III to produce the N-acetyl-15-methyl-13,14-dihydroprostaglandin $F_1\alpha$ carboxamide. Compound A may be subjected to oxidation as described in Example IV followed by hydrolysis as described in Example V to produce the N-acetyl-15-methyl-13,14-dihydroprostaglandin $E_1$ carboxamide called Compound B. Compound B may be dehydrated as described in Example VI to produce the N-acetyl-15-methyl-13,14-dihydroprostaglandin $A_1$ carboxamide or reduced as described in Example XXXVI to produce the N-acetyl 15-methyl-13,14-dihydroprostaglandin $F_1$ $\beta$ carboxamide.

EXAMPLE LVII

To a solution cooled to −20° under nitrogen of 139 mg. (0.24 mmole) of the epimeric products prepared in Example LVI above in 4 ml. of reagent grade acetone is added dropwise 0.080 ml. (0.213 mmoles) of Jones' reagent. After 15 minutes the reaction is quenched by the addition of 0.080 ml. of isopropanol. The mixture is stirred in the cold for 10 minutes then is diluted with ethyl acetate. The organic layer is washed with water, (2×) and saturated brine (1×), is dried (anhydrous magnesium sulfate), and is concentrated to afford the crude epimeric mixture of N-acetyl-9-oxo-11α,15α-bis-(tetrahydropyran-2-yloxy)-15β-methyl-cis-5-trans-13-prostadienamide and N-acetyl-9-oxo-11α,15β-bis-(tetrahydropyran-2-yloxy)-15α-methyl-cis-5-trans-13-prostadienamide which is used without further purification.

EXAMPLE LVIII

A solution of 65 mg. (0.11 mmole) of the epimeric mixture of Example LVIII in 2.0 ml. of a 65:35 mixture of acetic acid:water is stirred under nitrogen at room temperature overnight then is concentrated by rotary evaporation. The resultant crude oil is purified by column, thin layer, or liquid-liquid chromatography to provide N-acetyl-9-oxo-11α,15α-dihydroxy-15β-methyl-cis-5-trans-13-prostadienamide and the N-acetyl-9-oxo-11α,15β-dihydroxy-15α-methyl-cis-5-trans-13prostadienamide.

The above product may be dehydrated as described in Example VI to produce the N-acetyl 15-methylprostaglandin $A_2$ carboxamide or reduced as described in Example XXXVI to produce the N-acetyl-15-methyl-prostaglandin $F_2$ $\beta$ carboxamide.

The above product may be catalytically reduced as described in Example VII to provide the N-acetyl 15-methyl 13,14-dihydroprostaglandin $E_1$ carboxamide. The latter may be converted (Example VI) to the N-acetyl 15-methyl-13,14-dihydroprostaglandin $A_1$ carboxamide or (Example XXXVI) to the N-acetyl ·15methyl-13,14-dihydroprostaglandin $F_1$ $\beta$ carboxamide.

EXAMPLE LIX

A solution of 3.14 g. (20.0 mmoles) of benzenesulfonamide and 4.38 g. (22.0 mmoles) of 5-bromovaleric acid chloride in 10 ml. of acetonitrile was heated at reflux under nitrogen for 1.5 hours. The reaction was then concentrated to afford a crude brown solid which was recrystallized from methylene chloride:hexane (after treatment with Darco). The desired N-benzenesulfonyl-5-bromovaleramide was collected as colorless needles weighing 5.39 g. (84.5% yield) melting at 95°–97°.

The ir spectrum ($CHCl_3$) exhibited a strong absorption at 1720 $cm^{-1}$ attributable to the carbonyl group.

The nmr spectrum ($CDCl_3$) exhibited a broad singlet at 9.05δ for the N<u>H</u>, two multiplets at 8.07–7.82δ and 7.61–7.23δ for the aromatic protons, a multiplet at 3.40–3.08δ for the C<u>H</u>$_2$Br, a multiplet at 2.43–2.07δ for the C<u>H</u>$_2$CO, and a multiplet at 1.85–1.48δ for the C<u>H</u>$_2$—C<u>H</u>$_2$.

A solution of 4.81 g. (15.0 mmoles) of the N-benzenesulfonyl-5-bromovaleramide prepared above and 5.89 g. (22.5 mmoles) of triphenylphosphine in 50 ml. of acetonitrile was heated at reflux for 140 hours then was concentrated to afford a white foam. The white foam was triturated with ether (3×) then was recrystallized from methylene chloride benzene. The desired [4-benzenesulfonylaminocarbonylbutyl]triphenylphosphonium bromide was collected as colorless needles weighing 5.33 g. (61.2% yield) melting at 176°–179°.

The ir spectrum exhibited a strong absorption at 1720 $cm^{-1}$ attributable to the carbonyl group. The nmr spectrum ($CDCl_3$) of the product exhibited a multiplet at 8.15–7.27 γ for the aromatic protons, a broad multiplet at 3.85–3.14δ for the C<u>H</u>$_2$P, a multiplet at 2.87–2.47 δ for the C<u>H</u>$_2$CO, and a multiplet at 2.04–1.38 δ for the C<u>H</u>$_2$C<u>H</u>$_2$.

The above product may be caused to react with the known 2-[5α-hydroxy-3α-(tetrahydropyran-2-yloxy)-2β-(3α-(tetrahydropyran-2-yloxy)-trans-1-cis5-octadien-1-yl)cyclopent-1α-yl]acetaldehyde, ε-hemiacetal (E. J. Corey, et al., *J. Am. Chem. Soc.*, 93, 1490 (1971) to produce N-benzenesulfonyl-9α-hydroxy-11α,15α-bis-(tetrahydropyran-2-yloxy)-cis-5-trans-13-cis-17-prostatrienamide which may be converted by known reactions (E. J. Corey, ibid) into the N-benzenesulfonylprostaglandin $F_3$ $_\alpha$ carboxamide or the N-benzenesulfonylprostaglandin $E_3$ carboxamide.

The above product may be caused to react with the mixed 2-[5α-hydroxy-3α-(tetrahydropyran-2-yloxy)-2β-(3β-methyl-3α-(tetrahydropyran-2-yloxy)-trans-1-octen-1-yl)cyclopent-1α-yl]acetaldehyde, γ-hemiacetal and 2-[5α-hydroxy-3α-(tetrahydropyran-2-yloxy)-2β-(3α-methyl-3β-(tetrahydropyran-2-yloxy)-trans-1-octen-1-yl)cyclopent-1α-yl]acetaldehyde, γ-hemiacetal prepared in Example XL to produce N-benzenesulfonyl-9α-hydroxy-11α,15-bis-(tetrahydropyran-2-yloxy)-15-methyl-cis-5-trans-13-prostadienamide called Compound A. Compound A may be hydrolyzed as described in Example III to produce the N-benzenesulfonyl-15-methylprostaglandin $F_2$ $_\alpha$ carboxamide (which may be subjected to catalytic hydrogenation as described in Example VII to produce N-benzenesulfonyl 15-methyl-13,14-dihydroprostaglandin $F_1$ $_\alpha$ carboxamide). Compound A may be subjected to oxidation as described in Example IV followed by hydrolysis as described in Example V to produce N-benzenesulfonyl 15-methyl prostaglandin $E_2$ carboxamide called Compound B. Compound B may be dehydrated as described in Example VI to produce N-benzenesulfonyl 15-methylprostaglandin $A_2$ carboxamide or reduced as described in Example XXXVI to produce N-benzenesulfonyl 15-methyl prostaglandin $F_2$ $\beta$ carboxamide. Compound B may also be catalytically hydrogenated as described in Example VII to produce N-benzenesulfonyl 15-methyl-13,14-dihydroprostaglandin $E_1$ carboxamide which may be dehydrated as described in Example VI to produce N-benzenesulfonyl 15-methyl-13,14-dihydroprostaglandin $A_1$, carboxamide or reduced as described in Example XXXVI to produce N-benzenesulfonyl 15-methyl-13,14-dihydroprostaglandin $F_1\beta$ carboxamide.

Compound A may be subjected to carefully controlled catalytic reduction to produce N-benzenesulfonyl-9α-hydroxy-11α,15-bis-(tetrahydropyran-2-yloxy)-15-methyl-trans-13-prostenamide which may be converted by known reactions (E. J. Corey, et al., *J. Am. Chem. Soc.* 92,2586 (1970) to N-benzenesulfonyl 15-methyl prostaglandin $F_1\alpha$ carboxamide. The latter may be converted as described in Example VI to N-benzenesulfonyl 15-methylprostaglandin $A_1$ carboxamide or as described in Example VI to N-benzenesulfonyl 15-methylprostaglandin $F_1$ carboxamide. The above product may be caused to react with the 2-[5α-hydroxy-3α-(tetrahydropyran-2-yloxy)-2β-(3α-(tetrahydropyran-2-yloxy)oct-1-yl)cyclopent-1α-yl]acetaldehyde, γ-hemiacetal prepared in Example XXVII to produce N-benzenesulfonyl-9α-hydroxy-11α,15α-bis-(tetrahydropyran-2-yloxy)-cis-5-prostenamide called Compound C. Compound C may be hydrolyzed as described in Example III to produce the N-benzenesulfonyl 13,14-dihydroprostaglandin $F_2$ carboxamide. Compound C may be subjected to oxidation as described in Example IV followed by hydrolysis as described in Example V to produce the N-benzenesulfonyl 13,14-dihydroprostaglandin $E_2$ carboxamide. The latter may be dehydrated as described in Example VI to produce the N-benzenesulfonyl 13,14-dihydroprostaglandin $A_2$ carboxamide or reduced as described in Example XXVI to produce the N-benzenesulfonyl 13,14-dihydroprostaglandin $F_2$ carboxamide.

The above product may be caused to react with the mixed 2-[5α-hydroxy-3α-(tetrahydropyran-2-yloxy)2β-(3β-methyl-3α-(tetrahydropyran-2-yloxy)oct-1-yl)cyclopent-1α-yl]acetaldehyde, γ-hemiacetal and 2-[5α-hydroxy-3α-(tetrahydropyran-2-yloxy)-2β-(3α-methyl-3α-(tetrahydropyran-2-yloxy)oct-1-yl)cyclopent-1α-yl]-acetaldehyde, γ-hemiacetal prepared in Example XXIX to produce N-benzenesulfonyl-9α-hydroxy-15-methyl-11α,15-bis(tetrahydropyran-2-yloxy)-cis-5-prostenamide called Compound D. Compound D may be hydrolyzed as described in Example III to produce the N-benzenesulfonyl 15-methyl-13,14-dihydroprostaglandin $F_2\ \alpha$ carboxamide. Compound D may be subjected to oxidation as described in Example IV followed by hydrolysis as described in Example V to produce the N-benzenesulfonyl 15-methyl-13,14-dihydroprostaglandin $E_2$ carboxamide. The latter may be dehydrated as described in Example VI to produce the N-benzenesulfonyl 15-methyl-13,14-dihydroprostaglandin $A_2$ carboxamide or reduced as described in Example XXXVI to produce the N-benzenesulfonyl 15-methyl-13,14-dihydroprostaglandin $F_2\ \beta$ carboxamide.

The above product may be caused to react with the 2-[5α-hydroxy-3α-(tetrahydropyran-2-yloxy)-2β-(3β-(tetrahydropyran-2-yloxy)oct-1-yl)cyclopent-1α-yl]acetaldehyde, τ-hemiacetal prepared in Example XXIII to produce N-benzenesulfonyl-9α-hydroxy-11α,15β-bis-(tetrahydropyran-2-yloxy)-cis-5-prostenamide called Compound E. Compound E may be hydrolyzed as described in Example III to produce the N-benzenesulfonyl 15-epi-13,14-dihydroprostaglandin $F_2$ carboxamide. Compound E may be subjected to oxidation as described in Example IV followed by hydrolysis as described in Example V to produce the N-benzenesulfonyl 15-epi-13,14-dihydroprostaglandin $E_2$ carboxamide. The latter may be dehydrated as described in Example VI to produce the N-benzenesulfonyl 15-epi-13,14-dihydroprostaglandin $A_2$ carboxamide or reduced as described in Example XXXVI to produce the N-benzenesulfonyl 15-epi-13,14-dihydroprostaglandin $F_2\ \beta$ carboxamide.

The above product may be caused to react with the 2-[5α-hydroxy-3α-(tetrahydropyran-2-yloxy)-2β-(3β-(tetrahydropyran-2-yloxy)-1-trans-octen-1-yl)cyclopent-1α-yl]acetaldehyde, γ-hemiacetal prepared in Example XXIV to produce N-benzenesulfonyl-9α-hydroxy-11α,15β-bis(tetrahydropyran-2-yloxy)-trans-13-cis-5-prostadienamide called Compound F. Compound F may be hydrolyzed as described in Example III to produce the N-benzenesulfonyl 15-epi prostaglandin $F_2\ \alpha$ carboxamide. Compound F may be subjected to oxidation as described in Example IV followed by hydrolysis as described in Example V to produce the N-benzenesulfonyl 15-epi-prostaglandin $E_2$ carboxamide. The latter may be dehydrated as described in Example VI to produce the N-benzenesulfonyl 15-epi-prostaglandin $A_2$ carboxamide or reduced as described in Example XXXVI to produce the N-benzenesulfonyl 15-epi-prostaglandin $F_2\ \beta$ carboxamide.

The above product may be caused to react with the 2-[3α,5α-dihydroxy-2β-(3α-hydroxy-trans-1-octen-1-yl)cyclopent-1α-yl]-acetaldehyde, γ-hemiacetal prepared in Example XXV to produce the N-benzenesulfonyl prostaglandin $F_2\ \alpha$ carboxamide.

The above product may be caused to react with the 2-[3α,5α-dihydroxy-2β-(3α-hydroxyoct-1-yl)cyclopent-1α-yl]acetaldehyde, γ-hemiacetal prepared in Example XXVI to produce the N-benzenesulfonyl 13,14-dihydroprostaglandin $F_2\ \alpha$ carboxamide.

The above product may be caused to react with the 2-[3α,5α-dihydroxy-2β-(3β-hydroxy-trans-1-octen-1-yl)cyclopent-1α-yl]acetaldehyde, γ-hemiacetal prepared in Example XXI to provide the N-benzenesulfonyl 15-epi-prostaglandin $F_2\ \alpha$ carboxamide.

The above product may be caused to react with the 2-[3α,5α-dihydroxy-2β-(3β-hydroxy-oct-1-yl)cyclopent-1α-yl]acetaldehyde, γ-hemiacetal prepared in Example XXI to provide the N-benzenesulfonyl 15-epi-13,14-dihydroprostaglandin $F_2\ \alpha$.

The above product may be caused to react with the 2-[3α,5α-dihydroxy-2β-(3α-hydroxy-3β-methyl-trans-1-octen-1-yl)cyclopent-1α-yl]acetaldehyde, γ-hemiacetal prepared in Example XXXVII to provide the N-benzenesulfonyl 15-methylprostaglandin $F_2\ \alpha$ carboxamide.

The above product may be caused to react with the 2-[3α,5α-dihydroxy-2β-(3α-hydroxy-3β-methyl-oct-1-yl)cyclopent-1α-yl]-acetaldehyde. γ-hemiacetal prepared in Example XXXVII to provide the N-benzenesulfonyl 15-methyl-13,14-dihydroprostaglandin $F_2\ \alpha$.

EXAMPLE LX

To a solution of the phosphonium bromide of Example LIX (2.53 g.; 4.36 mmoles) in 3.0 ml. of dry dimethyl sulfoxide was added dropwise 5.05 ml. (8.72 mmoles) of a 1.73 M solution of sodium methylsulfinylmethide in dry dimethyl sulfoxide. The resultant red ylide solution was stirred under nitrogen for 5 minutes then a solution of 0.476 g. (1.09 mmole) of the known 2-[5α-hydroxy-3α-(tetrahydropyran-2-yloxy)-2β-[3α-(tetrahydropyran-2-yloxy)-trans-1-octen-1-yl]cyclopent-1α-yl]acetaldehyde, γ-hemiacetal in 2.0 ml. of dry dimethyl sulfoxide was added dropwise. The solution was stirred for 2.75 hours then was poured onto a mixture of ethyl acetate:ice-water. The vigorously stirred solution was acidified to pH ~ 3 with 10% aqueous hydrochloric acid. The acidified aqueous layer was extracted with ethyl acetate and the combined organic extracts were dried (anhydrous magnesium sulfate) and concentrated to afford a crude yellow oil. The oil was purified by column chromatography on silica gel using mixtures of chloroform:ethyl acetate as eluents. Aftr removal of less polar impurities the desired -N-benzenesulfonyl-9α-hydroxy-11α,15α-bis-(tetrahydropyran-2-yloxy)-cis-5-trans-13-prostadienamide was collected as a colorless oil weighing 294 mg. (40.8% yield).

The nmr spectrum ($CDCl_3$) of the chromatographed product exhibited multiplets at 8.19–7.92 δ and 7.72–7.37 δ for the aromatic protons, a multiplet at 5.70–5.12 δ for the vinyl protons, a multiplet at 4.83–4.60 δ for the OCHO, multiplets at 4.29–3.30 δ for the $CH_2O$ and CHO, and multiplets at 2.49–0.70 δ for the remaining protons.

The above product may be subjected to catalytic reduction to produce N-benzenesulfonyl-9α-hydroxy-11α,15α-bis-(tetrahydropyran-2-yloxy)-trans-13-prostenamide which may be converted by known reactions (E. J. Corey, et al., *J. Am. Chem. Soc.*, 92, 2586 (1970)) to N-benzenesulfonyl prostaglandin $F_1$ α carboxamide or N-benzenesulfonyl prostaglandin $E_1$ carboxamide. The latter may be converted by known reactions (Example VI) to N-benzenesulfonyl prostaglandin $A_1$ carboxamide or (Example XXXVI) to N-benzenesulfonyl prostaglandin $F_1$ β carboxamide.

The above product may be subjected to catalytic reduction to produce the N-benzenesulfonyl-9α-hydroxy-11α,15α-bis-(tetrahydropyran-2-yloxy)prostanamide called Compound A. Compound A may be hydrolyzed as described in Example III to produce the N-benzenesulfonyl-13,14-dihydroprostaglandin $F_1$ carboxamide. Compound A may be subjected to oxidation as described in Example IV followed by hydrolysis as described in Example V to produce the N-benzenesulfonyl-13,14-dihydroprostaglandin $E_1$ carboxamide called Compound B. Compound B may be dehydrated as described in Example VI to produce the N-benzenesulfonyl-13,14-dihydroprostaglandin $A_1$ carboxamide or reduced as described in Example XXXVI to produce the N-benzenesulfonyl-13,14-dihydroprostaglandin $F_1$ β carboxamide.

EXAMPLE LXI

A solution of 104 mg. of the bis-THP ether of Example LX and 5.0 ml. of a 65:35 mixture of acetic acid:water was heated to 40° ± 2° for 2.5 hours under nitrogen. The solution was then concentrated and the resultant oil was purified by column chromatography on silica gel (SilicAR CC-4). After removal of higher $R_f$ impurities with chloroform, elution with 10% methanol in methylene chloride provided the desired N-benzenesulfonyl-9α,11α,15α-trihydroxy-cis-5-trans-13-prostadienamide as a white foam weighing 30 mg. (38.0% yield).

The nmr spectrum ($CDCl_3$) of the chromatographed product exhibited multiplets at 8.10–7.88 δ and 7.60–7.36 δ for the aromatic protons, multiplets at 5.60–5.37 δ and 5.37–5.08 δ for the vinyl protons, multiplets at 4.24–3.73δ for the CHO, and multiplets at 2.52–0.69 δ for the remaining protons. The ir spectrum ($CHCl_3$) of the product exhibited strong absorptions at 1720 cm$^{-1}$ for the carbonyl group and 965 cm$^{-1}$ for the trans double bond.

The above product may be catalytically reduced as described in Example VII to produce the N-benzenesulfonyl 13,14-dihydroprostaglandin $F_1$ α carboxamide.

EXAMPLE LXII

To a solution of 187 mg. (0.283 mmole) of the alcohol of Example LX in 3 ml. of acetone cooled to −15° under nitrogen was added 0.10 ml. of Jones' reagent. The mixture was stirred in the cold for 15 minutes then was quenched in the cold by the addition of 0.10 ml. of isopropanol. The mixture was diluted with ethyl acetate; the diluted solution was washed with water (2×) and with saturated brine (1×), was dried (anhydrous magnesium sulfate), and was concentrated to afford the oily, colorless N-benzenesulfonyl-9-oxo-11α,15α-bis-(tetrahydropyran-2-yloxy)-cis-5-trans-13-prostadienamide weighing 175 mg. (93.5% yield) which was used without purification.

EXAMPLE LXIII

A solution of 175 mg. (0.266 mmoles) of the bis-THP ether of Example LXII in 3 ml. of a 65:35 mixture of acetic acid:water was heated to 40 ± 2° under nitrogen for 6 hours. The mixture was then concentrated and the resultant oily product was purified by column chromatography on silica gel (Mallinckrodt CC-4). After removal of higher $R_f$ impurities with a chloroform elution with a 1:1 mixture of chloroform:ethyl acetate afforded the desired N-benzenesulfonyl-9-oxo-11α,15α-dihydroxy-cis-5-trans-13-prostadienamide as a foam weighing 35 mg. (26.8% yield).

The ir spectrum ($CHCl_3$) of the chromatographed product exhibited strong absorptions at 1735 and 1720 cm$^{-1}$ for the carbonyl groups and a medium absorption at 970 cm$^{-1}$ for the trans double bond. The nmr spectrum ($CDCl_3$) of the product exhibited multiplets at 8.10–7.88 δ and 7.67–7.40 δ for the aromatic protons, a multiplet at 5.72–5.50 δ for the trans double bond and 5.39–5.10 δ for the cis double bond, a multiplet at 4.27–3.88 δ for the CHO, and multiplets at 2.68–0.68 δ for the remaining protons.

The above product may be dehydrated as described in Example VI to provide the N-benzenesulfonyl prostaglandin $A_2$ carboxamide or reduced as described in Example XXXVI to provide the N-benzenesulfonyl prostaglandin $F_2$ β carboxamide.

The above product may also be catalytically hydrogenated as described in Example VII to produce the N-benzenesulfonyl 13,14-dihydroprostaglandin $E_1$ carboxamide. The latter may be converted (Example VI) to N-benzenesulfonyl 13,14-dihydroprostaglandin $A_1$ carboxamide or (Example XXXVI) to N-benzenesulfonyl 13,14-dihydroprostaglandin $F_1$ β carboxamide.

EXAMPLE LXIV

A mixture of 2.57 g. (15 mmoles) of p-toluenesulfonamide and 2.99 g. (15 mmoles) of 5-bromovaleric acid chloride was heated on a steam bath for 20 minutes. The resultant solid N-p-toluenesulfonyl-5-bromovaleramide was let cool and was recrystallized twice from methylene chloride:hexane as white needles weighing 4.63 g. (92.0% yield) melting at 116°–117°.

The nmr spectrum ($CDCl_3$) of the crystalline product exhibited a singlet at 9.68 δ for the N—H, two doublets at 7.95 and 7.35 δ (J=8 cps) for the aromatic protons, a multiplet at 3.50–3.18 δ for the —$CH_2$Br, a multiplet at 2.53–2.18 δ for the $CH_2$CO, a singlet at 2.45 δ for the —$CH_3$, and a multiplet at 1.94–1.54 δ for the —$CH_2CH_2$—. The ir spectrum ($CHCl_3$) showed a strong absorption at 1720 $cm^{-1}$ attributable to the carbonyl group.

A solution of 3.34 g. (10 mmoles) of the bromosulfonamide prepared above and 3.93 g. (15 mmoles) of triphenylphosphine in 50 ml. of acetonitrile was heated at reflux overnight. The solution was then concentrated and the resultant solid was triturated (3×) with benzene then was recrystallized from ethanol:ether to afford the white crystalline [4-(p-toluenesulfonylaminocarbonyl)butyl]triphenylphosphonium bromide weighing 3.87 g. (64% yield) melting at 134°–141°.

The nmr spectrum ($CDCl_3$) of the crystalline product exhibited a broad singlet at 11.8 δ for the NH, multiplets at 8.10–7.13 δ for the aromatic protons, a multiplet at 3.96–3.29 δ for the —$CH_2P$, a multiplet at 2.92–2.56 δ for the —$CH_2CO$, a singlet at 2.38 δ for the —$CH_3$, and a multiplet at 2.16–1.40 δ for the —$CH_2C$-$H_2$—. The ir spectrum ($CHCl_3$) showed a strong absorption at 5.82 μ attributable to the carbonyl group.

The above product may be caused to react with the known 2-[5α-hydroxy-3α-(tetrahydropyran-2-yloxy)-2β-(3α-(tetrahydropyran-2-yloxy)-trans-1-cis-5-octadien-1-yl)cyclopent-1α-yl]acetaldehyde, γ-hemiacetal (E. J. Corey, et al., J. Am. Chem. Soc., 93, 1490 (1971) to produce N-p-toluenesulfonyl-9α-hydroxy-11α,15α-bis-(tetrahydropyran-2-yloxy)-cis-5-trans-13-cis-17-prostatrienamide which may be converted by known reactions (E. J. Corey, ibid) into the N-p-toluenesulfonyl prostaglandin $F_3$ $_\alpha$ carboxamide or the N-p-toluenesulfonyl prostaglandin $E_3$ carboxamide.

The above product may be caused to react with the mixed 2-[5α-hydroxy-3α-(tetrahydropyran-2-yloxy)-2β-(3β-methyl-3α-(tetrahydropyran-2-yloxy)-trans-1-octen-1-yl)cyclopent-1α-yl]acetaldehyde, γ-hemiacetal and 2-[5α-hydroxy-3α-(tetrahydropyran-2-yloxy)-2β-(3α-methyl-3β-(tetrahydropyran-2-yloxy)-trans-1-octen-1-yl)cyclopent-1α-yl]acetaldehyde, γ-hemiacetal prepared in Example XL to produce N-p-toluenesulfonyl-9α-hydroxy-11α,15-bis-(tetrahydropyran-2-yloxy)15-methyl-cis-5-trans-13-prostadienamide called Compound A. Compound A may be hydrolyzed as described in Example III to produce the N-p-toluenesulfonyl-15-methyl prostaglandin $F_2$ $_\alpha$ carboxamide (which may be subjected to catalytic hydrogenation as described in Example VII to produce N-p-toluenesulfonyl 15-methyl-13,14-dihydroprostaglandin $F_1$ $_\alpha$ carboxamide. Compound A may be subjected to oxidation as described in Example IV followed by hydrolysis as described in Example V to produce N-p-toluenesulfonyl 15-methyl prostaglandin $E_2$ carboxamide called Compound B. Compound B may be dehydrated as described in Example VI to produce N-p-toluenesulfonyl 15-methylprostaglandin $A_2$ carboxamide or reduced as described in Example XXXVI to produce the N-p-toluenesulfonyl 15-methylprostaglandin $F_2$ $_\beta$ carboxamide. Compound B may also be catalytically hydrogenated as described in Example VII to produce N-p-toluenesulfonyl 15-methyl-13,14-dihydroprostaglandin $E_1$ carboxamide which may be dehydrated as described in Example VI to produce N-p-toluenesulfonyl 15-methyl-13,14-dihydroprostaglandin $A_1$ carboxamide or reduced as described in Example XXXVI to produce N-p-toluenesulfonyl 15-methyl-13,14-dihydroprostaglandin $F_1$ $_\beta$ carboxamide.

Compound A may be subjected to carefully controlled catalytic reduction to produce N-p-toluenesulfonyl-9α-hydroxy-11α,15-bis-(tetrahydropyran-2-yloxy)-15-methyl-trans-13-prostenamide which may be converted by known reactions (E. J. Corey, et al., J. Am. Chem. Soc., 92, 2586 (1970) to N-p-toluenesulfonyl 15-methyl prostaglandin $F_1$ $_\alpha$ carboxamide and N-p-toluenesulfonyl 15-methylprostaglandin $E_1$ carboxamide. The latter may be converted as described in Example VI to N-p-toluenesulfonyl 15-methylprostaglandin $A_1$ carboxamide or as described in Example XXXVII to N-p-toluenesulfonyl 15-methylprostaglandin $F_1$ $_\beta$ carboxamide.

The above product may be caused to react with 2-[3α,5α-dihydroxy-2β-(3α-hydroxy-trans-1-octen-1-yl)cyclopent-1α-yl]acetaldehyde, γ-hemiacetal prepared in Example XXV to afford the N-p-toluenesulfonyl prostaglandin $F_2$ $_\alpha$ carboxamide.

The above product may be caused to react with 2-[3α,5α-dihydroxy-2β-(3α-hydroxyoct-1-yl)cyclopent-1α-yl]acetaldehyde, γ-hemiacetal prepared in Example XXVI to afford the N-p-toluenesulfonyl 13,14-dihydroprostaglandin $F_2$ $_\alpha$ carboxamide.

The above product may be caused to react with the 2-[5α-hydroxy-3α-(tetrahydropyran-2-yloxy)2β-(3α-(tetrahydropyran-2-yloxy)oct-1-yl)cyclopent-1α-yl]acetaldehyde, γ-hemiacetal (prepared in Example XXVII) to produce N-p-toluenesulfonyl-9α-hydroxy-11α,15α-bis-(tetrahydropyran-2-yloxy)-cis-5-prostenamide called Compound C. Compound C may be hydrolyzed as described in Example III to produce the N-p-toluenesulfonyl 13,14-dihydroprostaglandin $F_2$ $_\alpha$ carboxamide. Compound C may be subjected to oxidation as described in Example IV followed by hydrolysis as described in Example V to produce the N-p-toluenesulfonyl 13,14-dihydroprostaglandin $E_2$ carboxamide. The latter may be dehydrated as described in Example VI to produce the N-p-toluenesulfonyl 13,14-dihydroprostaglandin $A_2$ carboxamide or reduced as described in Example XXXVI to produce the N-p-toluenesulfonyl 13,14-dihydroprostaglandin $F_2$ $_\beta$ carboxamide.

The above product may be caused to react with the mixed 2-[5α-hydroxy-3α-(tetrahydropyran-2-yloxy)2β-(3β-methyl-3α-(tetrahydropyran-2-yloxy)oct-1-yl)cyclopent-1α-yl]acetaldehyde, γ-hemiacetal and 2-[5α-hydroxy-3α-(tetrahydropyran-2-yloxy)-2β-(3α-methyl-3β-(tetrahydropyran-2-yloxy)oct-1-yl)cyclopent-1α-yl]acetaldehyde, γ-hemiacetal prepared in Example XXIX to produce N-p-toluenesulfonyl-9α-hydroxy-15-methyl-11α,15-bis-(tetrahydropyran-2-yloxy)-cis-5-prostenamide called Compound D. Compound D may be hydrolyzed as described in Example III to produce the N-p-toluenesulfonyl 15-methyl-13,14-dihydroprostaglandin $F_2$ $_\alpha$ carboxamide. Compound D may be subjected to oxidation as described in Example IV followed by hydrolysis as described in Example V to produce the N-p-toluenesulfonyl 15-methyl-13,14-dihydroprostaglandin $E_2$ carboxamide. The latter may be dehydrated as described in Example VI to produce the N-p-toluenesulfonyl 15-methyl-13,14-dihydroprostaglandin $A_2$ carboxamide or reduced as described in Example XXXVI to produce the N-p-toluenesulfonyl 15-methyl-13,14-dihydroprostaglandin $F_2$ $_\beta$ carboxamide.

The above product may be caused to react with the 2[5α-hydroxy-3α-(tetrahydropyran-2-yloxy)-2β-(3β-(tetrahydropyran-2-yloxy)oct-1-yl)cyclopent-1α-yl]acetaldehyde γ-hemiacetal (prepared in Example XXIX to produce N-p-toluenesulfonyl-9α-hydroxy-11α,15β-bis-(tetrahydropyran-2-yloxy)-cis-5-prostenamide called Compound E. Compound E may be hydrolyzed as described in Example III to produce the N-p-toluenesulfonyl 15-epi-13,14-dihydroprostaglandin $F_2$ $\alpha$ carboxamide. Compound E may be subjected to oxidation as described in Example IV followed by hydrolysis as described in Example V to produce the N-p-toluenesulfonyl 15-epi-13,14-dihydroprostaglandin $E_2$ carboxamide. The latter may be dehydrated as described in Example VI to produce the N-p-toluenesulfonyl 15-epi-13,14-dihydroprostaglandin $A_2$ carboxamide or reduced as described in Example XXXVI to produce the N-p-toluenesulfonyl 15-epi-13,14-dihydroprostaglandin $F_2$ $\beta$ carboxamide.

The above product may be caused to react with the 2-[5α-hydroxy-3α-(tetrahydropyran-2-yloxy)2β-(3β-(tetrahydropyran-2-yloxy)-trans-1-octen-1-yl)cyclopent-1α-yl]acetaldehyde, γ-hemiacetal prepared in Example XXIV to produce N-p-toluenesulfonyl 9α-hydroxy-11α,15β-bis-(tetrahydropyran-2-yloxy)-cis-5-prostenamide called Compound F. Compound F may be hydrolyzed as described in Example III to produce the N-p-toluenesulfonyl 15-epi-prostaglandin $F_2$ $\alpha$ carboxamide. Compound F may be subjected to oxidation as described in Example IV followed by hydrolysis as described in Example V to produce the N-p-toluenesulfonyl 15-epi-prostaglandin $E_2$ carboxamide. The later may be dehydrated as described in Example VI to produce the N-p-toluenesulfonyl 15-epi-prostaglandin $A_2$ carboxamide or reduced as described in Example XXXVI to produce the N-p-toluenesulfonyl 15-epi-prostaglandin $F_2$ $\beta$ carboxamide.

EXAMPLE LXV

To a solution of the phosphonium bromide of Example LXIV (2.68 g., 4.50 mmoles which was dried overnight at 144°) in 2.0 ml. of dry dimethyl sulfoxide was added dropwise 4.65 ml. (9.00 mmoles) of a 1.94 M solution of sodium methylsulfinylmethide in dry dimethyl sulfoxide. The resultant red ylide solution was stirred under nitrogen for 15 minutes then a solution of 653 mg. (1.50 mmoles) of the known 2-[5α-hydroxy-3α-(tetrahydropyran-2-yloxy)-2β-[3α-(tetrahydropyran-2-yloxy)-trans-1-octen-1-yl]cyclopent-1α-yl]acetaldehyde, γ-hemiacetal in 20 ml. of dry dimethyl sulfoxide was added. The mixture was stirred under nitrogen for 5 hours then was poured onto a mixture of ice water:ether. The aqueous layer was acidified with 10% aqueous hydrochloric acid then was extracted with ether (3×). The combined ethereal extracts were dried (anhydrous magnesium sulfate) and were concentrated to afford a crude yellow oil which was purified by silica gel column chromatography. After removal of less polar materials with mixtures of chloroform:benzene, elution with ethyl acetate afforded the colorless, oily N-p-toluenesulfonyl-9α-hydroxy-11α,1-5α-bis(tetrahydropyran-2-yloxy)-cis-5-trans-13-prostadienamide weighing 383 mg. (37.9% yield).

The nmr spectrum ($CDCl_3$) of the oily product exhibited two doublets at 7.89 and 7.23 δ (J=8 cps) for the aromatic protons, a multiplet at 5.64–5.00 δ for the olefinic protons, a broad singlet at 4.63 δ for the O—CH—O, multiplets at 4.28-3.20 δ for the —CHO— and —$CH_2$O, a singlet at 2.42δ for the —$CH_3$, and multiplets at 2.68-0.48δ for the remaining protons. The ir spectrum ($CHCl_3$) showed strong absorptions at 1710 cm$^{-1}$ attributable to the carbonyl absorption and 970 cm$^{-1}$ attributable to the trans double bond.

The above product may be caused to react with the 2-[3α,5α-dihydroxy-2β-(3β-hydroxy-trans-1-octen-1-yl)cyclopent1α-yl]acetaldehyde, γ-hemiacetal prepared in Example XXI to provide the N-p-toluenesulfonyl 15-epi-prostaglandin $F_2$ $\alpha$ carboxamide.

The above product may be caused to react with the 2-[3α,5α-dihydroxy-2β-(3β-hydroxyoct-1-yl)cyclopent-1α-yl]acetaldehyde, γ-hemiacetal prepared in Example XXI to provide the N-p-toluenesulfonyl 15-epi-13,14-dihydroprostaglandin $F_2$ $\alpha$.

The above product may be caused to react with the 2-[3α,5α-dihydroxy-2β-(3α-hydroxy-3β-methyl-trans-1-octen-1-yl)cyclopent-1α-yl]acetaldehyde, γ-hemiacetal prepared in Example XXXVII to provide the N-p-toluenesulfonyl 15-methylprostaglandin $F_2$ $\alpha$ carboxamide.

The above product may be caused to react with the 2[3α,5α-dihydroxy-2β-(3α-hydroxy-3β-methyl-oct-1-yl)cyclopent-1α-yl]acetaldehyde, γ-hemiacetal prepared in Example XXXVII to provide the N-p-toluenesulfonyl 15-methyl-13,14-dihydroprostaglandin $F_2$ $\alpha$.

The above starting material may be subjected to carefully controlled catalytic reduction to produce N-p-toluenesulfonyl-9α-hydroxy-11α,15α-bis-(tetrahydropyran-2-yloxy)-trans-13-prostenamide which may be converted by known reactions (E. J. Corey, et al., J. Am. Chem. Soc., 92, 2586 (1970) to N-p-toluenesulfonyl prostaglandin $F_1$ $\alpha$ carboxamide or N-p-toluenesulfonyl prostaglandin $E_1$ carboxamide. The latter may be converted by known reactions (Example VI) to N-p-toluenesulfonyl prostaglandin $A_1$ carboxamide or (Example XXXVI) to N-p-toluenesulfonyl prostaglandin $F_1$ $\beta$ carboxamide.

The above product may be subjected to catalytic reduction to produce the N-p-toluenesulfonyl-9α-hydroxy-11α,15α-bis-(tetrahydropyran-2-yloxy)prostanamide called Compound A. Compound A may be hydrolyzed as described in Example III to produce the N-p-toluenesulfonyl-13,14-dihydroprostaglandin $F_1$ $\alpha$ carboxamide. Compound A may be subjected to oxidation as described in Example IV followed by hydrolysis as described in Example V to produce the N-p-toluenesulfonyl-13,14-dihydroprostaglandin $E_1$ carboxamide called Compound B. Compound B may be dehydrated as described in Example VI to produce the N-p-toluenesulfonyl-13,14-dihydroprostaglandin $A_1$ carboxamide or reduced as described in Example XXXVI to produce the N-p-toluenesulfonyl-13,14-dihydroprostaglandin $F_1$ $\beta$ carboxamide.

EXAMPLE LXVI

A solution of 222 mg. (0.329 mmole) of the bis-THP ether of Example LXV in 2 ml. of a 65:35 mixture of acetic acid-water was heated to 40° ± 2° under nitrogen for 5 hours, then was concentrated. The oily product was purified by column chromatography on silica gel (SilicAR CC-4). After removal of less polar impurities with chloroform, elution with a 9:1 mixture of methylene chloride-methanol afforded the desired N-p-toluenesulfonyl-9α,11α,15α-trihydroxy-cis-5-trans-13-prostadienamide, as a colorless, viscous oil weighing 50 mg. (30% yield).

The nmr spectrum ($CDCl_3$) of the oily product exhibited two doublets at 7.85 and 7.23 δ (J = 7 cps) for the aromatic protons two overlapping multiplets at 5.68–4.94 δ for the olefinic protons, multiplets at 4.68–2.90 δ for the -C$\underline{H}$O- and O$\underline{H}$, a singlet at 2.32 δ for the —C$\underline{H}_3$, and multiplets at 2.50–0.43 δ for the remaining protons.

The above product may be catalytically reduced as described in Example VII to produce the N-p-toluenesulfonyl 13,14-dihydroprostaglandin $F_{1\alpha}$ carboxamide.

EXAMPLE LXVII

To a solution, cooled to −15°, of 0.161 g. (0.239 mmole) of the bis-THP ether of Example LXV in 4 ml. of acetone was added 0.101 ml. of Jones' reagent. The mixture was stirred under nitrogen in the cold for 20 minutes then was quenched by the addition of 0.10 ml. of isopropanol. The mixture was stirred for an additional 5 minutes then was diluted with ethyl acetate. The organic layer was washed with water (2×) and saturated brine (1×), was dried (anhydrous magnesium sulfate), and was concentrated to afford the crude, oily N-p-toluenesulfonyl-9-oxo-11α,15α-bis-(tetrahydropyran-2-yloxy)-cis-5-trans-13-prostadieneamide weighing 156 mg. (97.0%) which was used without purification.

EXAMPLE LXVIII

A solution of 156 mg. (0.232 mmole) of the crude bis-THP ether of Example LXVII in 3.0 ml. of a 65:35 mixture of acetic acid-water was heated under nitrogen at 40° ± 2° for 4 hours then was concentrated. The crude oily product was purified by silica gel column chromatography (Mallinckrodt CC-4). After removal of less polar material with chloroform, elution with 2% methanol in chloroform afforded the colorless, viscous, oily N-p-toluenesulfonyl-9-oxo-11α,15α-dihydroxy-5-cis-13-trans-prostadienamide, weighing 32 mg. (27.4% yield).

The nmr spectrum (CDCl$_3$) of the product exhibited two doublets at 7.81 and 7.20 δ (J=8 cps) for the olefinic protons, a multiplet at 5.64–5.31 δ for the trans olefin, a multiplet at 5.31–4.98 δ for the cis olefin, a multiplet at 4.23–3.55 δ for the —C$\underline{H}$O—, a singlet at 2.23 δ for the —C$\underline{H}_3$, and multiplets at 2.57–0.37 δ for the remaining protons. The ir spectrum (CDCl$_3$) showed strong absorptions at 1720 and 1730 cm$^{-1}$ attributable to the carbonyl groups and at 970 cm$^{-1}$ attributable to the trans double bond.

The above product may be dehydrated as described in Example VI to provide the N-p-toluenesulfonyl prostaglandin $A_2$ carboxamide or reduced as described in Example XXXVI to provide the N-p-toluenesulfonyl prostaglandin $F_{2\beta}$ carboxamide.

The above product may be catalytically reduced as described in Example VII to provide the N-p-toluenesulfonyl 13,14-dihydroprostaglandin $E_1$ carboxamide. The latter may be converted (Example VI) to N-p-toluenesulfonyl 13,14-dihydroprostaglandin $A_1$ carboxamide or (Example XXXVI) to N-p-toluenesulfonyl 13,14-dihydroprostaglandin $F_{1\beta}$ carboxamide.

EXAMPLE LXIX

A solution of 4.26 g. (20.0 mmoles) of 2-thiophenesulfonamide and 4.38 g. (22.0 mmoles) of 5-bromovaleric acid chloride in 10 ml. of acetonitrile was heated at reflux for 7.5 hours. The reaction was then concentrated and the resulting dark solid was dissolved in methylene chloride, was treated with Darco and filtered; hexane was added to the filtrate to initiate crystallization. After cooling the desired N-(2-thiophenesulfonyl)-5-bromovaleramide was collected as white needles weighing 5.92 g. (90.8% yield) and melting at 85°–88°.

The ir spectrum (CDCl$_3$) of the product exhibited a strong absorption at 1720 cm$^{-1}$ attributable to the carbonyl groups. The nmr spectrum (COCl$_3$) exhibited three complex multiplets at 7.96–7.75 δ, 7.75–7.53 δ, and 7.25–6.93 δ for the thiophene protons, a multiplet at 3.60–3.20 δ for the C$\underline{H}_2$Br, a multiplet at 2.59–2.20 δ for the C$\underline{H}_2$CO, and a multiplet at 1.97–1.53 δ for the C$\underline{H}_2$C$\underline{H}_2$.

A solution of 4.88 g. (15.0 mmoles) of the N-(2-thiophenesulfonyl)-5-bromovaleramide prepared above and 5.89 g. (22.5 mmoles) of triphenylphosphine in 60 ml. of acetonitrile was heated at reflux for 6 days then was concentrated to afford a white foam. The white foam was triturated with ether (3×) then was recrystallized from methanol:ether. The desired [4-(2-thiophenesulfonyl)aminocarbonylbutyl]triphenylphosphonium bromide was collected as colorless cubes weighing 4.97 g. (56.3% yield) which melted at 215°–218°.

The ir spectrum (KBr) exhibited a strong absorption at 5.85 µ attributable to the carbonyl group. The nmr spectrum (CF$_3$CO$_2$H) exhibited multiplets at 8.13–7.13 δ for the phenyl and thiophene protons, a broad multiplet at 3.58–2.99 δ for the C$\underline{H}_2$P, a multiplet at 2.85–2.54 δ for the C$\underline{H}_2$CO, and a broad multiplet at 2.25–1.75 δ for the C$\underline{H}_2$C$\underline{H}_2$.

The above product may be caused to react with the known 2-[5α-hydroxy-3α-(tetrahydropyran-2-yloxy)-2β-(3α-(tetrahydropyran-2-yloxy)-trans-1-cis-5-octadien-1-yl)cyclopent-1α-yl]acetaldehyde, γ-hemiacetal (E. J. Corey, et al., *J. Am. Chem. Soc.*, 93, 1490 (1971) to produce N-(2-thiophenesulfonyl) 9α-hydroxy-11α,15α-bis-(tetrahydropyran-2-yloxy)-cis-5-trans-13-cis-17-prostatrienamide which may be converted by known reactions (E. J. Corey, ibid) into the N-(2-thiophenesulfonyl) prostaglandin $F_{3\alpha}$ carboxamide or the N-(2-thiophenesulfonyl) prostaglandin $E_3$ carboxamide.

The above product may be caused to react with the 2-[3α,5α-dihydroxy-2β-(3α-hydroxy-trans-1-octen-1-yl)cyclopent-1α-yl]acetaldehyde, γ-hemiacetal prepared in Example XXV to afford the N-(2-thiophenesulfonyl) prostaglandin $F_{2\beta}$ carboxamide.

The above product may be caused to react with the 2-[3α,5α-dihydroxy-2β-(3α-hydroxy oct-1-yl)cyclopent-1α-yl]acetaldehyde, γ-hemiacetal prepared in Example XXVI to afford the N-(2-thiophenesulfonyl) 13,14-dihydroprostaglandin $F_{2\alpha}$ carboxamide.

The above product may be caused to react with the mixed 2-[5α-hydroxy-3α-(tetrahydropyran-2-yloxy)-2β-(3β-methyl-3α-(tetrahydropyran-2-yloxy)-trans-1-octen-1-yl)cyclopent-1α-yl]acetaldehyde, γ-hemiacetal and 2-[5α-hydroxy-3α-(tetrahydropyran-2-yloxy)-2β-(3α-methyl-3β-(tetrahydropyran-2-yloxy)-trans-1-octen-1-yl)cyclopent-1α-yl]acetaldehyde, γ-hemiacetal prepared in Example XL to produce N-(2-thiophenesulfonyl)-9α-hydroxy-11α,15-bis-(tetrahydropyran-2-yloxy)-15-methyl-cis-5-trans-13-prostadienamide called Compound A. Compound A may be hydrolyzed as described in Example III to produce the N-(2-thiophenesulfonyl)-15-methyl prostaglandin $F_{2\alpha}$ carboxamide (which may be subjected to catalytic hydrogenation as described in Example VII to produce N-(2-thiophenesulfonyl)-15-methyl-13,14-dihydroprostaglandin $F_{1\alpha}$ carboxamide). Compound A may be subjected to oxidation as described in Example IV followed by hydrolysis as described in Example V to produce N-(2-thiophenesulfonyl) 15-methyl prostaglandin $E_2$ carboxamide called Compound B. Compound B may be dehydrated as described in Example VI to produce N-(2-thiophenesulfonyl) 15-methyl prostaglandin $A_2$ carboxamide or reduced as described in Example XXXVI to produce the N-(2-thiophenesulfonyl) 15-methyl prostaglandin $F_2$ $\beta$ carboxamide. Compound B may also be catalytically hydrogenated as described in Example VII to produce N-(2-thiophenesulfonyl) 15-methyl-13,14-dihydroprostaglandin $E_1$ carboxamide which may be dehydrated as described in Example VI to produce N-(2-thiophenesulfonyl) 15-methyl-13,14-dihydroprostaglandin $A_1$ carboxamide or reduced as described in Example XXXVI to produce N-(2-thiophenesulfonyl) 15-methyl-13,14-dihydroprostaglandin $F_1$ $\beta$ carboxamide.

Compound A may be subjected to carefully controlled catalytic reduction to produce N-(2-thiophenesulfonyl)-9α-hydroxy-11α,15α-bis-(tetrahydropyran-2-yloxy)-15β-methyl-trans-13-prostenamide which may be converted by known reactions (E. J. Corey, et al., J. Am. Chem. Soc., 92, 2586 (1970) to N-(2-thiophenesulfonyl) 15-methyl prostaglandin $F_1$ $\alpha$ carboxamide and N-(2-thiophenesulfonyl) 15-methyl prostaglandin $E_1$ carboxamide. The latter may be converted as described in Example VI to N-(2-thiophenesulfonyl) 15-methyl prostaglandin $A_1$ carboxamide or as described in Example XXXVI to N-(2-thiophenesulfonyl) 15-methyl prostaglandin $F_1$ $\beta$ carboxamide.

The above product may be caused to react with the known 2-[5α-hydroxy-3α-(tetrahydropyran-2-yloxy)-2β-(3α-(tetrahydropyran-2-yloxy)oct-1-yl)cyclopent-1α-yl]acetaldehyde, γ-hemiacetal prepared in Example XXVII to produce N-(2-thiophenesulfonyl)-9α-hydroxy-11α,15α-bis-(tetrahydropyran-2-yloxy)-cis-5-prostenamide called Compound C. Compound C may be hydrolyzed as described in Example III to produce the N-(2-thiophenesulfonyl) 13,14-dihydroprostaglandin $F_2$ $\alpha$ carboxamide. Compound C may be subjected to oxidation as described in Example IV followed by hydrolysis as described in Example V to produce the N-(2-thiophenesulfonyl) 13,14-dihydroprostaglandin $E_2$ carboxamide. The latter may be dehydrated as described in Example VI to produce the N-(2-thiophenesulfonyl) 13,14-dihydroprostaglandin $A_2$ carboxamide or reduced as described in Example XXXVI to produce the N-(2-thiophenesulfonyl) 13,14-dihydroprostaglandin $F_2$ $\beta$ carboxamide.

The above product may be caused to react with the mixed 2-[5α-hydroxy-3α-(tetrahydropyran-2-yloxy)-2β-(3β-methyl-3α-(tetrahydropyran-2-yloxy)oct-1-yl)cylcopent-1α-yl]acetaldehyde, γ-hemicatel and 2-[5α-hydroxy-3α-(tetrahydropyran-2-yloxy)-2β-(3α-methyl-3β-(tetrahydropyran-2-yloxy)oct-1-yl)cyclopent-1α-yl]acetaldehyde, γ-hemiacetal prepared in Example XXIX to produce N-(2-thiophenesulfonyl)-9α-hydroxy-15-methyl-11α,15-bis-(tetrahydropyran-2-yloxy)-cis-5-prostenamide called Compound D. Compound D may be hydrolyzed as described in Example III to produce the N-(2-thiophenesulfonyl) 15-methyl-13,14-dihydroprostaglandin $F_2$ $\alpha$ carboxamide. Compound D may be subjected to oxidation as described in Example IV followed by hydrolysis ad described in Example V to produce the N-(2-thiophenesulfonyl) 15-methyl-13,14-dihydroprostaglandin $E_2$ carboxamide. The latter may be dehydrated as described in Example VI to produce the N-(2-thiophenesulfonyl) 15-methyl-13,14-dihydroprostaglandin $A_2$ carboxamide or reduced as described in Example XXXVI to provide the N-(2-thiophenesulfonyl) 15-methyl-13,14-dihydroprostaglandin $F_2$ $\beta$ carboxamide.

The above product may be caused to react with the known 2-[5α-hydroxy-3α-(tetrahydropyran-2-yloxy)-2β-(3β-(tetrahydropyran-2-yloxy)oct-1-yl)cyclopent-1α-yl]acetaldehyde, γ-hemiacetal prepared in Example XXIII to produce N-(2-thiophenesulfonyl)-9α-hydroxy-11α,15β-bis-(tetrahydropyran-2-yloxy)-cis-5-prostenamide called Compound E. Compound E may be hydrolyzed as described in Example III to produce the N-(2-thiophenesulfonyl)15-epi-13,14-dihydroprostaglandin $F_2$ $\alpha$ carboxamide. Compound E may be subjected to oxidation as described in Example IV followed by hydrolysis as described in Example V to produce the N-(2-thiophenesulfonyl)15-epi-13,14-dihydroprostaglandin $E_2$ carboxamide. The latter may be dehydrated as described in Example VI to produce the N-(2-thiophenesulfonyl) 15-epi-13,14-dihydroprostaglandin $A_2$ carboxamide or reduced as described in Example XXXVI to produce the N-(2-thiophenesulfonyl) 15-epi-13,14-dihydroprostaglandin $F_2$ $\beta$ carboxamide.

The above product may be caused to react with the 2-[5α-hydroxy-3α-(tetrahydropyran-2-yloxy)-2β-(3β-(tetrahydropyran-2-yloxy)-trans-1-octen-1-yl)cyclopent-1α-yl]acetaldehyde, γ-hemiacetal to produce N-(2-thiophenesulfonyl)-9α-hydroxy-11α,15β-bis(tetrahydropyran-2-yloxy)-trans-13-cis-5-prostadienamide called Compound F. Compound F may be hydrolyzed as described in Example III to produce the N-(2-thiophenesulfonyl)15-epi-prostaglandin $F_2$ $\alpha$ carboxamide. Compound F may be subjected to oxidation as described in Example IV followed by hydrolysis as described in Example V to produce the N-(2-thiophenesulfonyl)15-epi-prostaglandin $E_2$ carboxamide. The latter may be dehydrated as described in Example VI to produce the N-(2-thiophenesulfonyl)15-epi-prostaglandin $A_2$ carboxamide or reduced as described in Example XXXVI to produce the N-(2-thiophenesulfonyl)15-epi-prostaglandin $F_2$ $\beta$ carboxamide.

The above product may be caused to react with the 2-[3α,5α-dihydroxy-2β-(3β-hydroxy-trans-1-octen-1-yl)cyclopent-1α-yl]acetaldehyde, γ-hemiacetal prepared in Example XXI to provide the N-(2-thiophenesulfonyl)-15-epi-prostaglandin $F_2$ $\alpha$ carboxamide.

The above product may be caused to react with the 2-[3α,5α-dihydroxy-2β-(3β-hydroxyoct-1-yl)cyclopent-1α-yl]acetaldehyde, γ-hemiacetal prepared in Example XXI to provide the N-(2-thiophenesulfonyl)15-epi-13,14-dihydroprostaglandin $F_2$ $\alpha$ .

The above product may be caused to react with the 2-[3α,5α-dihydroxy-2β-(3α-hydroxy-3β-methyl-trans-1-octen-1-yl)cyclopent-1α-yl]acetaldehyde, γ-hemiacetal prepared in Example XXXVII to provide the N-(2-thiophenesulfonyl)15-methylprostaglandin $F_2$ $\alpha$ carboxamide.

The above product may be caused to react with the 2-[3α,5α-dihydroxy-2β-(3α-hydroxy-3β-methyl-oct-1-yl)cyclopent-1α-yl]acetaldehyde, γ-hemiacetal prepared in Example XXXVII to provide the N-(2-thiophenesulfonyl)15-methyl-13,14-dihydroprostaglandin $F_2$ $\alpha$ .

EXAMPLE LXX

To a solution of the phosphonium bromide of Example LXIX (2.34 g; 4.0 mmoles) in 2.0 ml. of dry dimethyl sulfoxide was added dropwise 3.59 ml. (7.5 mmoles) of a 2.09 M solution of sodium methylsulfinylmethide in dry dimethyl sulfoxide. The resultant red ylide solution was stirred under nitrogen for 5 minutes then a solution of 0.438 g. (1.0 mmole) of the known 2-[5α-hydroxy-3α-(tetrahydropyran-2-yloxy)-2β-[3α-(tetrahydropyran-2-yloxy)-trans-1-octen-1-yl]cyclopent-1α-yl]acetaldehyde, γ-hemiacetal in 2.0 ml. of dry dimethyl sulfoxide was added dropwise over a period of 10 minutes. The solution was stirred overnight then was poured onto a mixture of ethyl acetate-ice water. The vigorously stirred solution was acidified to pH∼3 with 10% aqueous hydrochloric acid. The acidified aqueous layer was extracted with ethyl acetate and the combined organic extracts were dried (anhydrous magnesium sulfate) and concentrated to afford a crude yellow oil. The oil was purified by column chromatography on silica gel. After removal of less polar materials with 2% diethylamine in ethyl acetate elution with ethyl acetate afforded the colorless, oily N-(2-thiophenesulfonyl)-9α-hydroxy-11α,15α-bis-(tetrahydropyran-2-yloxy)-cis-5-trans-13-prostadienamide weighing 113 mg.

The nmr spectrum ($CDCl_3$) of the chromatographed product exhibited multiplets at 7.86–7.48δ and 7.23–6.90δ for the thiophene protons, a multiplet at 5.60–5.06β for the vinyl protons, a multiplet at 4.72–4.43δ for the OCHO, multiplets at 4.20–3.14δ for the $CH_2O$ and CHO, and multiplets at 2.63–0.52δ for the remaining protons.

The above starting material may be subjected to carefully controlled catalytic reduction to produce N-(2-thiophenesulfonyl)-9α-hydroxy-11α,15α-bis-(tetrahydropyran-2-yloxy)-trans-13-prostenamide which may be converted by known reactions (E. J. Corey, et al., *J. Am. Chem. Soc.*, 92, 2586 (1970) to N-(2-thiophenesulfonyl) prostaglandin $F_1$ α carboxamide or (Example XXXVI) to N-(2-thiophenesulfonyl)prostaglandin $F_1$ β carboxamide.

The above product may be subjected to catalytic reduction to produce the N-(2-thiophenesulfonyl)-9α-hydroxy-11α,15α-bis-(tetrahydropyran-2-yloxy)prostanamide called Compound A. Compound A may be hydrolyzed as described in Example III to produce the N-(2-thiophenesulfonyl)-13,14-dihydroprostaglandin $F_1$ α carboxamide. Compound A may be subjected to oxidation as described in Example IV followed by hydrolysis as described in Example V to produce the N-(2-thiophenesulfonyl)-13,14-dihydroprostaglandin $E_1$ carboxamide called Compound B. Compound B may be dehydrated as described in Example VI to produce the N-(2-thiophenesulfonyl)-13,14-dihydroprostaglandin $A_1$ carboxamide or reduced as described in Example XXXVI to produce the N-(2-thiophenesulfonyl)-13,14-dihydroprostaglandin $F_1$ β carboxamide.

EXAMPLE LXXI

A solution of 121 mg. (0.178 mmole) of the bis-THP ether of Example LXX and 2.0 ml. of a 65:35 mixture of acetic acid:water was heated to 40° ± 2° for 5 hours under nitrogen. The solution was then concentrated and the resultant oil was purified by column chromatography on silica gel (Mallinckrodt CC-4). After removal of higher $R_f$ impurities with chloroform, elution with 3% methanol in methylene chloride afforded the N-(2-thiophene)sulfonyl-9α,11α,15α-trihydroxy-cis-5-trans-13-prostadienamide as a foam weighing 61 mg.

The nmr spectrum ($CDCl_3$) of the product exhibited multiplets at 7.84–7.48δ and 7.10–6.90δ for the thiophene protons, overlapping multiplets at 5.60–5.10δ for the vinyl protons, a multiplet at 4.28–3.75δ for the CHO, and multiplets at 2.57–0.60δ for the remaining protons.

The above product may be catalytically reduced as described in Example VII to provide the N-(2-thiophenesulfonyl) 13,14-dihydroprostaglandin $F_1$ α carboxamide.

EXAMPLE LXXII

To a solution of 180 mg. (0.265 mmoles) of the alcohol of Example LXX in 3 ml. of acetone cooled to −15° under nitrogen was added 0.20 ml. of Jones' reagent. The mixture was stirred in the cold for 20 minutes then was quenched in the cold by the addition of 0.20 ml. of isopropanol. The mixture was diluted with ethyl acetate; the diluted solution was washed with water (2x) and with saturated brine (1x), was dried (anhydrous magnesium sulfate), and was concentrated to afford the oily, colorless N-(2-thiophenesulfonyl)-9-oxo-11α,15α-bis-(tetrahydropyran-2-yloxy)-cis-5-trans-13-prostadienamide weighing 159 mg. (88.3% yield) which was used without purification.

EXAMPLE LXXIII

A solution of 159 mg. of the bis-THP ether of Example LXXVII in 3 ml. of a 65:35 mixture of acetic acid:-water was heated to 40° ± 2° under nitrogen for 4.5 hours. The mixture was then concentrated and the resultant oily product was purified by column chromatography on silica gel (Mallinckrodt CC-4). After removal of higher $R_f$ impurities with chloroform elution with 2% methanol in methylene chloride afforded the desired N-(2-thiophenesulfonyl)-9-oxo-11α,15α-dihydroxy-5-cis-13-trans-prostadienamide as a viscous oil weighing 72 mg.

The nmr spectrum ($CDCl_3$) of the product exhibited multiplets at 7.90–7.55δ and 7.16–6.94δ for the thiophene protons, a multiplet at 5.72–5.43δ for the trans double bond, a multiplet at 5.43–5.10δ for the cis double bond, a broad singlet at 5.60–4.75δ for the OH and NH, a multiplet at 4.32–3.81δ for the CHO, and multiplets at 2.75–0.63δ for the remaining protons.

The above product may be dehydrated as described in Example VI to produce the N-(2-thiophenesulfonyl) prostaglandin $A_2$ carboxamide or reduced as described in Example XXXVI to produce the N-(2-thiophenesulfonyl) prostaglandin $F_2$ carboxamide.

The above product may be catalytically reduced as described in Example VII to the N-(2-thiophenesulfonyl) 13,14-dihydroprostaglandin $E_1$ carboxamide. The latter may be converted (Example VI) to N-(2-thiophenesulfonyl) 13,14-dihydroprostaglandin $A_1$ carboxamide or (Example XXXVI) to N-(2-thiophenesulfonyl) 13,14-dihydroprostaglandin $F_1$ carboxamide.

EXAMPLE LXXIV

To a solution, cooled to −78° under nitrogen, of 14.8 g. (0.043 mole) of the known 2-[2β-benzyloxymethyl-3α-(tetrahydropyran-2-yloxy)-5α-hydroxylcyclopent-1α-yl]acetic acid, γ-lactone (see: JACS, 93, 1490 (1971) in 160 ml. of dry toluene was added dropwise 41.0 ml. (0.057 mole) of a 20% solution of diisobutylaluminum hydride in hexane. The solution was stirred for 25 minutes then was quenched by the addition of 4 ml. of methanol. The quenched mixture was let to warm to room temperature was diluted with ether, was washed with 50% sodium potassium tartrate and with brine, was dried (anhydrous magnesium sulfate), and was concentrated to an oil. Purification of the oil by silica gel chromatography (Baker "Analyzed" 60–200 mesh). After removal of less polar impurities with 15% hexane in benzene, elution with ethyl acetate afforded the desired 2-[2β-benzyloxymethyl-3α-(tetrahydropyran-2-yloxy)-5α-hydroxycyclopent-1α-yl]acetaldehyde, γ-hemiacetal as a colorless oil weighing 14.9 g. (99.6% yield).

The nmr spectrum ($CDCl_3$) of the chromatographed product exhibited a singlet at 7.31δ for the phenyl protons, a multiplet at 5.75–5.32δ for the CHOCO, a singlet at 4.50δ for the $CH_2$-ph, a multiplet at 4.98–4.45δ for the OCHO, and multiplets at 4.40–1.20δ for the remaining protons.

EXAMPLE LXXV

To a solution of 7.80 g. (15.0 mmoles) of the product of Example XXX in 14 ml. of dimethyl sulfoxide is added dropwise 15.0 ml. of a 2.0 M solution of sodium methylsulfinylmethide in dimethyl sulfoxide. To the resultant red ylide solution is added dropwise a solution of 1.76 g. (5.0 mmoles) of the product of Example LXXIV in 17 ml. of dimethyl sulfoxide. After being stirred for 12 hours under nitrogen at room temperature the reaction is poured onto ice-water. The aqueous solution is overlaid with ethyl acetate, is acidified to pH~3 with 10% aqueous hydrochloric acid, and is extracted with ethyl acetate. The combined ethyl acetate extracts are washed with water, dried (anhydrous magnesium sulfate), and concentrated. Purification of the crude product by silica gel chromatography provides the desired N-methanesulfonyl-7-[2β-benzyloxymethyl-3α-(tetrahydropyran-2-yloxy)-5α-hydrocyclopent-1α-yl]-cis-5-heptenamide.

EXAMPLE LXXVI

A mixture of 1.82 g. (3.45 mmoles) of the chromatographed alcohol of Example LXXV, 5.0 ml. of pyridine and 0.736 ml. (7.78 mmoles) of acetic anhydride is stirred under nitrogen at 50° for 18 hours. The mixture is then cooled to room temperature and diluted with ethyl acetate. The organic solution is washed with 10% hydrochloric acid then water, is dried (anhydrous magnesium sulfate), and is concentrated. Purification of the crude product by silica gel chromatography provides the desired N-methanesulfonyl-7-[2β-benzyloxymethyl-3α-(tetrahydropyran-2-yloxy)-5α-acetoxycyclopent-1α-yl]-cis-5-heptenamide.

EXAMPLE LXXVII

A heterogeneous mixture of 1.73 g. (3.14 mmoles) of the chromatographed benzyl ether of Example LXXVI 324 mg. of 5% palladium on carbon, and 16.2 ml. of a 20:1 mixture of absolute ethanol:glacial acetic acid is stirred at room temperature under one atmosphere of hydrogen for 8 hours. The mixture is then filtered through Celite 545 and the filtrate is concentrated and is azeotroped under reduced pressure with toluene. Purification of the crude product by silica gel chromatography affords the desired N-methanesulfonyl-7-[2β-hydroxymethyl-3α-(tetrahydropyran-2-yloxy)-5α-acetoxycyclopent-1α-yl]-heptanamide.

EXAMPLE LXXVIII

To a mechanically stirred solution of 3.37 ml. (41.7 mmoles) of pyridine in 50 ml. of methylene chloride, cooled to 10° to 15° under nitrogen, is added portionwise over a period of 30 minutes 1.89 g. (18.9 mmoles) of chromium trioxide. The dark burgundy solution is let warm to room temperature then is cooled to 0°. To the cold solution is added a solution of 1.12 g. (2.37 mmoles) of the alcohol of Example LXXVII in 7.0 ml. of methylene chloride with the concomitant formation of a dense black precipitate. The suspension is stirred in the cold for 15 minutes then 7.21 g. (52.2 mmoles) of finely ground sodium bisulfite monohydrate is added. After being stirred for 10 minutes 6.52 g. (52.2 mmoles) of anhydrous magnesium sulfate is added. After being stirred for 5 minutes the dark suspension is filtered through a pad of Celite, is washed with methylene chloride, then is concentrated to afford the desired N-methanesulfonyl- 7-[2β-formyl-3α-(tetrahydropyran-2-yloxy)-5α-acetoxycyclopent-1α-yl]heptanamide which is used without purification.

EXAMPLE LXXIX

To a suspension of 220 mg. (5.22 mmoles) of a 57.0% dispersion of sodium hydride in mineral oil in 40 ml. of 1,2-dimethoxyethane is added 1.16 g. (5.22 mmoles) of dimethyl-2-oxoheptylphosphonate. The mixture is stirred at room temperature for 1 hour under nitrogen with the concomitant formation of a dense white precipitate. To this suspension is added a solution of 1.24 g. (2.37 mmoles) of the aldehyde of Example LXXVII in 4 ml. of 1,2-dimethoxyethane. The solution is stirred at room temperature for 2.0 hours under nitrogen then is quenched by the addition of glacial acetic acid to pH~5 and is concentrated. Purification of the crude product by silica gel chromatography gives the desired N-methanesulfonyl-9α-acetoxy-11α-(tetrahydropyran-2-yloxy)15-oxo-13-trans-prostenamide.

EXAMPLE LXXX

To a solution, cooled to −78°, of 862 mg. (2.0 mmoles) of the enone of Example LXXIX in 20 ml. of tetrahydrofuran is added 16 ml. (4.0 mmoles) of a 0.25 M solution of lithium tri-sec butylborohydride in tetrahydrofuran. The solution is stirred at −78° under nitrogen for 1.0 hour then is quenched by the addition of 10 ml. of 40% aqueous acetic acid. The quenched reaction mixture is let warm to room temperature and is extracted with ethyl acetate; the combined organic extracts are washed with water and saturated brine, are dried (anhydrous magnesium sulfate), are concentrated, and azeotroped with toluene. Purification of the crude product by silica gel chromatography provides the N-methanesulfonyl-9α-acetoxy-11α-(tetrahydropyran-2-yloxy)-15α-hydroxy-13-trans-prostenamide and the N-methanesulfonyl-9α-acetoxy-11α-(tetrahydropyran-2-yloxy)-15β-hydroxy-13-trans-prostenamide.

EXAMPLE LXXXI

A mixture of 526 mg. (1.00 mmole) of the THP ether of Example LXXX, 3.0 ml. (3.0 mmoles) of 1.0 N aqueous sodium hydroxide, 3.0 ml. of tetrahydrofuran, and 3.0 ml. of absolute methanol is stirred under nitrogen at room temperature for 1.5 hours. The solution is then acidified by the addition of 3.0 ml. of 1.0 N hydrochloric acid and is extracted with ethyl acetate. The combined extracts are dried (anhydrous magnesium sulfate) and concentrated. Purification of the crude product by silica gel chromatography affords the desired N-methanesulfonyl-9α,15α-dihydroxy-11α-(tetrahydropyran-2-yloxy)-13-trans-prostenamide.

EXAMPLE LXXXII

A solution of 500 mg. of the THP ether of Example LXXXI in 5 ml. of a 65:35 mixture of glacial acetic acid:water is stirred at room temperature under nitrogen for 18 hours then is concentrated and azeotroped under reduced pressure with toluene. Purification of the crude product by silica gel chromatography gives the desired N-methanesufonyl-9α,11α,15α-trihydroxy-13-trans-prostenamide.

EXAMPLE LXXXIII

A solution of 1.24 g. (2.16 mmoles) of the THP ether of Example LXXX in 11 ml. of a 65:35 mixture of acetic acid:water is stirred at room temperature under nitrogen for 18 hours then is concentrated and azeotroped under reduced pressure with toluene. Purification of the crude product by silica gel chromatography provides the desired N-methanesulfonyl-9α-acetoxy-11α,15α-dihydroxy-13-trans-prostenamide.

EXAMPLE LXXXIV

A solution of 472 mg. (1.00 mmole) of the diol of Example LXXXIII 3.0 ml. (3.0 mmoles) of 1.0 N aqueous sodium hydroxide, 3.0 ml. of tetrahydrofuran, and 3.0 ml. of absolute methanol is stirred under nitrogen at room temperature for 2.5 hours. The solution is then acidified by the addition of 3.0 ml. of 1.0 N hydrochloric acid and is extracted with ethyl acetate. The combined organic extracts are dried (anhydrous magnesium sulfate) and concentrated. Purification of the crude product by silica gel chromatography provides the desired N-methanesulfonyl-9α,11α,15α-trihydroxy-13-trans-prostenamide.

EXAMPLE LXXXV

A solution of 250 mg. of the alcohol of Example LXXX, 0.250 ml. of dihydropyran, 2.5 ml. of methylene chloride, and 2.5 mg. of p-toluenesulfonic acid monohydrate is stirred at room temperature under nitrogen for 15 minutes. The reaction mixture is then diluted with ether, is washed with water, is dried (anhydrous magnesium sulfate), and is concentrated to provide the desired N-methanesulfonyl-9α-acetoxy-11α,1-5α-bis-(tetrahydropyran-2-yloxy)-13-trans-prostenamide.

EXAMPLE LXXXVI

A homogeneous solution of 0.289 g. (0.436 mmole) of the crude bis-THP ether of Example LXXXV, 1.30 ml. (1.30 mmoles) of a 1.0 N aqueous sodium hydroxide solution, 1.3 ml. of methanol, and 1.3 ml. of tetrahydrofuran is stirred at room temperature overnight. The reaction mixture is then quenched by the addition of 1.30 ml. (1.30 mmoles) of a 1.0 N aqueous hydrochloric acid solution and is diluted with ethyl acetate. The organic layer is dried (anhydrous magnesium sulfate) and concentrated. Purification of the crude product by silica gel chromatography affords the desired N-methanesulfonyl-9α-hydroxy-11α,15α-bis-(tetrahydropyran-2-yloxy)-13-trans-prostenamide.

EXAMPLE LXXXVII

A solution of 75 mg. of the alcohol of Example LXXXVI in 1.0 ml. of a 65:35 mixture of glacial acetic acid:water is stirred under nitrogen at room temperature for 20 hours, then is concentrated and azeotroped under reduced pressure with toluene. Purification of the crude product by silica gel chromatography gives the desired N-methanesulfonyl-9α,11α,15α-trihydroxy-13-trans-prostenamide.

EXAMPLE LXXXVIII

To a solution, cooled to −23° under nitrogen, of 0.218 g. (0.371 mmole) of the alcohol of Example LXXXVI in 4.0 ml. of acetone is added dropwise 0.163 ml. (0.408 mmole) of Jones' reagent. The reaction is stirred in the cold for 15 minutes then is quenched by the addition of 0.163 ml. of isopropyl alcohol. The quenched reaction is stirred in the cold for 5 minutes then is diluted with ethyl acetate. The organic solution is washed with water, is dried (anhydrous magnesium sulfate), and is concentrated to afford the desired N-methanesulfonyl-9-oxo-11α,15α-bis-(tetrahydropyran-2-yloxy)-13-trans-prostenamide.

EXAMPLE LXXXIX

A homogeneous solution of 0.190 g. of the crude bis-THP ether of Example LXXXVIII in 2.0 ml. of a 65:35 mixture of glacial acetic acid:water is stirred under nitrogen at room temperature for 12 hours, then is concentrated and azeotroped under reduced pressure with toluene. Purification of the crude product by silica gel chromatography affords the desired N-methanesulfonyl-9-oxo-11α,15α-dihydroxy-13-trans-prostenamide.

EXAMPLE XC

To a solution of 9.86 g. (20.0 mmoles) of the product of Example I in 14 ml. of dimethyl sulfoxide is added dropwise 15.0 ml. of a 2.0 M solution of sodium methylsulfinylmethide in dimethyl sulfoxide. To the resultant red ylide solution is added dropwise a solution of 1.76 g. (5.0 mmoles) of the product of Example LXXIV in 17 ml. of dimethyl sulfoxide. After being stirred for 12 hours under nitrogen at room temperature the reaction is poured onto ice-water. The aqueous solution is overlaid with ethyl acetate, is acidified to pH∼3 with 10% aqueous hydrochloric acid, and is extracted with ethyl acetate. The combined ethyl acetate extracts are washed with water, dried (anhydrous magnesium sulfate), and concentrated. Purification of the crude product by silica gel chromatography provides the desired N-acetyl-7-[2β-benzyloxymethyl-3α-(tetrahydropyran-2-yloxy)-5α-hydroxycylopent-1α-yl]-cis-5-heptenamide.

EXAMPLE XCI

A mixture of 1.72 g. (3.45 mmoles) of the chromatographed alcohol of Example XC, 5.0 ml. of pyridine and 0.736 ml. (7.78 mmoles) of acetic anhydride is stirred under nitrogen at 50° for 18 hours. The mixture is then cooled to room temperature and diluted with ethyl acetate. The organic solution is washed with 10% hydrochloric acid then water, is dried (anhydrous magnesium sulfate), and is concentrated. Purification of the crude product by silica gel chromatography provides the desired N-acetyl-7-[2β-benzyloxymethyl-3α-

(tetrahydropyran-2-yloxy)-5α-acetoxycyclopent-1α-yl]-cis-5-heptenamide.

EXAMPLE XCII

A heterogeneous mixture of 1.64 g. (3.14 mmoles) of the chromatographed benzyl ether of Example XCI, 324 mg. of 5% palladium on carbon, and 16.2 ml. of a 20:1 mixture of absolute ethanol:glacial acetic acid is stirred at room temperature under one atmosphere of hydrogen for 8 hours. The mixture is then filtered through Celite 545 and the filtrate is concentrated and is azeotroped under reduced pressure with toluene. Purification of the crude product by silica gel chromatography affords the desired N-acetyl-7-[2α-hydroxymethyl-3α-(tetrahydropyran-2-yloxy)-5α-acetoxycyclopent-1α-yl]heptanamide.

EXAMPLE XCIII

A mixture of 1.90 g. (4.45 mmole) of the product of Example XCII, 2.50 ml. of dry dimethyl sulfoxide, 2.72 g. (13.2 mmoles) of dicyclohexylcarbodiimide, and 0.85 g. (4.45 mmole) of pyridinium trifluoroacetate in 40 ml. of benzene is stirred at room temperature under nitrogen for 45 minutes then is diluted with ethyl acetate. The filtrate is concentrated, dissolved in methylene chloride and the solution is washed with water (3x) and saturated brine (1x), is dried (anhydrous magnesium sulfate), and is concentrated to afford the desired N-acetyl-7-[2β-formyl-3α-(tetrahydropyran-2-yloxy)-5α-acetoxycyclopent-1α-yl]-heptanamide which is used without purification.

EXAMPLE XCIV

To a suspension of 220 mg. (5.22 mmoles) of a 57.0% dispersion of sodium hydride in mineral oil in 40 ml. of 1,2-dimethoxyethane is added 1.16 g. (5.22 mmoles) of dimethyl-2-oxoheptylphosphonate. The mixture is stirred at room temperature for 1 hour under nitrogen with the concomitant formation of a dense white precipitate. To this suspension is added a solution of 1.17 g. (2.37 mmoles) of the aldehyde of Example XCIII in 4 ml. of 1,2-dimethoxyethane. The solution is stirred at room temperature for 2.0 hours under nitrogen then is quenched by the addition of glacial acetic acid to pH~5 and is concentrated. Purification of the crude product by silica gel chromatography gives the desired N-acetyl-9α-acetoxy-11α-(tetrahydropyran-2-yloxy)-15-oxo-13-trans-prostenamide.

EXAMPLE XCV

To a suspension of 275 mg. (6.53 mmoles) of a 57.0% dispersion of sodium hydride in mineral oil in 50 ml. of dry 1,2-dimethoxyethane is added 1.63 g. (6.53 mmoles) of phosphonate of Example XLIV. The solution is stirred at room temperature for 1 hour under nitrogen, then a solution of 1.54 g. (2.96 mmoles) of the aldehyde of Example LXXVIII in 6 ml. of 1,2-dimethoxyethane is added. The solution is stirred at room temperature for 2.0 hours under nitrogen then is quenched by the addition of glacial acetic acid to pH~5 and is concentrated. Purification of the crude product by silica gel chromatography provides the desired N-methanesulfonyl-9α-acetoxy-11α-(tetrahydropyran-2-yloxy)-16,16-dimethyl-15-oxo-13-trans-prostenamide.

EXAMPLE XCVI

To a solution, cooled to −78° under nitrogen, of 1.15 g. (2.0 mmoles) of the product of Example XCV in 15 ml. of dry tetrahydrofuran is added dropwise 4.0 ml. (4.0 mmoles) of a 1.0 M solution of lithium tri-ethylborohydride in tetrahydrofuran. After 45 minutes the reaction is quenched by the dropwise addition of acetic acid (pH~5). The quenched reaction is let warm to room temperature and is concentrated. The resultant product is dissolved in methylene chloride and is washed with water, dried (anhydrous magnesium sulfate), and concentrated. Chromatographic purification of the crude product provides the desired N-methanesulfonyl 9α-acetoxy-11α-(tetrahydropyran-2-yloxy)-16,16-dimethyl-15α-hydroxy-13-trans-prostenamide and the N-methanesulfonyl 9α-acetoxy-11α-(tetrahydropyran-2-yloxy)16,16-dimethyl-15β-hydroxy-13-trans-prostenamide.

EXAMPLE XCVII

To a suspension 275 mg. (6.53 mmoles) of a 57.0% dispersion of sodium hydride in mineral oil in 50 ml. of dry 1,2-dimethoxyethane is added 1.63 g. (6.53 mmoles) of the phosphonate of Example XLIV. The solution is stirred at room temperature for 1 hour under nitrogen, then a solution of 1.48 g. (2.96 mmoles) of the aldehyde of Example XCIII in 6 ml. of 1,2-dimethoxyethane is added. The solution is stirred at room temperature for 2.0 hours under nitrogen then is quenched by the addition of glacial acetic acid to pH~5 and is concentrated. Purification of the crude product by silica gel chromatography provides the desired N-acetyl-9α-acetoxy-11α-(tetrahydropyran-2-yloxy)-16,16-dimethyl-15-oxo-trans-prostenamide.

EXAMPLE XCVIII

To a solution, cooled to −78° under nitrogen, of 1.56 g. (3.0 mmoles) of the product of Example XCVII in 20 ml. of dry tetrahydrofuran is added dropwise 14.6 ml. (6.0 mmoles) of a 0.41 M solution of lithium tri-ethyl borohydride in tetrahydrofuran. After 45 minutes the reaction is quenched by the dropwise addition of acetic acid (pH~5). The quenched reaction is let warm to room temperature and is concentrated. The concentrate is dissolved in methylene chloride and is washed with water, dried (anhydrous magnesium sulfate), and is concentrated. Chromatographic purification of the crude product affords the desired N-acetyl 9α-acetoxy-11α-(tetrahydropyran-2-yloxy)-16,16-dimethyl-15α-hydroxy-13-trans-prostenamide and the N-acetyl 9α-acetoxy-11α-(tetrahydropyran-2-yloxy)-16,16-dimethyl-15β-hydroxy-13-trans-prostenamide.

EXAMPLE XCIX

To a solution 3.21 g. (6.25 mmoles) of the product of Example XXX in 5 ml. of dimethyl sulfoxide is added 6.00 ml. (12.0 mmoles) of a 2.0 M solution of sodium methylsulfinylmethide in dimethyl sulfoxide. The resultant red ylide solution is stirred for 10 minutes then a solution of 338 mg. (1.25 mmoles) of the triol of Example XXV in 2.0 ml. of dimethyl sulfoxide is added dropwise. The mixture is stirred at room temperature under nitrogen for 4 hours then is poured onto a mixture of ethyl acetate ice-water. The aqueous layer is acidified with 10% aqueous hydrochloric acid and is extracted with ethyl acetate; the combined organic extracts are washed with water and saturated brine, are dried (anhydrous magnesium sulfate), and concentrated. Purification of the crude product by silica gel chromatography provides the desired N-methanesulfonyl-9α,11α,15α-trihydroxy-5-cis-13-trans-prostadienamide.

EXAMPLE C

To a solution 3.01 g. (6.25 mmoles) of the product of Example I in 4 ml. of dimethyl sulfoxide is added 6.00 ml. (12.0 mmoles) of a 2.0 M solution of sodium methylsulfinylmethide in dimethyl sulfoxide. The resultant red ylide solution is stirred for 10 minutes then a solution of 338 mg. (1.25 mmoles) of the triol of Example XXV in 2.0 ml. of dimethyl sulfoxide is added dropwise. The mixture is stirred at room temperature under nitrogen for 4 hours then is poured onto a mixture of ethyl acetate ice-water. The aqueous layer is acidified with 10% aqueous hydrochloric acid and is extracted with ethyl acetate; the combined organic extracts are washed with water and saturated brine, and dried (anhydrous magnesium sulfate), and concentrated. Purification of the crude product by silica gel chromatography provides the desired N-acetyl-9α,11α,15α-trihydroxy-5-cis-13-trans-prostadienamide.

EXAMPLE CI

To a solution, cooled in ice under nitrogen, of 75 mg. of N-acetyl 9-oxo-11α,15α-dihydroxy-13-trans-5-cis-prostadienamide in 1.5 ml. of methylene chloride is added 350 μl of pivaloyl chloride followed by 450 ml. of triethylamine. After being stirred at room temperature for 5 hours the mixture is poured onto a mixture of ethyl acetate/ice. The aqueous layer is extracted with ethyl acetate; the combined organic extracts are washed with 10% hydrochloric acid, with saturated bicarbonate, with water, is dried (anhydrous magnesium sulfate), and is concentrated. Purification of the crude product by chromatography provides the desired N-acetyl 9-oxo-11α,15α-bis-pivaloyloxy-5-cis-13-trans-prostadienamide.

EXAMPLE CII

To a solution, cooled in ice under nitrogen, of 125 mg. of N-methanesulfonyl 9α,11α,15α-trihydroxy-5-cis-13-trans-prostadienamide in 2.5 ml. of methylene chloride is added 0.50 ml. of benzoyl chloride followed by 0.625 ml. of triethylamine. After being stirred at room temperature for 5 hours. The mixture is poured onto a mixture of ethyl acetate:ice water. The aqueous layer is further extracted with ethyl acetate; the combined organic extracts are washed with 10% hydrochloric acid and with water, is dried (anhydrous magnesium sulfate), and is concentrated. Purification of the crude product by chromatography provides the desired N-methanesulfonyl 9α,11α,15α-tri-benzoyloxy-5-cis-13-trans-prostadienamide.

EXAMPLE CIII

To a solution of 991 mg. (0.2 mmoles) of the product of Example LII in 2 ml. of dry tetrahydrofuran is added 58 mg. (0.66 mmole) of formic acetic anhydride and 70 mg. (0.66 mmole) of 2,6-lutidine. The solution is stirred for 4 hours under nitrogen at room temperature then 36 mg. (2.0 mmoles) of water is added. The mixture is stirred at room temperature for an additional 1.0 hour then is diluted with ethyl acetate. The diluted solution is washed with 0.1 N hydrochloric acid (1×), with water (1×), and with saturated brine (1×) is dried (anhydrous magnesium sulfate), and is concentrated. Purification of the crude residue by silica gel chromatography affords the N-methanesulfonyl 9-oxo-11α,15α-bis-formyloxy-16,16-dimethyl-5-cis-13-trans-prostadienamide.

EXAMPLE CIV

A mixture of 3.98 g. (20 mmoles) of 5-bromovaleric acid chloride and 2.42 g. (20 mmoles) of benzamide was heated on a steam bath under nitrogen for 45 minutes. The mixture was let cool and the resultant solid was recrystallized from ethanol as colorless needles weighing 2.46 g. (44.8% yield) melting at 122°–123°.

The nmr spectrum ($CDCl_3$) of the product exhibited multiplets at 8.03–7.44 δ for the aromatic protons, a triplet at 3.47 δ (J = 6 cps) for the $CH_2\underline{Br}$, a triplet at 3.08 δ (J = 7 cps) for the $CH_2CO$, and a multiplet at 2.10–1.80 δ for the $\underline{CH_2CH_2}$. The ir spectrum ($CHCl_3$) of the product exhibited a strong absorbance at 5.90μ for the carbonyl groups.

A solution of 2.84 g. (10 mmoles) of the N-benzoyl-5-bromovaleramide prepared above and 3.93 g. (15 mmoles) of triphenylphosphine in 50 ml. of acetonitrile was heated at reflux, under nitrogen, for 72 hours. The acetonitrile was removed by rotary evaporation and the resultant solid was triturated with benzene (3×) then was recrystallized from methylene chloride:ethyl acetate to afford the desired [4-benzoylaminocarbonylbutyl]-triphenylphosphonium bromide weighing 2.38 g. (43.7% yield) melting at 193°–194°.

The nmr spectrum ($CDCl_3$) of the product exhibited multiplets at 8.31–7.26 δ for the aromatic protons, a multiplet at 3.97–3.42 δ for the $CH_2P$, a multiplet at 3.25–2.91 δ for the $CH_2CO$, and multiplets at 2.18–1.57 δ for the $\underline{CH_2CH_2}$. The ir spectrum ($CHCl_3$) of the product exhibited a strong absorption at 1725 $cm^{-1}$ for the carbonyl groups.

The above product may be caused to react with the known 2-[5α-hydroxy-3α-(tetrahydropyran-2-yloxy)-2β-(3α-(tetrahydropyran-2-yloxy)-trans-1-cis-5-octadien-1-yl)cyclopent-1α-yl]acetaldehyde, γ-hemiacetal (E. J. Corey, et al., *J. Am. Chem. Soc.*, 93, 1490 (1971) to produce N-benzoyl-9α-hydroxy-11α,15α-bis-(tetrahydropyran-2-yloxy)-cis-5-trans-13-cis-17-prostatrienamide which may be converted by known reactions (E. J. Corey, ibid) into the N-benzoyl prostaglandin $F_{3\alpha}$ carboxamide or the N-trimethylacetyl prostaglandin $E_3$.

The above product may be caused to react with the mixed 2-[5α-hydroxy-3α-(tetrahydropyran-2-yloxy)-2β-(3β-methyl-3α-(tetrahydropyran-2-yloxy)-trans-1-octen-1-yl)cyclopent-1α-yl]acetaldehyde, γ-hemiacetal and 2-]5α-hydroxy-3α-(tetrahydropyran-2-yloxy)-2β-(3α-methyl-3β-(tetrahydropyran-2-yloxy)-trans-1-octen-1-yl)cyclopent-1α-yl]acetaldehyde, γ-hemiacetal to produce N-benzoyl-9α-hydroxy-11α,15α-bis-(tetrahydropyran-2-yloxy)15β-methyl-cis-5-trans-13-prostadienamide and N-benzoyl-9α-hydroxy-11α,15β-bis-(tetrahydropyran-2-yloxy)-15α-methyl-cis-5-trans-13-prostadienamide called Compound A. Compound A may be hydrolyzed as described in Example III to produce the N-benzoyl-15-methyl prostaglandin $F_2\alpha$ carboxamides (which may be subjected to catalytic hydrogenation as described in Example VII to produce N-benzoyl 15-methyl-13,14-dihydroprostaglandin $F_{1\alpha}$ carboxamide). Compound A may be subjected to oxidation as described in Example IV followed by hydrolysis as described in Example V to produce N-benzoyl-15-methyl prostaglandin $E_2$ carboxamide called Compound B. Compound B may be dehydrated as described in Example VI to produce N-benzoyl 15-methylprostaglandin $A_2$ carboxamide. Compound B may also be catalytically hydrogenated as described in Example VII to produce N-benzoyl 15-methyl-13,14-dihydroprostaglandin $E_1$ carboxamide which may be dehydrated as described in Example VI to produce N-benzoyl 15-methyl-13,14-dihydroprostaglandin $A_1$ carboxamide or reduced as described in Example XXXVI to the N-benzoyl 15-methyl-13,14-dihydroprostaglandin $F_1\beta$ carboxamide.

Compound A may be subjected to carefully controlled catalytic reduction to produce N-benzoyl-9α-hydroxy-11α,15-bis-(tetrahydropyran-2-yloxy)-15-methyl-trans-13-prostenamide which may be converted by known reactions (E. J. Corey, et al., *J. Am. Chem. Soc.*, 92, 2586 (1970) to N-benzoyl 15-methyl prostaglandin $F_{1\alpha}$ carboxamide and N-benzoyl 15-methylprostaglandin $E_1$ carboxamide. The latter may be converted as described in Example VI to N-benzoyl 15-methylprostaglandin $A_1$ carboxamide or as described in Example XXXVI to N-benzoyl 15-methylprostaglandin $F_1\beta$ carboxamide.

The above product may be caused to react with the hemiacetal, 2-[3α,5α-dihydroxy-2β-(3α-hydroxy-trans-1-octen-1-yl) cyclopent-1α-yl]acetaldehyde, γ-hemiacetal, prepared in Example XXV to produce N-benzoyl prostaglandin $F_2\alpha$.

The above product may be caused to react with the hemiacetal, 2-[3α,5α-dihydroxy-2β-(3α-hydroxyoct-1-yl)cyclopent-1α-yl]acetaldehyde, γ-hemiacetal, prepared in EXAMPLE XXXVI to provide N-benzoyl 13,14-dihydroprostaglandin $F_2\alpha$.

The above product may be caused to react with the 2-[5α-hydroxy-3α-(tetrahydropyran-2-yloxy)-2β-(3α-(tetrahydropyran-2-yloxy)oct-1-yl)cyclopent-1α-yl]acetaldehyde, γ-hemiacetal prepared in Example XXVII to produce N-benzoyl-9α-hydroxy-11α,15α-bis-(tetrahydropyran-2-yloxy)-cis-5-prostenamide called Compound C. Compound C may be hydrolyzed as described in Example III to produce the N-benzoyl 13,14-dihydroprostaglandin $F_2\alpha$ carboxamide. Compound C may be subjected to oxidation as described in Example IV followed by hydrolysis as described in Example V to produce the N-benzoyl 13,14-dihydroprostaglandin $E_2$ carboxamide. The latter may be dehydrated as described in Example VI to produce the N-benzoyl 13,14-dihydroprostaglandin $A_2$ carboxamide or reduced as described in Example XXXVI to the N-benzoyl 13,14-dihydroprostaglandin $F_2\beta$ carboxamide.

The above product may be caused to react with the mixed 2-[5α-hydroxy-3α-(tetrahydropyran-2-yloxy)-2β-(3β-methyl-3α-(tetrahydropyran-2-yloxy)oct-1-yl)cyclopent-1α-yl]acetaldehyde, γ-hemiacetal and 2-[5α-hydroxy-3α-(tetrahydropyran-2-yloxy)-2β-(3α-methyl-3β-(tetrahydropyran-2-yloxy)oct-1-yl)cyclopent-1α-yl]acetaldehyde, γ-hemiacetal to produce N-benzoyl-9α-hydroxy-15-methyl-11α,15-bis(tetrahydropyran-2-yloxy)-cis-5-prostenamide called Compound D. Compound D may be hydrolyzed as described in Example III to produce the N-benzoyl 15-methyl-13,14-dihydroprostaglandin $F_2\alpha$ carboxamide. Compound D may be subjected to oxidation as described in Example IV followed by hydrolysis as described in Example V to produce the N-benzoyl 15-methyl-13,14-dihydroprostaglandin $E_2$ carboxamide. The latter may be dehydrated as described in Example V to produce the N-benzoyl 15-methyl-13,14-dihydroprostaglandin $A_2$ carboxamide or reduced as described in Example XXXVI to produce the N-benzoyl 15-methyl-13,14-dihydroprostaglandin $F_2\beta$ carboxamide.

The above product may be caused to react with the 2-[5α-hydroxy-3α-(tetrahydropyran-2-yloxy)-2β-(3β-(tetrahydropyran-2-yloxy)oct-1-yl)cyclopent-1α-yl]acetaldehyde, γ-hemiacetal prepared in Example XXIII to produce N-benzoyl-9α-hydroxy-11α,15β-bis-(tetrahydropyran-2-yloxy)-cis-5-prostenamide called Compound E. Compound E may be hydrolyzed as described in Example III to produce the N-benzoyl-15-epi-13,14-dihydroprostaglandin $F_2\alpha$ carboxamide. Compound E may be subjected to oxidation as described in Example IV followed by hydrolyis as described in Example V to produce the N-benzoyl 15-epi-13,14-dihydroprostaglandin $E_2$ carboxamide. The latter may be dehydrated as described in Example VI to produce the N-benzoyl-15-epi-13,14-dihydroprostaglandin $A_2$ carboxamide or reduced as described in Example XXXVI 'to produce the N-benzoyl 13,14-dihydroprostaglandin $F_2\beta$ carboxamide.

The above product may be caused to react with the 2-[5α-hydroxy-3α-(tetrahydropyran-2-yloxy)-2β-(3β-(tetrahydropyran-2-yloxy)-1-trans-octen-1-yl)cyclopent-1α-yl]acetaldehyde, γ-hemiacetal prepared in Example XXIV to produce N-benzoyl-9α-hydroxy-11α,15β-bis(tetrahydropyran-2-yloxy)-trans-13-cis-5-prostadienamide called Compound F. Compound F may be hydrolyzed a described in Example III to produce the N-benzoyl 15-epi-prostaglandin $F_2\alpha$ carboxamide. Compound F may be subjected to oxidation as described in Example IV followed by hydrolysis as described in Example V to produce the N-benzoyl 15-epi prostaglandin $E_2$ carboxamide. The latter may be dehydrated as described in Example VI to produce the N-benzoyl 15-epi prostaglandin $A_2$ carboxamide or reduced as described in Example XXXVI to produce the N-benzoyl 15-epi-prostaglandin $F_2\beta$ carboxamide.

The above product may be caused to react with the 2-[3α,5α-dihydroxy-2β-(3β-hydroxy-trans-1-octen-1-yl)cyclopent-1α-yl]acetaldehyde, γ-hemiacetal prepared in Example XXI to provide the N-benzoyl 15-epi-prostaglandin $F_2\alpha$ carboxamide.

The above product may be caused to react with the 2-[3α,5α-dihydroxy-2β-(3β-hydroxyoct-1-yl)cyclopent-1α-yl]acetaldehyde, γ-hemiacetal prepared in Example XXI to provide the N-benzoyl 15-epi-13,14-dihydroprostaglandin $F_2\alpha$.

The above product may be caused to react with the 2-[3α,5α-dihydroxy-2β-(3α-hydroxy-3β-methyl-trans-1-octen-1-yl)cyclopent-1α-yl]acetaldehyde, γ-hemiacetal prepared in Example XXXVII to provide the N-benzoyl 15-methyl-prostaglandin $F_2\alpha$ carboxamide.

The above product may be caused to react with the 2-[3α,5α-dihydroxy-2β-(3α-hydroxy-3β-methyl-oct-1-yl)cyclopent-1α-yl]acetaldehyde, γ-hemiacetal prepared in Example XXXVII to provide the N-benzoyl 15-methyl-13,14-dihydroprostaglandin $F_2\alpha$.

EXAMPLE CV

To a solution of 2.73 g. (5.0 mmoles) of [4-benzoylaminocarbonylbutyl]triphenylphosphonium bromide, as prepared in Example CIV, in 10 ml. of dry dimethyl sulfoxide is added 2.22 ml. (4.54 mmoles) of a 2.05 M solution of sodium methylsulfinylmethide in dimethyl sulfoxide. To this red ylide solution is added dropwise a solution of 0.219 g. (0.5 mmole) of 2-[5α-hydroxy-3α-(tetrahydropyran-2-yloxy)-2β-(3α-(tetrahydropyran-2-yloxy)-trans-1-octen-1-yl)cyclopent-1α-yl]acetaldehyde, γ-hemiacetal in 1.0 ml. of dry dimethyl sulfoxide. After being stirred at room temperature under nitrogen for 20 hours the reaction is poured onto ice water. The aqueous solution is covered with ether and is acidified to pH ~ 3 by the addition of 10% hydrochloric acid. The aqueous mixture is further extracted with ether (3×); the combined ethereal extracts are dried (anhydrous magnesium sulfate) and concentrated to afford a viscous oil. Purification of the crude product is effected by silica gel chromatography to afford the N-benzoyl-9α-hydroxy-11α,15α-bis-(tetrahydropyran-2-yloxy)-cis-5-trans-13-prostadienamide.

The above product may be hydrolyzed as described in Example III to provide the N-benzoyl prostaglandin $F_{2\alpha}$ carboxamide which may be catalytically reduced as described in Example VII to provide the N-benzoyl 13,14-dihydroprostaglandin $F_{1\alpha}$ carboxamide.

The above product may also be subjected to catalytic reduction to produce N-benzoyl-9α-hydroxy-11α,15α-bis(tetrahydropyran-2-yloxy)-trans-13-prostenamide which may be converted by known reactions (E. J. Corey, et al., *J. Am. Chem. Soc.*, 92, 2586 (1970) to N-benzoyl prostaglandin $F_{1\alpha}$ carboxamide or N-benzoyl prostaglandin $E_1$ carboxamide. The latter may be converted by known reactions (Example VI) to N-benzoyl prostaglandin $A_1$ carboxamide or (Example XXXVI) to N-benzoyl prostaglandin $F_{1\beta}$ carboxamide.

The above product may also be subjected to catalytic reduction to produce the N-benzoyl-9α-hydroxy-11α,15α-bis(tetrahydropyran-2-yloxy)prostanamide called Compound A. Compound A may be hydrolyzed as described in Example III to produce the N-benzoyl-13,14-dihydroprostaglandin $F_{1\alpha}$ carboxamide. Compound A may be subjected to oxidation as described in Example IV followed by hydrolysis as described in Example V to produce the N-benzoyl-13,14-dihydroprostaglandin $E_1$ carboxamide called Compound B. Compound B may be dehydrated as described in Example VI to produce the N-benzoyl-13,14-dihydroprostaglandin $A_1$ carboxamide or reduced as described in Example XXXVI to produce the N-benzoyl-13,14-dihydroprostaglandin $F_{1\beta}$ carboxamide.

EXAMPLE CVI

To a solution cooled to −20° under nitrogen of 0.401 g. of the N-benzoyl-9α-hydroxy-11α,15α-bis-(tetrahydropyran-2-yloxy)-cis-5-trans-13-prostadienamide of Example CV in 4.0 ml. of reagent grade acetone is added 0.165 ml. of Jones' reagent. The mixture is stirred in the cold for 20 minutes then is quenched by the addition of 0.165 ml. of isopropanol. The mixture is stirred for 5 minutes then is diluted with ethyl acetate; the diluted solution is washed with water (2×) and with saturated brine (1×), is dried (anhydrous magnesium sulfate) and is concentrated to give the crude N-benzoyl-9-oxo-11α,15α-bis-(tetrahydropyran-2-yloxy)-cis-5-trans-13-prostadienamide.

EXAMPLE CVII

A solution of 352 mg. of the crude N-benzoyl-9-oxo-11α,15α-bis-tetrahydropyran-2-yloxy)-cis-5-trans-13-prostadienamide of Example CVI in 4.0 ml. of a 65:35 mixture of acetic acid:water is stirred under nitrogen for 4.5 hours at 40° ± 2° then is concentrated. The resultant oil is subjected to column chromatography on silica gel (SilicAR CC-4) to afford the desired N-benzoyl-9-oxo-11α,15α-dihydroxy-cis-5-trans-13-prostadienamide, the N-benzoyl prostaglandin $E_2$ carboxamide.

The above product may be dehydrated as described in Example VI to provide the N-benzoyl prostaglandin $A_2$ carboxamide or reduced as described in Example XXXVI to provide the N-benzoyl prostaglandin $F_{2\beta}$ carboxamide.

The above product may also be catalytically reduced as described in Example VII to produce the N-benzoyl 13,14-dihydroprostaglandin $E_1$ carboxamide. The latter may be dehydrated as described in Example VI to produce the N-benzoyl 13,14-dihydroprostaglandin $A_1$ carboxamide or reduced as described in Example XXXVI to produce the N-benzoyl 13,14-dihydroprostaglandin $F_{1\beta}$ carboxamide.

EXAMPLE CVIII

To a solution of 197 mg. (0.5 mmole) of the product of Example V in 20 ml. of anhydrous ether is added 10 g. of dicyclohexylcarbodiimide. Cupric chloride (trace) is then added and the resulting mixture is stirred 48 hours under nitrogen at room temperature. The reaction is quenched by the addition of oxalic acid until frothing stops. The mixture is diluted with benzene, is filtered, and is concentrated. Purification of the crude product by silica gel chromatography provides the desired N-acetyl prostaglandin $A_2$ carboxamide.

EXAMPLE CIX

To a solution of the known 9α-hydroxy-11α,15α-(tetrahydropyran-2-yloxy)-cis-5-trans-13-prostadienoic acid (523 mg.; 1.0 mmole) in 5.0 ml. of acetonitrile is added 101 mg. (1.0 mmole) of triethylamine. This solution is added dropwise to a solution of 118 mg. (1.1 mmoles) of methanesulfonylisocyanate in 5.0 ml. of acetonitrile. The resulting solution is stirred under nitrogen for 2.0 hours then is concentrated. The resultant product is dissolved in water, the aqueous layer is acidified to pH ~ 3 with 10% hydrochloric acid, and is extracted with ethyl acetate. The combined organic extracts are dried (anhydrous magnesium sulfate) and are concentrated; purification of the crude product by silica gel chromatography provides the N-methanesulfonyl 9α-hydroxy-11α,15α-(tetrahydropyran-2-yloxy)-cis-5-trans-13-prostadienamide. This product may be converted into the corresponding N-methanesulfonyl $PGF_{2\beta}$, $PGF_{2\alpha}$, $PGE_2$ and $PGA_2$ carboxamides by the procedures described above.

EXAMPLE CX

To a solution of the known 9α-hydroxy-11α,15α-(tetrahydropyran-2-yloxy)-trans-13-prostenoic acid (525 mg.; 1.0 mmole) in 5.0 ml. of acetonitrile is added 101 mg. (1.0 mmole) of triethylamine. To this solution is added dropwise a solution of 93 mg. (1.1 mmole) of acetylisocyanate in 5.0 ml. of acetonitrile. The resulting solution is stirred under nitrogen for 2.0 hours then is concentrated. The resultant product is dissolved in water, the aqueous layer is acidified to pH ~ 3 with 10% hydrochloric acid, and is extracted with ethyl acetate. The combined organic extracts are dried (anhydrous magnesium sulfate) and are concentrated; purification of the crude product by silica gel chromatography provides the N-acetyl 9α-hydroxy-11α,15α-(tetrahydropyran-2-yloxy)-trans-13-prostenamide. This product may be converted into the corresponding N-acetyl PGF$_1$ α, PGF$_1$ β, PGE$_1$, and PGA$_1$ carboxamides by the procedures described above.

What is claimed is:

1. A compound of the structure:

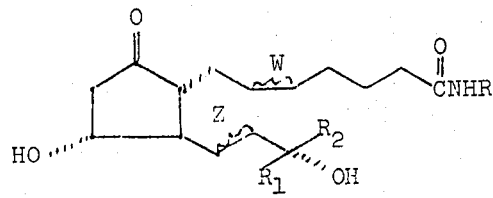

wherein R is alkanoyl having from 2–8 carbon atoms or cycloalkanoyl from 4 to 8 carbon atoms; aryoyl or substituted aryoyl of from 7 to 11 carbon atoms wherein said substituent is methyl, halogen, or methoxy; alkylsulfonyl of from 1 to 7 carbon atoms; arylsulfonyl or substituted arylsulfonyl wherein said substituent is methyl, halogen, or methoxy;

$R_1$ is hydrogen or alkyl having from 1 to 3 carbon atoms;

$R_2$ is alkyl having from 5 to 11 carbon atoms;

W is a single bond or cis double bond;

Z is single bond or trans double bond;

and the $C_{11}$ and $C_{15}$ esters thereof wherein said esterifying group is formyl, alkanoyl, having from 2 to 5 carbon atoms, or benzoyl.

2. A compound according to claim 1 wherein R is acetyl, $R_1$ is hydrogen, $R_2$ is n-pentyl, W is a cis double bond, and Z is a trans double bond.

3. A compound according to claim 1 wherein R is propionyl, $R_1$ is hydrogen, $R_2$ is n-pentyl, W is a cis double bond, and Z is a trans double bond.

4. A compound according to claim 1 wherein R is cyclopropylcarbonyl, $R_1$ is hydrogen, $R_2$ is n-pentyl, W is a cis double bond, and Z is a trans double bond.

5. A compound according to claim 1 wherein R is pivaloyl, $R_1$ is hydrogen, $R_2$ is n-pentyl, W is a cis double bond, and Z is a trans double bond.

6. A compound according to claim 1 wherein R is methanesulfonyl, $R_1$ is hydrogen, $R_2$ is n-pentyl, W is a cis double bond, and Z is a trans double bond.

7. A compound according to claim 1 wherein R is acetyl, $R_1$ is hydrogen, $R_2$ is 1,1-dimethylpent-1-yl, W is a cis double bond, and Z is a trans double bond.

8. A compound according to claim 1 wherein R is methanesulfonyl, $R_1$ is hydrogen, $R_2$ is 1,1-dimethylpent-1-yl, W is a cis double bond, and Z is a trans double bond.

9. A compound according to claim 1 wherein R is 2-thiophenesulfonyl, $R_1$ is hydrogen and $R_2$ is n-pentyl, W is a cis double bond and Z is a trans double bond.

10. A compound according to claim 1 wherein R is methanesulfonyl, $R_1$ is hydrogen and $R_2$ is n-pentyl, W is a single bond and Z is a trans double bond.

11. A compound according to claim 1 wherein R is acetyl, $R_1$ is hydrogen and $R_2$ is n-pentyl, W is a single bond and Z is a trans double bond.

* * * * *